(12) United States Patent
Murase et al.

(10) Patent No.: US 8,642,777 B2
(45) Date of Patent: Feb. 4, 2014

(54) PROCESS FOR PRODUCING 3-ALKOXY-2-AMINO-6-FLUOROBICYCLO [3.1.0] HEXANE-2,6-DICARBOXYLIC ACID DERIVATIVE AND INTERMEDIATE THEREOF

(75) Inventors: Noriaki Murase, Toshima-ku (JP); Toshihito Kumagai, Toshima-ku (JP); Hisaya Wada, Toshima-ku (JP); Hisahide Tanimoto, Toshima-ku (JP); Koumei Ohta, Toshima-ku (JP); Yoshihiro Kimura, Toshima-ku (JP)

(73) Assignee: Taisho Pharmaceutical Co., Ltd, Tokyo (JP)

( * ) Notice: Subject to any disclaimer, the term of this patent is extended or adjusted under 35 U.S.C. 154(b) by 0 days.

(21) Appl. No.: 13/510,428

(22) PCT Filed: Nov. 18, 2010

(86) PCT No.: PCT/JP2010/006757
§ 371 (c)(1),
(2), (4) Date: May 17, 2012

(87) PCT Pub. No.: WO2011/061935
PCT Pub. Date: May 26, 2011

(65) Prior Publication Data
US 2012/0238763 A1    Sep. 20, 2012

(30) Foreign Application Priority Data

Nov. 19, 2009    (JP) .................................. 2009-264071

(51) Int. Cl.
*C07D 293/00*    (2006.01)

(52) U.S. Cl.
USPC .................................................... 548/301.1

(58) Field of Classification Search
USPC ........ 548/301.1; 556/400, 437; 558/426, 431; 560/119, 53, 83; 562/501; 564/1, 57, 564/169
See application file for complete search history.

(56) References Cited

U.S. PATENT DOCUMENTS

| 7,157,594 | B2 * | 1/2007 | Nakazato et al. ............. 560/119 |
| 7,381,746 | B2 | 6/2008 | Yasuhara et al. |
| 7,960,579 | B2 | 6/2011 | Yasuhara et al. |
| 8,039,647 | B2 | 10/2011 | Yasuhara et al. |
| 2005/0119345 | A1 | 6/2005 | Nakazato et al. |
| 2006/0142388 | A1 | 6/2006 | Yasuhara et al. |
| 2007/0021394 | A1 | 1/2007 | Yasuhara et al. |

FOREIGN PATENT DOCUMENTS

| JP | 2004-339199 A | 12/2004 |
| JP | 2006-193507 A | 7/2006 |
| WO | 03/061698 A1 | 7/2003 |
| WO | 2005/000790 A1 | 1/2005 |
| WO | 2005/000791 A1 | 1/2005 |

OTHER PUBLICATIONS

Shigetada Nakanishi, "Molecular Diversity of Glutamate Receptors and Implications for Brain Function", Science in Japan: Articles, 1992, pp. 597-603, vol. 258.
Darryle Schoepp, et al., "Pharmacological and functional characteristics of metabotropic excitatory amino acid receptors", Trends in Pharmacological Sciences, Dec. 1990, pp. 508-515, vol. 11.
Darryle D. Schoepp, et al., "Metabotropic glutamate receptors in brain function and pathology", Trends in Pharmacological Sciences, Jan. 1993, pp. 13-20, vol. 14.
Atsuro Nakazato, et al., "Synthesis, in Vitro Pharmacology, Structure—Activity Relationships, and Pharmacokinetics of 3-Alkoxy-2-amino-6-fluorobicyclo[3.1.0]hexane-2,6-dicarboxylic Acid Derivatives as Potent and Selective Group II Metabotropic Glutamate Receptor Antagonists", Journal of Medicinal Chemistry, 2004, pp. 4570-4587, vol. 47.
Akito Yasuhara, et al., "Synthesis, in vitro pharmacology, and structure—activity relationships of 2-aminobicyclo[3.1.0]hexane-2,6-dicarboxylic acid derivatives as mGluR2 antagonists", Bioorganic & Medicinal Chemistry, 2006, pp. 3405-3420, vol. 14.
Akito Yasuhara, et al., "Prodrugs of 3-(3,4-dichlorobenzyloxy)-2-amino-6-fluorobicyclo[3.1.0]hexane-2,6-dicarboxylic acid (MGS0039): A potent and orally active group II mGluR antagonist with antidepressant-like potential", Bioorganic & Medicinal Chemistry, 2006, pp. 4193-4207, vol. 14.
International Search Report, PCT/JP2010/006757, Jan. 25, 2011.

* cited by examiner

*Primary Examiner* — Wu-Cheng Winston Shen
*Assistant Examiner* — Blaine G Doletski
(74) *Attorney, Agent, or Firm* — Sughrue Mion, PLLC

(57) ABSTRACT

A process for producing a 3-alkoxy-2-amino-6-fluoro bicyclo [3.1.0]hexane-2,6-dicarboxylic acid derivative represented by the formula (I) or a salt thereof, which includes converting a compound represented by the formula (VI) or a salt thereof to the compound represented by the formula (I) or a salt thereof.

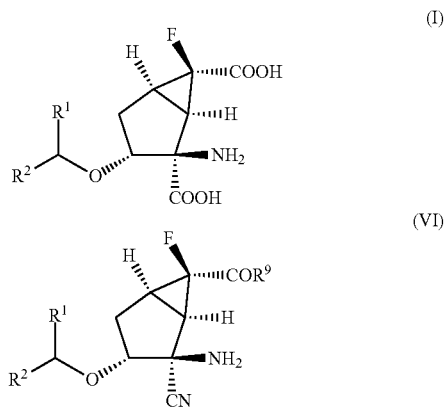

3 Claims, No Drawings

PROCESS FOR PRODUCING 3-ALKOXY-2-AMINO-6-FLUOROBICYCLO [3.1.0] HEXANE-2,6-DICARBOXYLIC ACID DERIVATIVE AND INTERMEDIATE THEREOF

CROSS REFERENCE TO RELATED APPLICATIONS

This application is a National Stage of International Application No. PCT/JP2010/006757 filed Nov. 18, 2010, claiming priority based on Japanese Patent Application No. 2009-264071 filed Nov. 19, 2009, the contents of all of which are incorporated herein by reference in their entirety.

TECHNICAL FIELD

The present invention relates to a process for producing a 3-alkoxy-2-amino-6-fluoro bicyclo[3.1.0]hexane-2,6-dicarboxylic acid derivative useful as a pharmaceutical. The invention also relates to a novel intermediate compound produced in the production process.

BACKGROUND ART

An excitatory amino acid such as glutamic acid modulates various physiological processes such as long term potentiation (learning and memory), synaptic plasticity development, motion control, respiration, cardiovascular modulation, and perception in the central nervous system (CNS) of a mammal. Presently, glutamate receptors are classified into two major groups, that is, "an ionotropic type in which the receptor has an ion channel structure": ion channel type glutamate receptor (iGluR), and "a metabotropic type in which the receptor is coupled to a G protein": metabotropic glutamate receptor (mGluR) (see, Non-Patent Document 1). It appears that receptors of either class mediate normal synaptic transmission in accordance with an excitatory pathway. It also appears that they are involved in modification of synaptic binding from the development stage throughout the lifetime (see, Non-Patent Document 2).

Eight subtypes of the metabotropic glutamate receptor that have been identified so far are classified into three groups (group I, II, and III) depending on pharmacological characteristics and intracellular second messengers to which they are coupled. Among them, group II receptor (mGluR2/mGluR3) binds with adenylate cyclase, and inhibits the accumulation of cyclic adenosine-1-phosphate (cAMP) stimulated by forskolin (see, Non-Patent Document 3). Thus, it is suggested that compounds that antagonize the activity of group II metabotropic glutamate receptors are effective for the treatment or prevention of acute and chronic psychiatric disorders and neurological diseases.

It is recognized that a 2-amino-6-fluoro bicyclo[3.1.0]hexane-2,6-dicarboxylic acid derivative having a substituent group on position 3 has a strong antagonistic effect on group II metabotropic glutamate receptor. As such, it is effective for the treatment and prevention of psychiatric disorders such as schizophrenia, anxiety and related ailments thereof, bipolar disorder, or epilepsy, and also of neurological diseases such as drug dependence, cognitive disorders, Alzheimer's disease, Huntington's disease, Parkinson's disease, dyskinesia associated with muscular rigidity, cerebral ischemia, cerebral failure, encephalopathy, or head trauma (see, Patent Documents 1 to 3 and Non-Patent Documents 4 to 6).

For example, as an antagonist substance of group II metabotropic glutamate receptor, 3-alkoxy-2-amino-6-fluoro bicyclo[3.1.0]hexane-2,6-dicarboxylic acid derivative represented by the following formula (IA), a pharmaceutically acceptable salt thereof, or a hydrate thereof is disclosed (see, Patent Document 1).

[Chemical Formula 1]

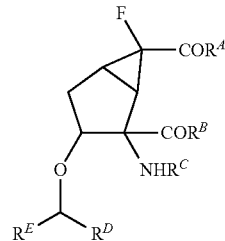

(IA)

(in the formula (IA), $R^A$ and $R^B$, which may be the same or different, each represent a hydroxyl group, a $C_{1-10}$ alkoxy group, a phenoxy group, a naphthyloxy group, a $C_{1-6}$ alkoxy group which is substituted with one or two phenyl groups, a $C_{1-6}$ alkoxy $C_{1-6}$ alkoxy group, a hydroxy $C_{2-6}$ alkoxy group, an amino group, an amino group which is substituted with the same or different one or two $C_{1-6}$ alkyl groups, an amino group which is substituted with the same or different one or two $C_{1-6}$ alkoxy $C_{1-6}$ alkyl groups, an amino group which is substituted with the same or different one or two hydroxy $C_{2-6}$ alkyl groups, an amino group which is substituted with the same or different one or two $C_{1-6}$ alkoxycarbonyl $C_{1-6}$ alkyl groups, or a native or non-native amino acid residue represented by $NR^F$—$CHR^G$-A-$CO_2R^H$ (wherein $R^F$ and $R^G$, which may be the same or different, each represent a hydrogen atom, a hydroxy $C_{1-6}$ alkyl group, a hydroxycarbonyl $C_{1-6}$ alkyl group, a $C_{1-10}$ alkyl group, a phenyl group, a phenyl $C_{1-6}$ alkyl group, a hydroxyphenyl group, a hydroxyphenyl $C_{1-6}$ alkyl group, a naphthyl group, a naphthyl $C_{1-6}$ alkyl group, an aromatic heterocyclic $C_{1-6}$ alkyl group, a $C_{1-6}$ alkoxy $C_{1-6}$ alkyl group, an amino $C_{2-6}$ alkyl group, a guanidino $C_{2-6}$ alkyl group, a mercapto $C_{2-6}$ alkyl group, a $C_{1-6}$ alkylthio $C_{1-6}$ alkyl group or an aminocarbonyl $C_{1-6}$ alkyl group, or $R^F$ and $R^G$ may bind to each other to represent a group capable of forming a methylene group, an ethylene group or a propylene group, or may together form a cyclic amino group; $R^H$ represents a hydrogen atom or a protecting group for carboxy group; and A represents a single bond, a methylene group, an ethylene group or a propylene group); $R^C$ represents a $C_{1-10}$ acyl group, a $C_{1-6}$ alkoxy $C_{1-6}$ acyl group, a hydroxy $C_{2-10}$ acyl group, a $C_{1-6}$ alkoxycarbonyl $C_{1-6}$ acyl group, a hydroxycarbonyl $C_{1-6}$ acyl group, or an amino acid residue represented by $R^I$—NH-A-CH—$R^G$—CO (wherein $R^G$ and A are as defined above, and $R^I$ represents a hydrogen atom or a protecting group for amino group); and $R^D$ and $R^E$, which may be the same or different, each represent a hydrogen atom, a $C_{1-10}$ alkyl group, a $C_{2-10}$ alkenyl group, a phenyl group, a naphthyl group, a 5-membered heteroaromatic ring containing one or more heteroatoms, or a phenyl group substituted with 1 to 5 substituent groups selected from the group consisting of a halogen atom, a $C_{1-10}$ alkyl group, a $C_{1-10}$ alkoxy group, a trifluoromethyl group, a phenyl group, a hydroxycarbonyl group, an amino group, a nitro group, a cyano group and a phenoxy group, or $R^D$ and $R^E$ may bind to each other to form a cyclic structure).

With respect to a lab-scale synthesis of an antagonist substance of group II metabotropic glutamate receptor that is represented by the formula (IA) and synthetic intermediate thereof, several studies have been made (see, Patent Documents 1 and 3 and Non-Patent Documents 4 and 6).

RELATED DOCUMENT

Patent Document

[Patent Document 1] Pamphlet of International Publication No. 2003/061698
[Patent Document 2] Pamphlet of International Publication No. 2005/000790
[Patent Document 3] Pamphlet of International Publication No. 2005/000791

Non-Patent Document

[Non-Patent Document 1] Science, 258, 597-603 (1992)
[Non-Patent Document 2] Trends Pharmacol. Sci., 11, 508-515 (1990)
[Non-Patent Document 3] Trends Pharmacol. Sci., 14, 13-20 (1993)
[Non-Patent Document 4] J. Med. Chem., 47, 4570-4587 (2004)
[Non-Patent Document 5] Bioorg. Med. Chem., 14, 3405-3420 (2006)
[Non-Patent Document 6] Bioorg. Med. Chem., 14, 4193-4207 (2006)

DISCLOSURE OF THE INVENTION

Problem to be Solved by the Invention

According to the conventional synthetic process disclosed in Patent Documents 1 and 3 and Non-Patent Documents 4 and 6, the antagonist substance of group II metabotropic glutamate receptor having the formula (IA) wherein $R^A$ and $R^B$ are a hydroxyl group and $R^C$ is a hydrogen atom is synthesized by performing many reaction steps, that is, nine to ten reaction steps, from 6-fluoro-2-oxo bicyclo[3.1.0]hexane-6-carboxylic acid ethyl ester (intermediate (IIA)) as a synthetic intermediate shown with the following formula (IIA).

[Chemical Formula 2]

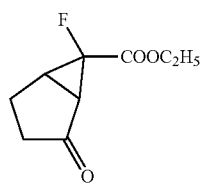

(IIA)

From the viewpoint that reduction in total yield is caused due to having a large number of reaction steps and lowering the production cost and shortening the production period are difficult to achieve, the synthetic route described above strongly requires an improvement. Further, since the conventional synthetic process needs to use sodium azide having potential explosion problem and to undergo a synthetic intermediate having an azide functional group with the same problem, it is necessary to use highly toxic osmium tetraoxide or carbon monoxide. Therefore, from the viewpoint of ensuring safety in preparation, an improved process is also in need.

Since the antagonist substance of group II metabotropic glutamate receptor that is represented by the formula (IA) as disclosed in Patent Document 1 is useful as a therapeutic agent, in relation to a process for producing the compound, a production process which has no safety problem like run away reaction, can be easily scaled up, uses a reagent that is safe and effective in terms of cost, is effective as having fewer number of reaction steps, and is appropriate for mass production is in need.

To solve all at once the problems of the conventional synthetic processes described above, the inventors of the present application found a novel synthetic route and a novel synthetic intermediate compound which allow the synthesis of the antagonist substance of group II metabotropic glutamate receptor, that is represented by the following formula (I), from an intermediate represented by the following formula (II) by performing only 5 to 6 reaction steps.

Specifically, the present invention relates to the followings;

(1) A process for producing a 3-alkoxy-2-amino-6-fluoro bicyclo[3.1.0]hexane-2,6-dicarboxylic acid derivative represented by the formula (I) or a salt thereof, which includes:

[Chemical Formula 3]

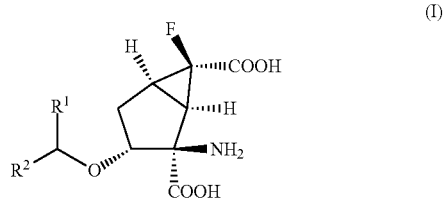

(I)

(in the formula (I), $R^1$ and $R^2$, which may be the same or different from each other, each represent a hydrogen atom, a $C_{1-10}$ alkyl group, a $C_{2-10}$ alkenyl group, a phenyl group, a naphthyl group, a naphthyl group substituted with 1 to 7 halogen atoms, a heteroaromatic group, or a phenyl group substituted with 1 to 5 substituent groups selected from a group consisting of a halogen atom, a $C_{1-10}$ alkyl group, a $C_{1-10}$ alkoxy group, a trifluoro methyl group, a phenyl group, a hydroxy carbonyl group, an amino group, a nitro group, a cyano group, and a phenoxy group. Further, $R^1$ and $R^2$ may bind to each other to form a cyclic structure), (A) converting a compound represented by the formula (II) or a salt thereof to a compound represented by the formula (III) or a salt thereof,

[Chemical Formula 4]

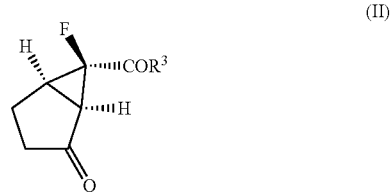

(II)

(in the formula (II), $R^3$ represents a $C_{1-6}$ alkoxy group, an amino group, or a hydroxyl group)

[Chemical Formula 5]

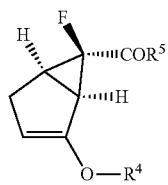
(III)

(in the formula (III), $R^4$ represents $-SiR^{41}R^{42}R^{43}$ wherein $R^{41}$, $R^{42}$, and $R^{43}$, which may be the same or different from each other, each represent a $C_{1-6}$ alkyl group. $R^5$ represents a $C_{1-6}$ alkoxy group, an amino group, or a hydroxyl group)

(B) converting the compound represented by the formula (III) or a salt thereof to a compound represented by the formula (IV) or a salt thereof,

[Chemical Formula 6]

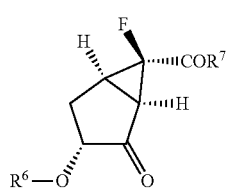
(IV)

(in the formula (IV), $R^6$ represents a hydrogen atom, a benzoyl group, a benzoyl group substituted with a halogen atom, or $-SiR^{61}R^{62}R^{63}$ wherein $R^{61}$, $R^{62}$, and $R^{63}$, which may be the same or different from each other, each represent a $C_{1-6}$ alkyl group. $R^7$ represents a $C_{1-6}$ alkoxy group, an amino group, or a hydroxyl group)

(C) converting the compound represented by the formula (IV) or a salt thereof to a compound represented by the formula (V) or a salt thereof,

[Chemical Formula 7]

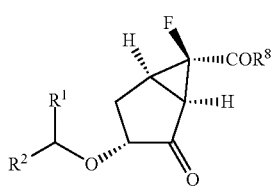
(V)

(in the formula (V), $R^1$ and $R^2$ are as defined in the above and $R^8$ represents a $C_{1-6}$ alkoxy group, an amino group, or a hydroxyl group)

(D) converting the compound represented by the formula (V) or a salt thereof to a compound represented by the formula (VI) or a salt thereof,

[Chemical Formula 8]

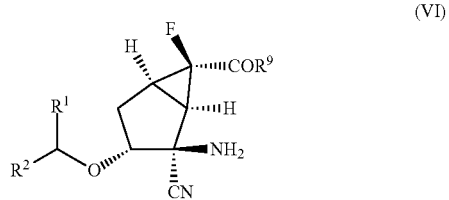
(VI)

(in the formula (VI), $R^1$ and $R^2$ are as defined in the above and $R^9$ represents a $C_{1-6}$ alkoxy group, an amino group, or a hydroxyl group), and (E) converting the compound represented by the formula (VI) or a salt thereof to the compound represented by the formula (I) or a salt thereof.

(2) A process for producing a 3-alkoxy-2-amino-6-fluoro bicyclo[3.1.0]hexane-2,6-dicarboxylic acid derivative represented by the formula (I) or a salt thereof, which includes converting a compound represented by the formula (VI) or a salt thereof to the compound represented by the formula (I) or a salt thereof

[Chemical Formula 9]

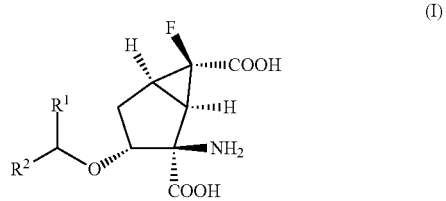
(I)

(in the formula (I), $R^1$ and $R^2$, which may be the same or different from each other, each represent a hydrogen atom, a $C_{1-10}$ alkyl group, a $C_{2-10}$ alkenyl group, a phenyl group, a naphthyl group, a naphthyl group substituted with 1 to 7 halogen atoms, a heteroaromatic group, or a phenyl group substituted with 1 to 5 substituent groups selected from a group consisting of a halogen atom, a $C_{1-10}$ alkyl group, a $C_{1-10}$ alkoxy group, a trifluoro methyl group, a phenyl group, a hydroxy carbonyl group, an amino group, a nitro group, a cyano group, and a phenoxy group. Further, $R^1$ and $R^2$ may bind to each other to form a cyclic structure),

[Chemical Formula 10]

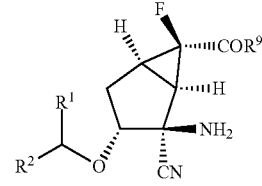
(VI)

(in the formula (VI), $R^1$ and $R^2$ are as defined in the above and $R^9$ represents a $C_{1-6}$ alkoxy group, an amino group, or a hydroxyl group).

(3) The process described in (1) or (2) above, wherein the converting the compound represented by the formula (VI) or a salt thereof to the compound represented by the formula (I) or a salt thereof includes following steps;

(F) converting the compound represented by the formula (VI) or a salt thereof to a compound represented by the formula (VII) or a salt thereof

[Chemical Formula 11]

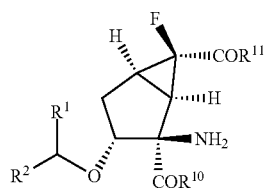

(VII)

(in the formula (VII), $R^1$ and $R^2$ are as defined in the above. $R^{10}$ represents a $C_{1-6}$ alkoxy group, an amino group or a hydroxyl group, and $R^{11}$ represents a $C_{1-6}$ alkoxy group, an amino group, or a hydroxyl group, with the proviso that $R^{10}$ and $R^{11}$ do not simultaneously represent a hydroxyl group), and (G) converting the compound represented by the formula (VII) or a salt thereof to the compound represented by the formula (I) or a salt thereof.

(4) A process for producing a 3-alkoxy-2-amino-6-fluoro bicyclo[3.1.0]hexane-2,6-dicarboxylic acid derivative represented by the formula (I) or a salt thereof, which includes:

[Chemical Formula 12]

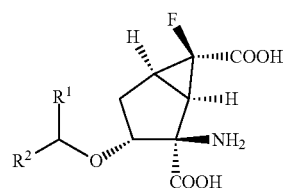

(I)

(in the formula (I), $R^1$ and $R^2$, which may be the same or different from each other, each represent a hydrogen atom, a $C_{1-10}$ alkyl group, a $C_{2-10}$ alkenyl group, a phenyl group, a naphthyl group, a naphthyl group substituted with 1 to 7 halogen atoms, a heteroaromatic group, or a phenyl group substituted with 1 to 5 substituent groups selected from a group consisting of a halogen atom, a $C_{1-10}$ alkyl group, a $C_{1-10}$ alkoxy group, a trifluoro methyl group, a phenyl group, a hydroxy carbonyl group, an amino group, a nitro group, a cyano group, and a phenoxy group. Further, $R^1$ and $R^2$ may bind to each other to form a cyclic structure), (A) converting a compound represented by the formula (II) or a salt thereof to a compound represented by the formula (III) or a salt thereof,

[Chemical Formula 13]

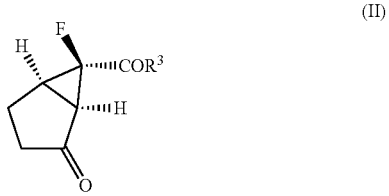

(II)

(in the formula (II), $R^3$ represents a $C_{1-6}$ alkoxy group, an amino group, or a hydroxyl group)

[Chemical Formula 14]

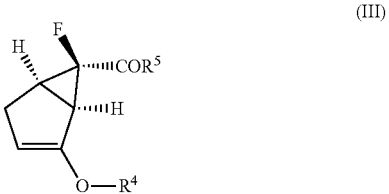

(III)

(in the formula (III), $R^4$ represents $-SiR^{41}R^{42}R^{43}$ wherein $R^{41}$, $R^{42}$, and $R^{43}$, which may be the same or different from each other, each represent a $C_{1-6}$ alkyl group. $R^5$ represents a $C_{1-6}$ alkoxy group, an amino group, or a hydroxyl group)

(B) converting the compound represented by the formula (III) or a salt thereof to a compound represented by the formula (IV) or a salt thereof,

[Chemical Formula 15]

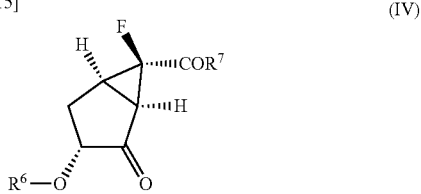

(IV)

(in the formula (IV), $R^6$ represents a hydrogen atom, a benzoyl group, a benzoyl group substituted with a halogen atom, or $-SiR^{61}R^{62}R^{63}$ wherein $R^{61}$, $R^{62}$, and $R^{63}$, which may be the same or different from each other, each represent a $C_{1-6}$ alkyl group. $R^7$ represents a $C_{1-6}$ alkoxy group, an amino group, or a hydroxyl group)

(C) converting the compound represented by the formula (IV) or a salt thereof to a compound represented by the formula (V) or a salt thereof,

[Chemical Formula 16]

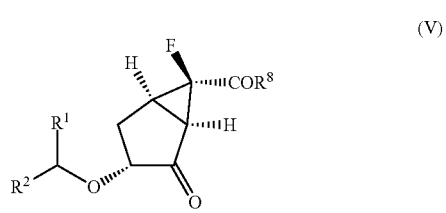

(V)

(in the formula (V), $R^1$ and $R^2$ are as defined in the above and $R^8$ represents a $C_{1-6}$ alkoxy group, an amino group, or a hydroxyl group)

(H) converting the compound represented by the formula (V) or a salt thereof to a compound represented by the formula (IX) or a salt thereof,

[Chemical Formula 17]

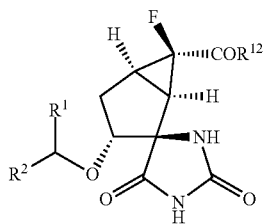

(IX)

(in the formula (IX), $R^1$ and $R^2$ are as defined in the above and $R^{12}$ represents a $C_{1-6}$ alkoxy group, an amino group, or a hydroxyl group), and (I) converting the compound represented by the formula (IX) or a salt thereof to the compound represented by the formula (I) or a salt thereof.

(5) A compound represented by the formula (IV) or a salt thereof

[Chemical Formula 18]

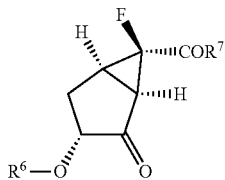

(IV)

(in the formula (IV), $R^6$ represents a hydrogen atom, a benzoyl group, a benzoyl group substituted with a halogen atom, or —$SiR^{61}R^{62}R^{63}$ wherein $R^{61}$, $R^{62}$, and $R^{63}$, which may be the same or different from each other, each represent a $C_{1-6}$ alkyl group. $R^7$ represents a $C_{1-6}$ alkoxy group, an amino group, or a hydroxyl group).

(6) A compound represented by the formula (V) or a salt thereof

[Chemical Formula 19]

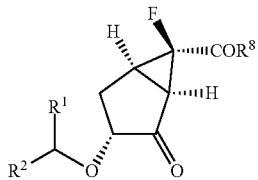

(V)

(in the formula (V), $R^1$ and $R^2$, which may be the same or different from each other, each represent a hydrogen atom, a $C_{1-10}$ alkyl group, a $C_{2-10}$ alkenyl group, a phenyl group, a naphthyl group, a naphthyl group substituted with 1 to 7 halogen atoms, a heteroaromatic group, or a phenyl group substituted with 1 to 5 substituent groups selected from a group consisting of a halogen atom, a $C_{1-10}$ alkyl group, a $C_{1-10}$ alkoxy group, a trifluoro methyl group, a phenyl group, a hydroxy carbonyl group, an amino group, a nitro group, a cyano group, and a phenoxy group. Further, $R^1$ and $R^2$ may bind to each other to form a cyclic structure. $R^8$ represents a $C_{1-6}$ alkoxy group, an amino group, or a hydroxyl group).

(7) A compound represented by the formula (VI) or a salt thereof

[Chemical Formula 20]

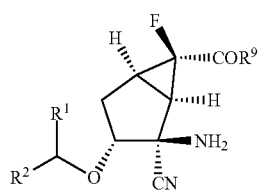

(VI)

(in the formula (VI), $R^1$ and $R^2$, which may be the same or different from each other, each represent a hydrogen atom, a $C_{1-10}$ alkyl group, a $C_{2-10}$ alkenyl group, a phenyl group, a naphthyl group, a naphthyl group substituted with 1 to 7 halogen atoms, a heteroaromatic group, or a phenyl group substituted with 1 to 5 substituent groups selected from a group consisting of a halogen atom, a $C_{1-10}$ alkyl group, a $C_{1-10}$ alkoxy group, a trifluoro methyl group, a phenyl group, a hydroxy carbonyl group, an amino group, a nitro group, a cyano group, and a phenoxy group. Further, $R^1$ and $R^2$ may bind to each other to form a cyclic structure. $R^9$ represents a $C_{1-6}$ alkoxy group, an amino group, or a hydroxyl group).

(8) A compound represented by the formula (VIII) or a salt thereof

[Chemical Formula 21]

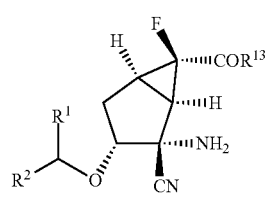

(VIII)

(in the formula (VIII), $R^1$ and $R^2$, which may be the same or different from each other, each represent a hydrogen atom, a $C_{1-10}$ alkyl group, a $C_{2-10}$ alkenyl group, a phenyl group, a naphthyl group, a naphthyl group substituted with 1 to 7 halogen atoms, a heteroaromatic group, or a phenyl group substituted with 1 to 5 substituent groups selected from a group consisting of a halogen atom, a $C_{1-10}$ alkyl group, a $C_{1-10}$ alkoxy group, a trifluoro methyl group, a phenyl group, a hydroxy carbonyl group, an amino group, a nitro group, a cyano group, and a phenoxy group. Further, $R^1$ and $R^2$ may bind to each other to form a cyclic structure. $R^{13}$ represents a $C_{1-6}$ alkoxy group, an amino group, or a hydroxyl group).

(9) A compound represented by the formula (VII) or a salt thereof

[Chemical Formula 22]

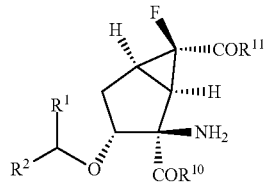

(VII)

(in the formula (VII), $R^1$ and $R^2$, which may be the same or different from each other, each represent a hydrogen atom, a $C_{1-10}$ alkyl group, a $C_{2-10}$ alkenyl group, a phenyl group, a naphthyl group, a naphthyl group substituted with 1 to 7 halogen atoms, a heteroaromatic group, or a phenyl group substituted with 1 to 5 substituent groups selected from a group consisting of a halogen atom, a $C_{1-10}$ alkyl group, a $C_{1-10}$ alkoxy group, a trifluoro methyl group, a phenyl group, a hydroxy carbonyl group, an amino group, a nitro group, a cyano group, and a phenoxy group. Further, $R^1$ and $R^2$ may bind to each other to form a cyclic structure. $R^{10}$ represents a $C_{1-6}$ alkoxy group, an amino group, or a hydroxyl group. $R^{11}$ represents a $C_{1-6}$ alkoxy group, an amino group, or a hydroxyl group, with the proviso that, $R^{10}$ and $R^{11}$ do not simultaneously represent a hydroxyl group and do not simultaneously represent a $C_{1-6}$ alkoxy group. When any one of $R^{10}$ and $R^{11}$ is a hydroxyl group, the other is not a $C_{1-6}$ alkoxy group).

(10) A compound represented by the formula (IX) or a salt thereof

[Chemical Formula 23]

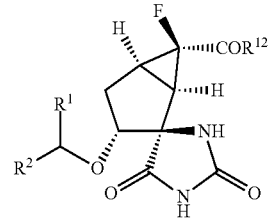

(IX)

(in the formula (IX), $R^1$ and $R^2$, which may be the same or different from each other, each represent a hydrogen atom, a $C_{1-10}$ alkyl group, a $C_{2-10}$ alkenyl group, a phenyl group, a naphthyl group, a naphthyl group substituted with 1 to 7 halogen atoms, a heteroaromatic group, or a phenyl group substituted with 1 to 5 substituent groups selected from a group consisting of a halogen atom, a $C_{1-10}$ alkyl group, a $C_{1-10}$ alkoxy group, a trifluoro methyl group, a phenyl group, a hydroxy carbonyl group, an amino group, a nitro group, a cyano group, and a phenoxy group. Further, $R^1$ and $R^2$ may bind to each other to form a cyclic structure. $R^{12}$ represents a $C_{1-6}$ alkoxy group, an amino group, or a hydroxyl group).

(11) A compound represented by the formula (X) or a salt thereof

[Chemical Formula 24]

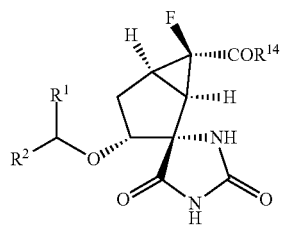

(X)

(in the formula (X), $R^1$ and $R^2$, which may be the same or different from each other, each represent a hydrogen atom, a $C_{1-10}$ alkyl group, a $C_{2-10}$ alkenyl group, a phenyl group, a naphthyl group, a naphthyl group substituted with 1 to 7 halogen atoms, a heteroaromatic group, or a phenyl group substituted with 1 to 5 substituent groups selected from a group consisting of a halogen atom, a $C_{1-10}$ alkyl group, a $C_{1-10}$ alkoxy group, a trifluoro methyl group, a phenyl group, a hydroxy carbonyl group, an amino group, a nitro group, a cyano group, and a phenoxy group. Further, $R^1$ and $R^2$ may bind to each other to form a cyclic structure. $R^{14}$ represents a $C_{1-6}$ alkoxy group, an amino group, or a hydroxyl group).

By using the production process of the present invention, synthesis of an antagonist substance of group II metabotropic glutamate receptor that is represented by the formula (I) can be obtained from the intermediate represented by the formula (II) with reduced number of reaction steps, that is, five to six reaction steps. At the same time, the total yield is significantly increased compared to conventional synthetic processes. In addition, not only the use of a sodium azide having potential explosion problem and the intervention of a synthetic intermediate containing an azide functional group with the same problem can be avoided, but also the use of highly toxic osmium tetraoxide or carbon monoxide can be avoided.

In other words, according to the production process of the present invention which has no safety problem like run away reaction, can be easily scaled up, uses a reagent that is safe and effective in terms of cost, is effective as having few number of reaction steps, and is appropriate for mass production compared to conventional synthetic processes, 3-alkoxy-2-amino-6-fluoro bicyclo[3.1.0]hexane-2,6-dicarboxylic acid derivative represented by the formula (I), which is an antagonist substance of group II metabotropic glutamate receptor, can be efficiently produced.

DESCRIPTION OF EMBODIMENTS

In the specification, the numerical range described with "-" or "to" includes the value of both ends, unless specifically described otherwise.

The "$C_{1-10}$ alkyl group" means a straight-chain alkyl group having one to ten carbon atoms, a branched chain alkyl group having three to ten carbon atoms or a cyclic alkyl group having three to ten carbon atoms.

Examples of the straight-chain alkyl group include a methyl group, an ethyl group, a propyl group, a butyl group, a pentyl group, a hexyl group, a heptyl group, an octyl group, a nonyl group and a decyl group.

Examples of the branched chain alkyl group include an isopropyl group, an isobutyl group, a 1-methyl propyl group, a tert-butyl group, a 1-methyl butyl group, a 2-methyl butyl group, a 3-methyl butyl group, a 1-ethyl propyl group, a 1,1-dimethyl propyl group, a 2,2-dimethyl propyl group, a 1,2-dimethyl propyl group, a 1-methyl pentyl group, a 2-methyl pentyl group, a 3-methyl pentyl group, a 4-methyl pentyl group, a 1-ethyl butyl group, a 2-ethyl butyl group, a 1,1-dimethyl butyl group, a 1,2-dimethyl butyl group, a 1,3-dimethyl butyl group, a 2,2-dimethyl butyl group, a 2,3-dimethyl butyl group, a 3,3-dimethyl butyl group, a 5-methyl hexyl group, a 3-ethyl pentyl group, a 1-propyl butyl group, a 1,4-dimethyl pentyl group, a 3,4-dimethyl pentyl group, a 1,2,3-trimethyl butyl group, a 1-isopropyl butyl group, a 4,4-dimethyl pentyl group, a 5-methyl heptyl group, a 6-methyl heptyl group, a 4-ethyl hexyl group, a 2-propyl pentyl group, a 2,5-dimethyl hexyl group, a 4,5-dimethyl hexyl group, a 2-ethyl-3-methyl pentyl group, a 1,2,4-trimethyl pentyl group, a 2-methyl-1-isopropyl butyl group, a 3-methyl octyl group, a 2,5-dimethyl heptyl group, a 1-(1-methyl propyl)-2-methyl butyl group, a 1,4,5-trimethyl hexyl group, a 1,2,3,4-tetramethyl pentyl group, a 7-methyl octyl group, a 6-methyl nonyl group, a 8-methyl nonyl group, a 5-ethyl-2-methyl heptyl group, a 2,3-dimethyl-1-(1-methyl propyl)butyl group, a cyclopropyl methyl group, a 2-(cyclopropyl)ethyl group, a 3,7-dimethyl octyl group, a 3-(cyclobutyl)pentyl group, a cyclopentyl methyl group, and a cyclohexyl methyl group.

Examples of the cyclic alkyl group include a cyclopropyl group, a cyclobutyl group, a cyclopentyl group, a cyclohexyl group, a cycloheptyl group, and a cyclooctyl group.

The "$C_{2-10}$ alkenyl group" means a straight-chain alkenyl group having two to ten carbon atoms, a branched chain alkenyl group having three to ten carbon atoms or a cyclic alkenyl group having five to ten carbon atoms, all with at least one double bond, and examples of which include a vinyl group, an allyl group, a 3-butenyl group, a 4-pentenyl group, a 5-hexenyl group, a 6-heptenyl group, a 7-octenyl group, a 8-nonenyl group, a 9-decenyl group, a 1-methyl-2-butenyl group, a 2-methyl-2-butenyl group, a 2-methyl-3-butenyl group, a 2-pentenyl group, a 2-methyl-2-hexenyl group and a 2-cyclopentenyl group.

The "naphthyl group substituted with one to seven halogen atoms" means a naphthyl group which is substituted with the same or different one to seven fluorine atom, chlorine atom, bromine atom or iodine atom, and examples of which include a 1-fluoro-2-naphthyl group, a 2-fluoro-1-naphthyl group, a 1-chloro-2-naphthyl group, a 2-chloro-1-naphthyl group, a 1-bromo-2-naphthyl group, a 2-bromo-1-naphthyl group, a 1-iodo-2-naphthyl group, a 2-iodo-1-naphthyl group, and a 1,3-difluoro-2-naphthyl group.

The "heteroaromatic group" means a monocyclic aromatic 5 membered or 6 membered ring containing at least one atom selected from an oxygen atom, a nitrogen atom or a sulfur atom; a monocyclic ring such as above which is fused with a benzene ring; or a bicyclic aromatic ring which is fused with one another. Examples of the hetero aromatic group include furyl, pyrrolyl, thiophenyl, oxazolyl, isoxazolyl, imidazolyl, pyrazolyl, thiazolyl, isothiazolyl, oxadiazolyl, thiadiazolyl, benzofuranyl, indolyl, benzothiophenyl, indazolyl, benzoisooxazolyl, benzoisothiazolyl, benzoimidazolyl, benzooxazolyl, benzothiazolyl, pyridinyl, quinolynyl, isoquinolynyl, pyridazinyl, pyrimidinyl, pyrazinyl, cinnolinyl, phthalazinyl, quinazolinyl, and quinoxalinyl.

The "$C_{1-10}$ alkoxy group" means a straight-chain or branched chain alkoxy group having one to ten carbon atoms, and examples of which include a methoxy group, an ethoxy group, a propoxy group, an isopropoxy group, a butoxy group, an isobutoxy group, a tert-butoxy group, a pentyloxy group and an isopentyloxy group.

The "phenyl group substituted with one to five substituent groups selected from a group consisting of a halogen atom, a phenyl group, a $C_{1-10}$ alkyl group, a $C_{1-10}$ alkoxy group, a trifluoromethyl group, a phenyl group, a hydroxycarbonyl group, an amino group, a nitro group, a cyano group and a phenoxy group" means a phenyl group substituted with one to five substituent groups selected from a fluorine atom, a chlorine atom, a bromine atom, an iodine atom, a $C_{1-10}$ alkyl group, a cyclic $C_{3-10}$ alkyl group, a $C_{1-10}$ alkoxy group, a cyclic $C_{3-10}$ alkoxy group, a trifluoromethyl group, a phenyl group, a hydroxycarbonyl group, an amino group, a nitro group, a cyano group, or a phenoxy group.

Examples of the phenyl group substituted with one substituent group include a 2-fluoro phenyl group, a 3-fluoro phenyl group, a 4-fluoro phenyl group, a 2-chloro phenyl group, a 3-chloro phenyl group, a 4-chloro phenyl group, a 2-bromo phenyl group, a 3-bromo phenyl group, a 4-bromo phenyl group, a 2-iodo phenyl group, a 3-iodo phenyl group, a 4-iodo phenyl group, a 2-methyl phenyl group, a 3-methyl phenyl group, a 4-methyl phenyl group, a 2-ethyl phenyl group, a 3-ethyl phenyl group, a 4-ethyl phenyl group, a 2-isopropyl phenyl group, a 3-isopropyl phenyl group, a 4-isopropyl phenyl group, a 2-cyclopropyl phenyl group, a 3-cyclopropyl phenyl group, a 4-cyclopropyl phenyl group, a 2-cyclohexyl phenyl group, a 3-cyclohexyl phenyl group, a 4-cyclohexyl phenyl group, a 2-methoxy phenyl group, a 3-methoxy phenyl group, a 4-methoxy phenyl group, a 2-isopropoxy phenyl group, a 3-isopropoxy phenyl group, a 4-isopropoxy phenyl group, a 2-cyclobutyloxy phenyl group, a 3-cyclobutyloxy phenyl group, a 4-cyclobutyloxy phenyl group, a 2-cyclohexyl oxy phenyl group, a 3-cyclohexyl oxy phenyl group, a 4-cyclohexyl oxy phenyl group, a 2-trifluoro methyl phenyl group, a 3-fluoro methyl phenyl group, a 4-trifluoro methyl phenyl group, a 2-phenyl phenyl group, a 3-phenyl phenyl group, a 4-phenyl phenyl group, a 2-hydroxy carbonyl phenyl group, a 3-hydroxy carbonyl phenyl group, a 4-hydroxy carbonyl phenyl group, a 2-amino phenyl group, a 3-amino phenyl group, a 4-amino phenyl group, a 2-nitro phenyl group, a 3-nitro phenyl group, a 4-nitro phenyl group, a 2-cyano phenyl group, a 3-cyano phenyl group, a 4-cyano phenyl group, a 2-phenoxy phenyl group, a 3-phenoxy phenyl group, and a 4-phenoxy phenyl group.

Examples of the phenyl group substituted with two substituent groups include a 2,3-difluoro phenyl group, a 2,4-difluoro phenyl group, a 2,5-difluoro phenyl group, a 2,6-difluoro phenyl group, a 3,4-difluoro phenyl group, a 3,5-difluoro phenyl group, a 2,3-dichloro phenyl group, a 2,4-dichloro phenyl group, a 2,5-dichloro phenyl group, a 2,6-dichloro phenyl group, a 3,4-dichloro phenyl group, a 3,5-dichloro phenyl group, a 2,3-dibromo phenyl group, a 2,4-dibromo phenyl group, a 2,5-dibromo phenyl group, a 2,6-dibromo phenyl group, a 3,4-dibromo phenyl group, a 3,5-dibromo phenyl group, a 2,3-diiodo phenyl group, a 2,4-diiodo phenyl group, a 2,5-diiodo phenyl group, a 2,6-diiodo phenyl group, a 3,4-diiodo phenyl group, a 3,5-diiodo phenyl group, a 3-chloro-4-fluoro phenyl group, a 4-chloro-3-fluoro phenyl group, a 3-bromo-4-fluoro phenyl group, a 4-bromo-3-fluoro phenyl group, a 4-bromo-3-chloro phenyl group, a 3-bromo-4-chloro phenyl group, a 3-chloro-4-methyl phenyl group, a 4-chloro-3-methyl phenyl group, a 3-fluoro-4-methyl phenyl group, a 4-fluoro-3-methyl phenyl group, a 3-fluoro-4-methoxy phenyl group, a 4-fluoro-3-methoxy phenyl group, a 3-bromo-4-methoxy phenyl group, a 4-bromo-3-methoxy phenyl group, a 3-chloro-4-phenoxy phenyl group, a 4-chloro-3-phenoxy phenyl group, a 3-chloro-4-nitro phenyl group, a 4-chloro-3-nitro phenyl group, a 4-bromo-3-nitro phenyl group, a 3-bromo-4-nitro phenyl group, a 3-amino-4-bromo phenyl group, a 4-amino-3-bromo phenyl group, a 3-bromo-4-hydroxy carbonyl group, a 4-bromo-3-hydroxy carbonyl phenyl group, a 4-fluoro-3-hydroxy carbonyl phenyl group, a 3-fluoro-4-hydroxy carbonyl phenyl group, a 4-fluoro-3-hydroxy carbonyl phenyl group, a 3-cyano-4-fluoro phenyl group, a 3-cyano-4-fluoro phenyl group, a 4-cyano-3-methyl phenyl group, a 3-cyano-4-methyl phenyl group, a 3-cyano-4-methoxy phenyl group, and a 4-cyano-3-methoxy phenyl group.

Examples of the phenyl group substituted with three substituent groups include a 2,3,4-trifluorophenyl group, a 3,4,5-trifluorophenyl group, a 3,4,5-trichlorophenyl group, a 3-chloro-2,6-difluorophenyl group, a 3,5-dichloro-4-methoxyphenyl group, and a 3,5-dibromo-4-methoxyphenyl group.

Examples of the phenyl group substituted with four substituent groups include a 2,5-dibromo-3,4-dimethoxyphenyl group, and a 3,4-dibromo-2,4-dimethoxyphenyl group.

Examples of the phenyl group substituted with five substituent groups include a 2,3,4,5,6-pentafluorophenyl group.

The term "form wherein $R^1$ and $R^2$ bind to each other to form a cyclic structure" includes form to have a cyclopropyl group, a cyclobutyl group, a cyclopentyl group, a cyclohexyl group, a cycloheptyl group, a cyclooctyl group, a cyclopentenyl group, a cyclohexenyl group, a cycloheptenyl group, a cyclooctenyl group, an oxa cyclobutyl group, an oxa cyclopentyl group, an oxa cyclohexyl group, an oxa cycloheptyl group, an oxa cyclooctyl group, an azacyclobutyl group, an azacyclopentyl group, an azacyclohexyl group, an azacycloheptyl group, or an azacyclooctyl group.

The "$C_{1-6}$ alkoxy group" means a straight-chain alkoxy group having one to six carbon atoms, a branched chain alkoxy group having three to six carbon atoms, or a cyclic alkoxy group having three to six carbon atoms, and examples of which include a methoxy group, an ethoxy group, a propoxy group, a butoxy group, a pentyloxy group, a hexyloxy group, an isopropoxy group, an iso butoxy group, a 1-methyl propoxy group, a tert-butoxy group, a 1-methyl butoxy group, a 2-methyl butoxy group, an isopentyl oxy group, a neopentyl oxy group, a 1,1-dimethyl propoxy group, a 1,2-dimethyl propoxy group, a 1-methyl pentyloxy group, a 2-methyl pentyloxy group, a 3-methyl pentyloxy group, an iso hexyloxy group, a 1-ethyl butoxy group, a 2-ethyl butoxy group, a 1,1-dimethyl butoxy group, a 1,2-dimethyl butoxy group, a 1,3-dimethyl butoxy group, a 2,2-dimethyl butoxy group, a 2,3-dimethyl butoxy group, a 3,3-dimethyl butoxy group, a cyclopropyl oxy group, a cyclobutyl oxy group, a cyclopentyl oxy group, and a cyclohexyl oxy group.

The "$C_{1-6}$ alkyl group" means a straight-chain alkyl group having one to six carbon atoms, a branched chain alkyl group having three to six carbon atoms, or a cyclic alkyl group having three to six carbon atoms, and examples of which include a methyl group, an ethyl group, a propyl group, a butyl group, a pentyl group, a hexyl group, an isopropyl group, an isobutyl group, a 1-methyl propyl group, a tert-butyl group, a 1-methyl butyl group, a 2-methyl butyl group, an isopentyl group, a neopentyl group, a 1,1-dimethyl propyl group, a 1,2-dimethyl propyl group, a 1-methyl pentyl group, a 2-methyl pentyl group, a 3-methyl pentyl group, an iso hexyl group, a 1-ethyl butyl group, a 2-ethyl butyl group, a 1,1-dimethyl butyl group, a 1,2-dimethyl butyl group, a 1,3-dimethyl butyl group, a 2,2-dimethyl butyl group, a 2,3-dimethyl butyl group, a 3,3-dimethyl butyl group, a cyclopropyl group, a cyclobutyl group, a cyclopentyl group, and a cyclohexyl group.

The "benzoyl group substituted with a halogen atom" means a benzoyl group substituted with at least one fluorine atom, a chlorine atom, a bromine atom, or an iodine atom. Examples thereof include a 3-chloro benzoyl group, a 4-fluoro benzoyl group, a 4-bromo benzoyl group, and a 4-iodo benzoyl group.

The "salt" includes, for example, a salt with an inorganic acid such as hydrochloric acid, hydrobromic acid, sulfuric acid, nitric acid, phosphoric acid, or boric acid, a salt with an organic acid such as formic acid, acetic acid, propionic acid, 2-ethyl hexanoic acid, trifluoroacetic acid, trichloroacetic acid, pyruvic acid, diphenyl acetic acid, cinnamic acid, glycolic acid, D-lactic acid, L-lactic acid, D-mandelic acid, L-mandelic acid, D-glucuronic acid, D-gluconic acid, lactobionic acid, oxalic acid, malonic acid, succinic acid, glutaric acid, adipic acid, fumaric acid, maleic acid, (+)-camphoric acid, 2-ketoglutaric acid, glutamic acid, asparaginic acid, pyroglutamic acid, D-tartaric acid, L-tartaric acid, D-malic acid, L-malic acid, citric acid, benzoic acid, 4-hydroxybenzoic acid, salicylic acid, phthalic acid, isophthalic acid, terephthalic acid, methane sulfonic acid, trifluoromethane sulfonic acid, ethane sulfonic acid, benzene sulfonic acid, p-toluene sulfonic acid, (+)-10-camphor sulfonic acid, (−)-10-camphor sulfonic acid, and isethionic acid;

a salt with one or more types of metal ions such as lithium ion, sodium ion, potassium ion, magnesium ion, calcium ion, barium ion, zinc ion, or aluminum ion;

a salt with an amine such as ammonia, triethyl amine, trimethyl amine, diethyl amine, morpholine, N-methyl morpholine, piperidine, piperazine, pyrrolidine, dicyclohexyl amine, 4-phenyl cyclohexyl amine, 2-amino ethanol, arginine, lysine, or N, N'-dibenzyl ethylene diamine, and;

a salt with quaternary ammonium ion such as tetramethyl ammonium ion, tetraethyl ammonium ion, tetrabutyl ammonium ion, or choline.

The "inert solvent" specifically indicates a solvent that is not involved with a target reaction.

A specific example of the combination of $R^1$ and $R^2$ in the compound represented by the formula (I) or a salt thereof in the present invention include a combination wherein one of $R^1$ and $R^2$ is a hydrogen atom and the other is a phenyl group substituted with 1 to 5 halogen atoms like a 3,4-dichloro phenyl group.

In a preferred embodiment of the process for producing a compound represented by the formula (I) or a salt thereof in the present invention, the compound represented by the formula (II) or a salt thereof is used as a starting material. Preferably, $R^3$ is a methoxy group or an ethoxy group. More preferably, $R^3$ is an ethoxy group.

In a preferred embodiment of the process for producing a compound represented by the formula (I) or a salt thereof in the present invention, specifically in a combination of substituent group in a compound represented by the formula (III) as an intermediate or a salt thereof, $R^4$ is a trimethylsilyl group or a triethyl silyl group and $R^5$ is a methoxy group or an ethoxy group. More preferably, $R^4$ is a trimethylsilyl group and $R^5$ is an ethoxy group.

In a preferred embodiment of the process for producing a compound represented by the formula (I) or a salt thereof in the present invention, specifically in a combination of substituent group in a compound represented by the formula (IV) as an intermediate or a salt thereof, $R^6$ is a hydrogen atom, a benzoyl group, a benzoyl group substituted with a halogen atom, or —$SiR^{61}R^{62}R^{63}$ wherein $R^{61}$, $R^{62}$, and $R^{63}$, which may be the same or different from each other, each represent a $C_{1-6}$ alkyl group, and $R^7$ is a methoxy group or an ethoxy group. More preferably, $R^6$ is a hydrogen atom and $R^7$ is an ethoxy group.

In a preferred embodiment of the process for producing a compound represented by the formula (I) or a salt thereof in the present invention, specifically in a combination of substituent group in a compound represented by the formula (V) as an intermediate or a salt thereof, $R^8$ is a methoxy group, an ethoxy group, or an amino group, $R^1$ is a hydrogen atom and $R^2$ is a 3,4-dichloro phenyl group. More preferably, $R^8$ is an ethoxy group or an amino group.

In a preferred embodiment of the process for producing a compound represented by the formula (I) or a salt thereof in the present invention, specifically in a combination of substituent group in a compound represented by the formula (VI) as an intermediate or a salt thereof, $R^9$ is a methoxy group, an ethoxy group or an amino group, $R^1$ is a hydrogen atom, and $R^2$ is a 3,4-dichloro phenyl group. More preferably, $R^9$ is an amino group.

In a combination of substituent group in a compound represented by the formula (VIII) or a salt thereof, which is a diastereomer of the compound represented by the formula (VI) or a salt thereof, it is preferable that $R^{13}$ is a methoxy group, an ethoxy group or an amino group, $R^1$ is a hydrogen atom, and $R^2$ is a 3,4-dichloro phenyl group. More preferably, $R^{13}$ is an amino group.

Further, preferred examples of a salt of the compound represented by the formula (VI) or the formula (VIII) include a salt with an organic acid like citric acid, L-tartaric acid, oxalic acid, and p-toluene sulfonic acid.

In a preferred embodiment of the process for producing a compound represented by the formula (I) or a salt thereof in the present invention, specifically in a combination of substituent group in a compound represented by the formula (VII) as an intermediate or a salt thereof, $R^{10}$ is an amino group, a hydroxyl group, a methoxy group or an ethoxy group, $R^{11}$ is an amino group, a hydroxyl group, a methoxy group or an ethoxy group, $R^1$ is an a hydrogen atom, and $R^2$ is a 3,4-dichloro phenyl group (with the proviso that $R^{10}$ and $R^{11}$ are not simultaneously a hydroxyl group). More preferably, $R^{10}$ is an amino group and $R^{11}$ is an amino group or a hydroxyl group.

In a preferred embodiment of the process for producing a compound represented by the formula (I) or a salt thereof in the present invention, a compound represented by the formula (VI) or a salt thereof is used as a starting material. In a combination of substituent group, it is preferable that $R^9$ is a methoxy group, an ethoxy group, or an amino group, $R^1$ is a hydrogen atom and $R^2$ is a 3,4-dichloro phenyl group. More preferably, $R^9$ is an amino group.

In a preferred embodiment of the process for producing a compound represented by the formula (I) or a salt thereof in the present invention, specifically in a combination of substituent group in a compound represented by the formula (IX) as an intermediate or a salt thereof, $R^{12}$ is an amino group, a hydroxyl group, a methoxy group or an ethoxy group, $R^1$ is an a hydrogen atom, and $R^2$ is a 3,4-dichloro phenyl group. More preferably, $R^{12}$ is a hydroxyl group.

In a combination of substituent group in a compound represented by the formula (X) or a salt thereof, which is a diastereomer of the compound represented by the formula (IX) or a salt thereof, it is preferable that $R^{14}$ is an amino group, a hydroxyl group, a methoxy group or an ethoxy group, $R^1$ is a hydrogen atom, and $R^2$ is a 3,4-dichloro phenyl group. More preferably, $R^{14}$ is a hydroxyl group.

The present invention relates to a process for producing a compound represented by the formula (I) or a salt thereof, that is, a process for producing the compound represented by the formula (I) or a salt thereof starting from a compound represented by the formula (II) or a salt thereof with the intervention of a compound represented by the formula (VI) or a salt thereof as an intermediate, a process for producing the compound represented by the formula (I) or a salt thereof starting from the compound represented by the formula (VI) or a salt thereof as an intermediate, and a process for producing the compound represented by the formula (I) or a salt thereof starting from the compound represented by the formula (II) or a salt thereof with the intervention of a compound represented by the formula (IX) or a salt thereof as an intermediate. The invention also relates to a compound represented by the formula (IV), the formula (V), the formula (VI), the formula (VII), the formula (VIII), the formula (IX), or the formula (X) and a salt thereof, which is a synthetic intermediate of the compound of the formula (I).

The invention can be carried out according to the process described below. One embodiment of the present invention is shown in the following Scheme 1, Scheme 2, and Scheme 3.

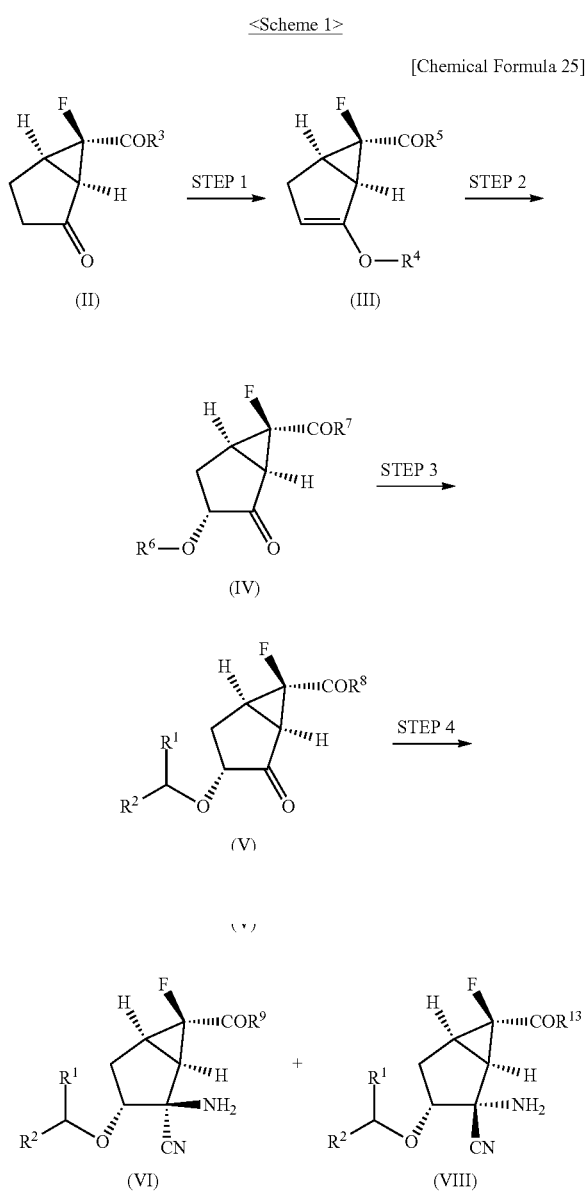

-continued

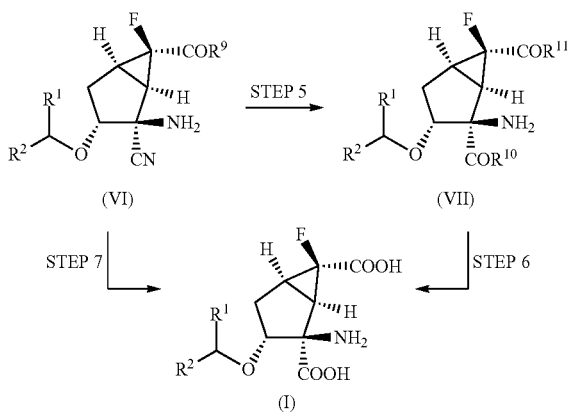

In the formulae of the Scheme 1 above, $R^1$, $R^2$, $R^3$, $R^4$, $R^5$, $R^6$, $R^7$, $R^8$, $R^9$, $R^{10}$, $R^{11}$, and $R^{13}$ areas defined above.

The compound represented by the formula (II) as a starting material can be produced according to the processes described in literatures (reference literatures: Org. Lett., 6, 3775-3777 (2004), J. Med. Chem., 43, 4893-4909 (2000), Org. Biomol. Chem., 2, 168-174 (2004), Tetrahedron, 57, 7487-7493 (2001), and the pamphlet of International Publication No. WO 02/00595).

(Step 1): A compound represented by the formula (III) is obtained by reacting a compound represented by the formula (II) with a silylating agent in an inert solvent in the presence of a base.

Examples of the inert solvent that can be used include hydrocarbon type solvents such as toluene, xylene, benzene, heptane, hexane, or petroleum ether;

halogen type solvents such as dichloro methane, chloroform, 1,2-dichloro ethane, carbon tetrachloride, chloro benzene, or benzotrifluoride;

ether type solvents such as tetrahydrofuran, 2-methyl tetrahydrofuran, tetrahydropyran, diethyl ether, diisopropyl ether, tert-butyl methyl ether, cyclopentyl methyl ether, 1,2-dimethoxy ethane, diethoxy methane, or 1,4-dioxane;

acetonitrile, N,N-dimethylformamide, N-methylpyrrolidone, dimethyl sulfoxide (DMSO), or a mixture of these solvents.

Examples of the base that can be used include an organic amine like triethyl amine, diisopropyl ethyl amine, N-methyl morpholine, diazabicycloundecene, diazabicyclononene, and pyridine, a metal amide base like lithium diisopropyl amide, lithium hexamethyl disilazide, sodium hexamethyl disilazide, and potassium hexamethyl disilazide, and an alkali metal hydride base like sodium hydride and potassium hydride.

Examples of the silylating agent that can be used include chloro trimethyl silane, bromo trimethyl silane, iodo trimethyl silane, trimethyl silyl trifluoro methane sulfonic acid, chloro triethyl silane, chloro triisopropyl silane, and tert-butyl chloro dimethyl silane. Further, as an additive for a combination with chloro trimethyl silane, sodium iodide, potassium iodide, tetrabutyl ammonium iodide, sodium bromide, and potassium bromide can be used.

The reaction temperature may be usually from −80° C. to the boiling point of the solvent used, is preferably in the range of −60° C. to 100° C., and is more preferably in the range of 0° C. to 60° C.

The amount of base that can be used may be in the range of 0.5 to 5 molar equivalents relative to the compound represented by the formula (II) as a raw material, preferably in the range of 1 to 3 molar equivalents, and more preferably in the range of 1 to 1.5 molar equivalents.

The amount of silylating agent that can be used may be in the range of 1 to 5 molar equivalents relative to the compound represented by the formula (II) as a raw material, preferably in the range of 1 to 3 molar equivalents, and more preferably in the range of 1 to 1.5 molar equivalents.

With regard to the amount of reaction solvent, it may be used at 1 to 100 times by mass relative to the compound represented by the formula (II) as a raw material, preferably in the range of 1 to 30 times by mass, and more preferably in the range of 1 to 10 times by mass.

The compound represented by the formula (III) may be used as a raw material for next step without purifying concentrated residues after the post-reaction treatment or concentrating the solution after post-treatment (reference literature: J. Med. Chem., 43, 4893-4909 (2000) and Bioorg. Med. Chem., 10, 433-436 (2002)).

(Step 2): A compound represented by the formula (IV) is obtained by reacting a compound represented by the formula (III) with an oxidizing agent in an inert solvent in the presence or absence of an additive.

Herein, by reacting in a solvent like methanol and ethanol in the presence of a base like potassium carbonate, sodium carbonate, sodium hydrogen carbonate, and potassium hydrogen carbonate, the compound represented by the formula (IV) of the present invention wherein $R^6$ is a benzoyl group or a benzoyl group substituted with a halogen atom can be converted into the compound represented by the formula (IV) of the present invention wherein $R^6$ is a hydrogen atom.

Further, by treating under acidic condition (dilute hydrochloric acid, aqueous solution of acetic acid, or the like) or basic condition (potassium carbonate, tetrabutyl ammonium fluoride, or the like), the compound represented by the formula (IV) of the present invention wherein $R^6$ is —SiR$^{61}$R$^{62}$R$^{63}$ (R$^{61}$, R$^{62}$, and R$^{63}$, which may be the same or different from each other, each represent a $C_{1-6}$ alkyl group) can be converted into the compound represented by the formula (IV) of the present invention wherein $R^6$ is a hydrogen atom.

Further, in the oxidation reaction of the compound represented by the formula (III), by treating under post-treatment condition (acid treatment, base treatment, or treatment with aqueous solution of sodium thiosulfate, aqueous solution of sodium sulfite, or aqueous solution of sodium hydrogen sulfite), the compound represented by the formula (IV) of the present invention wherein $R^6$ is —SiR$^{61}$R$^{62}$R$^{63}$ (R$^{61}$, R$^{62}$, and R$^{63}$, which may be the same or different from each other, each represent a $C_{1-6}$ alkyl group), that is produced together with the compound represented by the formula (IV) of the present invention wherein $R^6$ is a hydrogen atom, can be converted into the compound represented by the formula (IV) of the present invention wherein $R^6$ is a hydrogen atom.

Examples of the oxidizing agent that can be used include peracid like 3-chloro perbenzoic acid, perbenzoic acid, mono peroxy phthalic acid, magnesium salt of mono peroxy phthalic acid, and peracetic acid;

hydrogen peroxide in the presence of a catalyst like methyl trioxo rhenium or tris(cetyl pyridinium)peroxo tungstophosphate (PCWP);

hydrogen peroxide in the presence of a nitrile compound like trichloroacetonitrile and acetonitrile;

hydrogen peroxide in the presence of a nitrile compound like trichloroacetonitrile and acetonitrile and a ketone compound like acetone;

oxone ($2KHSO_5 \cdot KHSO_4 \cdot K_2SO_4$) in the presence of a ketone compound like acetone;

dimethyldioxirane, tert-butyl hydroperoxide, osmium tetraoxide, N-methyl morpholine-N-oxide, lead tetraacetate, iodosyl benzene and boron trifluoride diethyl ether complex, chromyl chloride, and ozone (reference literature: Organic Reactions, 62, 1-356 (2003)).

Examples of the inert solvent that can be used include hydrocarbon type solvents such as toluene, xylene, benzene, heptane, hexane, or petroleum ether;

halogen type solvents such as dichloro methane, chloroform, 1,2-dichloro ethane, carbon tetrachloride, chloro benzene, or benzotrifluoride;

ether type solvents such as tetrahydrofuran, 2-methyl tetrahydrofuran, tetrahydropyran, diethyl ether, diisopropyl ether, tert-butyl methyl ether, cyclopentyl methyl ether, 1,2-dimethoxy ethane, diethoxy methane, or 1,4-dioxane;

alcohol type solvents such as methanol, ethanol, 2-propanol, or tert-butyl alcohol;

ketone type solvents such as acetone, 2-butanone, or methyl isobutyl ketone;

ester type solvents such as ethyl acetate or isopropyl acetate;

acetonitrile, N,N-dimethylformamide, N-methylpyrrolidone, dimethyl sulfoxide, acetic acid, water, or a mixture of these solvents.

Examples of the additive include sodium hydrogen carbonate, potassium hydrogen carbonate, potassium carbonate, sodium carbonate, calcium hydroxide, potassium dihydrogen phosphate, dipotassium hydrogen phosphate, sodium dihydrogen phosphate, disodium hydrogen phosphate, pyridine, and acetic acid.

The reaction temperature may be usually from −80° C. to the boiling point of the solvent used, is preferably in the range of 0 to 100° C., and is more preferably in the range of 0 to 50° C.

The amount of oxidizing agent that can be used may be in the range of 0.5 to 5 molar equivalents relative to the compound represented by the formula (III) as a raw material, preferably in the range of 1 to 3 molar equivalents, and more preferably in the range of 1 to 1.5 molar equivalents.

The amount of the catalyst that can be used may be in the range of 0.001 to 0.5 molar equivalents relative to the compound represented by the formula (III) as a raw material, preferably in the range of 0.002 to 0.1 molar equivalents, and more preferably in the range of 0.01 to 0.05 molar equivalents.

With regard to the amount of solvent, it may be used at 1 to 100 times by mass relative to the compound represented by the formula (III) as a raw material, preferably in the range of 1 to 30 times by mass, and more preferably in the range of 1 to 10 times by mass.

Compound represented by the formula (IV) can be obtained as a purified product or unpurified product according to the process like chromatography, re-crystallization, re-slurry, neutralization crystal precipitation, and distillation.

(Step 3): A compound represented by the formula (V) of the present invention wherein $R^8$ is a $C_{1-6}$ alkoxy group is obtained by reacting a compound represented by the formula (IV) wherein $R^7$ is a $C_{1-6}$ alkoxy group and $R^6$ is a hydrogen atom with a compound represented by the formula $R^1R^2CHOC(=NH)CCl_3$ ($R^1$ and $R^2$ are as defined above) in an inert solvent in the presence of an acid (reference literature: J. Chem. Soc., Chem. Commun., 1240-1241 (1981) and J. Chem. Soc., Perkin Trans. 1, 2247-2250 (1985)).

Examples of the inert solvent that can be used include hydrocarbon type solvents such as toluene, xylene, benzene, heptane, hexane, cyclohexane, or petroleum ether;

halogen type solvents such as dichloro methane, chloroform, 1,2-dichloro ethane, carbon tetrachloride, chloro benzene, 1,2-dichlorobenzene, or benzotrifluoride;

ether type solvents such as tetrahydrofuran, 2-methyl tetrahydrofuran, tetrahydropyran, diethyl ether, diisopropyl ether, tert-butyl methyl ether, cyclopentyl methyl ether, 1,2-dimethoxy ethane, diethoxy methane, or 1,4-dioxane;

ketone type solvents such as acetone, 2-butanone, or methyl isobutyl ketone;

ester type solvents such as ethyl acetate or isopropyl acetate;

acetonitrile, N,N-dimethylformamide, N-methylpyrrolidone, dimethyl sulfoxide, or a mixture of these solvents.

Examples of the acid that can be used include Broensted acid like trifluoromethane sulfonic acid, bistrifluoro methane sulfonimide, trifluoro acetic acid, hydrochloric acid, and perchloric acid or Lewis acid like boron trifluoride.diethyl ether complex, zinc chloride, tin chloride, trifluoro methane sulfonic acid trimethyl silyl, scandium (III) trifluoro methane sulfonic acid, and ytterbium (III) trifluoro methane sulfonic acid.

The reaction temperature may be usually from −80° C. to the boiling point of the solvent used, is preferably in the range of −30 to 50° C., and is more preferably in the range of −10 to 20° C.

The amount of the compound represented by the formula $R^1R^2CHOC(=NH)CCl_3$ ($R^1$ and $R^2$ are as defined in the above) used may be in the range of 1 to 5 molar equivalents relative to the compound represented by the formula (IV) as a reacting compound, preferably in the range of 1 to 3 molar equivalents, and more preferably in the range of 1 to 1.5 molar equivalents.

The amount of acid that can be used may be in the range of 0.01 to 2 molar equivalents relative to the compound represented by the formula (IV) as a raw material, preferably in the range of 0.1 to 1.5 molar equivalents, and more preferably in the range of 0.3 to 1 molar equivalents.

With regard to the amount of solvent, it may be used at 1 to 100 times by mass relative to the compound represented by the formula (IV) as a raw material, preferably in the range of 1 to 30 times by mass, and more preferably in the range of 5 to 15 times by mass.

The compound represented by the formula $R^1R^2CHOC(=NH)CCl_3$ ($R^1$ and $R^2$ are as defined in the above) can be obtained by reacting an alcohol represented by the formula $R^1R^2CHOH$ with trichloroacetonitirle in the presence of a base according to a process described in the literature (reference literature: J. Chem. Soc., Perkin Trans. 1, 2247-2250 (1985) and Tetrahedron Lett., 37, 1481-1484 (1996)).

Further, by reacting the compound represented by the formula (IV) wherein $R^7$ is a $C_{1-6}$ alkoxy group and $R^6$ is a hydrogen atom with a compound represented by the formula $R^1R^2CHX$ ($R^1$ and $R^2$ are as defined in the above) in an inert solvent in the presence of a base, a compound represented by the formula (V) of the present invention wherein $R^8$ is a $C_{1-6}$ alkoxy group can be obtained. Herein, X represents a leaving group other than $OC(=NH)CCl_3$ and examples thereof include a chlorine atom, a bromine atom, an iodine atom, a p-toluene sulfonyl oxy group, a p-bromo benzene sulfonyl oxy group, a p-nitro benzene sulfonyl oxy group, a benzene sulfonyl oxy group, a methane sulfonyloxy group, and a trifluoro methane sulfonyl oxy group.

Examples of the inert solvent that can be used include hydrocarbon type solvents such as toluene, xylene, benzene, heptane, hexane, cyclohexane, cyclohexane, or petroleum ether;

halogen type solvents such as dichloro methane, chloroform, 1,2-dichloro ethane, carbon tetrachloride, chloro benzene, 1,2-dichloro benzene, or benzotrifluoride;

ether type solvents such as tetrahydrofuran, 2-methyl tetrahydrofuran, tetrahydropyran, diethyl ether, diisopropyl ether, tert-butyl methyl ether, cyclopentyl methyl ether, 1,2-dimethoxy ethane, diethoxy methane, or 1,4-dioxane;

ketone type solvents such as acetone, 2-butanone, or methyl isobutyl ketone;

ester type solvents such as ethyl acetate or isopropyl acetate;

acetonitrile, N,N-dimethylformamide, N-methylpyrrolidone, dimethyl sulfoxide, or a mixture of these solvents.

Examples of the base include inorganic bases like sodium hydride, potassium hydride, potassium carbonate, sodium carbonate, cesium carbonate, potassium hydrogen carbonate, sodium hydrogen carbonate, sodium hydroxide, potassium hydroxide, and silver (I) oxide;

metal amide bases like lithium diisopropyl amide, lithium hexamethyl disilazide, sodium hexamethyl disilazide, and potassium hexamethyl disilazide;

organic amine bases like triethyl amine, diisopropyl ethyl amine, N-methyl morpholine, diazabicycloundecene, diazabicyclononene, pyridine, and 4-dimethyl amino pyridine, and;

alkoxide bases like potassium tert-butoxide, sodium tert-pentoxide, and potassium tert-pentoxide.

The reaction temperature may be usually from −80° C. to the boiling point of the solvent used, is preferably in the range of −30 to 100° C., and is more preferably in the range of 0 to 50° C.

The amount of the compound represented by the formula $R^1R^2CHX$ ($R^1$, $R^2$ and X are as defined in the above) used may be in the range of 1 to 5 molar equivalents relative to the compound represented by the formula (IV) as a raw material, preferably in the range of 1 to 3 molar equivalents, and more preferably in the range of 1 to 1.5 molar equivalents.

The amount of base that can be used may be in the range of 1 to 5 molar equivalents relative to the compound represented by the formula (IV) as a raw material, preferably in the range of 1 to 3 molar equivalents, and more preferably in the range of 1 to 1.5 molar equivalents.

With regard to the amount of solvent, it may be used at 1 to 100 times by mass relative to the compound represented by the formula (IV) as a raw material, preferably in the range of 1 to 30 times by mass, and more preferably in the range of 5 to 15 times by mass.

Further, by reacting the compound represented by the formula (V) of the present invention wherein $R^8$ is a $C_{1-6}$ alkoxy group under a common condition for hydrolysis (reference literature: T. W. Greene, P. G. M. Wuts, "Protective Groups in Organic Synthesis"), a compound represented by the formula (V) of the present invention wherein $R^8$ is a hydroxyl group or a salt thereof can be obtained.

Further, by reacting the compound represented by the formula (V) of the present invention wherein $R^8$ is a $C_{1-6}$ alkoxy group with ammonia in an inert solvent, a compound represented by the formula (V) of the present invention wherein $R^8$ is an amino group can be obtained.

Examples of the inert solvent that can be used include alcohol type solvents such as methanol, ethanol, 2-propanol, or tert-butyl alcohol;

hydrocarbon type solvents such as toluene, xylene, benzene, heptane, hexane, cyclohexane, or petroleum ether;

halogen type solvents such as dichloro methane, chloroform, 1,2-dichloride ethane, carbon tetrachloride, chloro benzene, or benzotrifluoride;

ether type solvents such as tetrahydrofuran, 2-methyl tetrahydrofuran, tetrahydropyran, diethyl ether, diisopropyl ether, tert-butyl methyl ether, cyclopentyl methyl ether, 1,2-dimethoxy ethane, diethoxy methane, or 1,4-dioxane;

acetonitrile, N,N-dimethylformamide, N-methylpyrrolidone, dimethyl sulfoxide, or a mixture of these solvents.

The reaction temperature may be usually from −80° C. to the boiling point of the solvent used, is preferably in the range of −20 to 100° C., and is more preferably in the range of 0 to 50° C.

The amount of ammonia that can be used may be in the range of 1 to 100 molar equivalents relative to the compound represented by the formula (V) of the present invention wherein $R^8$ is a $C_{1-6}$ alkoxy group, preferably in the range of 5 to 50 molar equivalents, and more preferably in the range of 3 to 10 molar equivalents.

With regard to the amount of solvent, it may be used at 1 to 100 times by mass relative to the compound represented by the formula (IV) of the present invention wherein $R^8$ is a $C_{1-6}$ alkoxy group, preferably in the range of 1 to 30 times by mass, and more preferably in the range of 1 to 10 times by mass.

Compound represented by the formula (V) of the present invention can be obtained as a purified product or unpurified product according to the process like chromatography, re-crystallization, re-slurry, neutralization crystal precipitation, and distillation.

(Step 4): A compound represented by the formula (VI) of the present invention or a salt thereof and a compound represented by the formula (VIII) of the present invention or a salt thereof can be obtained by reacting the compound represented by the formula (V) with ammonia in an inert solvent in the presence of a Lewis acid followed by reaction with a cyanating agent in the presence or absence of a Lewis acid (reference literature: Tetrahedron Lett., 41, 6403-6406 (2000), Tetrahedron Lett., 42, 1499-1502 (2001), J. Org. Chem., 69, 843-856 (2004), J. Org. Chem., 70, 8027-8034 (2005), and Synlett, 1875-1878 (2006)).

Alternatively, the compound represented by the formula (VI) of the present invention or a salt thereof and the compound represented by the formula (VIII) of the present invention or a salt thereof can be obtained by reacting the compound represented by the formula (V) in an inert solvent with ammonia and a cyanating agent in the presence of a Lewis acid.

Examples of the inert solvent that can be used include alcohol type solvents such as methanol, ethanol, 2-propanol, tert-butyl alcohol, 2,2,2-trifluoro ethanol, or 1,1,1,3,3,3-hexafluoro-2-propanol;

hydrocarbon type solvents such as toluene, xylene, benzene, heptane, hexane, cyclohexane, or petroleum ether;

halogen type solvents such as dichloro methane, chloroform, 1,2-dichloro ethane, carbon tetrachloride, chloro benzene, or benzotrifluoride;

ether type solvents such as tetrahydrofuran, 2-methyl tetrahydrofuran, tetrahydropyran, diethyl ether, diisopropyl ether, tert-butyl methyl ether, cyclopentyl methyl ether, 1,2-dimethoxy ethane, diethoxy methane, or 1,4-dioxane; acetonitrile, N,N-dimethylformamide, N-methylpyrrolidone, dimethyl sulfoxide, acetic acid, water, or a mixture of these solvents.

Examples of the Lewis acid that can be used include titanium (IV) isopropoxide, titanium (IV) methoxide, titanium (IV) ethoxide, titanium (IV) propoxide, titanium (IV) butoxide, lithium bromide, lithium perchloric acid, magnesium bromide, magnesium bromide.diethyl ether complex, magnesium acetate, magnesium trifluoromethane sulfonic acid, magnesium perchloric acid, ferrocenium hexafluoro phosphate, cobalt (II) chloride, nickel (II) chloride, copper (II) trifluoromethane sulfonic acid, zinc chloride, zinc bromide, zinc iodide, zinc (II) trifluoromethane sulfonic acid, gallium (III) trifluoromethane sulfonic acid, niobium (V) chloride, molybdenum (VI) oxide, ruthenium (III) chloride, rhodium (III) iodide hydrate, indium (III) chloride, indium (III) bromide, indium (III) iodide, vanadyl triflate, tin chloride (II), tin (IV) chloride, iodine, hafnium (IV) trifluoromethane sulfonic acid, thallium (III) chloride, bismuth (III) chloride, scandium (III) trifluoromethane sulfonic acid, yttrium (III) trifluoromethane sulfonic acid, lanthanum (III) trifluoromethane sulfonic acid, lanthanum (III) isopropoxide, lanthanum (III) nitrate hexahydrate, cerium (III) chloride, praseodymium (III) trifluoromethane sulfonic acid, neodymium (III) trifluoromethane sulfonic acid, samarium (III) trifluoromethane sulfonic acid, gadolinium (III) trifluoromethane sulfonic acid, gadolinium (III) chloride hexahydrate, and ytterbium (III) trifluoromethane sulfonic acid.

Examples of the cyanating agent that can be used include trimethylsilyl cyanide, hydrogen cyanide, sodium cyanide, potassium cyanide, acetone cyanohydrin, diethylcyano phosphonate, diethyl aluminum cyanide, tert-butyl dimethyl silyl cyanide, and tributyl tin cyanide.

The reaction temperature may be usually from −80° C. to the boiling point of the solvent used. However, for the reaction between the compound represented by the formula (V) and ammonia, it is preferably in the range of 0 to 30° C. For the subsequent reaction with a cyanating agent, it is preferably in the range of −40 to 30° C. For the reaction between the compound represented by the formula (V) and ammonia and a cyanating agent, it is preferably in the range of −40 to 30° C.

The amount of ammonia that can be used may be in the range of 1 to 100 molar equivalents relative to the compound represented by the formula (V), preferably in the range of 5 to 50 molar equivalents, and more preferably in the range of 5 to 15 molar equivalents.

The amount of Lewis acid that can be used may be in the range of 0.01 to 10 molar equivalents relative to the compound represented by the formula (V), preferably in the range of 0.1 to 5 molar equivalents, and more preferably in the range of 0.1 to 2 molar equivalents.

The amount of cyanating agent that can be used may be in the range of 1 to 5 molar equivalents relative to the compound represented by the formula (V), preferably in the range of 1 to 3 molar equivalents, and more preferably in the range of 1 to 1.5 molar equivalents.

With regard to the amount of solvent, it may be used at 1 to 100 times by mass relative to the compound represented by the formula (V), preferably in the range of 1 to 30 times by mass, and more preferably in the range of 1 to 10 times by mass.

Further, the compound represented by the formula (VI) of the present invention or a salt thereof and the compound represented by the formula (VIII) of the present invention or a salt thereof can be obtained by reacting the compound represented by the formula (V) in an inert solvent with ammonia, ammonium salt, or a mixture of ammonia and ammonium salts, and a cyanating agent.

Examples of the inert solvent that can be used include alcohol type solvents such as methanol, ethanol, 2-propanol, tert-butyl alcohol, 2,2,2-trifluoro ethanol, or 1,1,1,3,3,3-hexafluoro-2-propanol;

hydrocarbon type solvents such as toluene, xylene, benzene, heptane, hexane, cyclohexane, or petroleum ether;

halogen type solvents such as dichloro methane, chloroform, 1,2-dichloro ethane, carbon tetrachloride, chloro benzene, or benzotrifluoride;

ether type solvents such as tetrahydrofuran, 2-methyl tetrahydrofuran, tetrahydropyran, diethyl ether, diisopropyl ether, tert-butyl methyl ether, cyclopentyl methyl ether, 1,2-dimethoxy ethane, diethoxy methane, or 1,4-dioxane;

acetonitrile, N,N-dimethylformamide, N-methylpyrrolidone, dimethyl sulfoxide, acetic acid, water, or a mixture of these solvents.

Examples of the ammonium salt that can be used include ammonium chloride, ammonium carbonate, ammonium hydrogen carbonate, ammonium formate, ammonium acetate, and ammonium carbamate.

Examples of the cyanating agent that can be used include trimethylsilyl cyanide, hydrogen cyanide, sodium cyanide, potassium cyanide, acetone cyanohydrin, diethylcyano phosphonate, diethyl aluminum cyanide, tert-butyl dimethyl silyl cyanide, and tributyl tin cyanide.

The reaction temperature may be usually from −80° C. to the boiling point of the solvent used, is preferably in the range of 0 to 100° C., and is more preferably in the range of 20 to 60° C.

The amount of ammonia that can be used may be in the range of 1 to 100 molar equivalents relative to the compound represented by the formula (V), preferably in the range of 5 to 50 molar equivalents, and more preferably in the range of 3 to 10 molar equivalents.

The amount of ammonium salt that can be used may be in the range of 1 to 10 molar equivalents relative to the compound represented by the formula (V), and preferably in the range of 2 to 5 molar equivalents.

The amount of cyanating agent that can be used may be in the range of 1 to 5 molar equivalents relative to the compound represented by the formula (V), preferably in the range of 1 to 3 molar equivalents, and more preferably in the range of 1 to 1.5 molar equivalents.

With regard to the amount of solvent, it may be used at 1 to 100 times by mass relative to the compound represented by the formula (V), preferably in the range of 1 to 30 times by mass, and more preferably in the range of 1 to 10 times by mass.

Further, by reacting the compound represented by the formula (VI) of the present invention wherein $R^9$ is a $C_{1-6}$ alkoxy group or an amino group or a salt thereof under a common condition for ester hydrolysis (reference literature: T. W. Greene, P. G. M. Wuts, "Protective Groups in Organic Synthesis"), or a common condition for carbamoyl group hydrolysis (reference literature: R. C. Larock, "Comprehensive Organic Transformations"), a compound represented by the formula (VI) of the present invention wherein $R^9$ is a hydroxyl group or a salt thereof can be obtained.

Similarly, by reacting the compound represented by the formula (VIII) of the present invention wherein $R^{13}$ is a $C_{1-6}$ alkoxy group or an amino group or a salt thereof under a common condition for ester hydrolysis (reference literature: T. W. Greene, P. G. M. Wuts, "Protective Groups in Organic Synthesis"), or a common condition for carbamoyl group hydrolysis (reference literature: R. C. Larock, "Comprehensive Organic Transformations"), a compound represented by the formula (VIII) of the present invention wherein $R^{13}$ is a hydroxyl group or a salt thereof can be obtained.

By reacting the compound represented by the formula (VI) of the present invention wherein $R^9$ is a $C_{1-6}$ alkoxy group or an amino group, the compound represented by the formula (VIII) of the present invention wherein $R^{13}$ is a $C_{1-6}$ alkoxy group or an amino group, or a mixture containing them at an arbitrary ratio with acid in an inert solvent, an acid salt of a compound represented by the formula (VI) of the present invention wherein $R^9$ is a $C_{1-6}$ alkoxy group or an amino group, an acid salt of a compound represented by the formula (VIII) of the present invention wherein $R^{13}$ is a $C_{1-6}$ alkoxy group or an amino group, or a mixture containing them at an arbitrary ratio can be obtained.

Further, by selecting a combination of a solvent and an acid, an acid salt of the compound represented by the formula (VI) of the present invention wherein $R^9$ is a $C_{1-6}$ alkoxy group or an amino group or an acid salt of the compound represented by the formula (VIII) of the present invention wherein $R^{13}$ is a $C_{1-6}$ alkoxy group or an amino group can be obtained as a solid with high purity from a mixture containing at an arbitrary ratio the compound represented by the formula (VI) of the present invention wherein $R^9$ is a $C_{1-6}$ alkoxy group or an amino group and the compound represented by the formula (VIII) of the present invention wherein $R^{13}$ is a $C_{1-6}$ alkoxy group or an amino group.

By appropriately selecting a combination of acid and solvent for the salt formation reaction described above, solubility difference in a solvent between an acid salt of the compound represented by the formula (VI) of the present invention and an acid salt of the compound represented by the formula (VIII) of the present invention can be increased. By utilizing such difference in solubility, an acid salt of the compound represented by the formula (VI) of the present invention can be obtained as a highly pure solid (crystal) by performing a simple filtration process only. Alternatively, it is also possible that an acid salt of the compound represented by the formula (VI) can be separated as a filtrate with high purity from an acid salt of the compound represented by the formula (VIII) of the present invention. When the salt formation reaction is appropriately performed, the compound represented by the formula (V) as a raw material of the present invention is not necessarily required to be a purified product, and it may be an unpurified product. The process can be applied for a large scale production, and favorable separation efficiency is also expected.

Preferred examples of an acid and a solvent include a combination of organic acid and acetic acid solvent or ester solvent. Preferred examples of the organic acid include citric acid, L-tartaric acid, oxalic acid, and p-toluene sulfonic acid. Preferred examples of the ester solvent include ethyl acetate.

As for the compound represented by the formula (VI) of the present invention wherein $R^9$ is a $C_{1-6}$ alkoxy group or an amino group, compound represented by the formula (VIII) of the present invention wherein $R^{13}$ is a $C_{1-6}$ alkoxy group or an amino group, or a mixture containing them at an arbitrary ratio for the salt formation reaction described above, purified product of each of them or a mixture containing purified products at an arbitrary ratio, or unpurified product of each of them or a mixture containing unpurified products at an arbitrary ratio can be used.

Examples of the inert solvent that can be used include alcohol type solvents such as methanol, ethanol, 2-propanol, tert-butyl alcohol, 2,2,2-trifluoro ethanol, or 1,1,1,3,3,3-hexafluoro-2-propanol;

hydrocarbon type solvents such as toluene, xylene, benzene, heptane, hexane, cyclohexane, or petroleum ether;

halogen type solvents such as dichloro methane, chloroform, 1,2-dichloro ethane, carbon tetrachloride, chloro benzene, or benzotrifluoride;

ether type solvents such as tetrahydrofuran, 2-methyl tetrahydrofuran, tetrahydropyran, diethyl ether, diisopropyl ether, tert-butyl methyl ether, cyclopentyl methyl ether, 1,2-dimethoxy ethane, diethoxy methane, or 1,4-dioxane;

ketone type solvents such as acetone, 2-butanone, or methyl isobutyl ketone;

ester type solvents such as ethyl acetate or isopropyl acetate;

acetonitrile, N,N-dimethylformamide, N-methylpyrrolidone, dimethyl sulfoxide, formic acid, acetic acid, water, or a mixture of these solvents.

Examples of the acid include an inorganic acid such as hydrochloric acid, hydrobromic acid, sulfuric acid, phosphoric acid, nitric acid, or boric acid, and;

an organic acid such as formic acid, acetic acid, propionic acid, 2-ethyl hexanoic acid, trifluoroacetic acid, trichloroacetic acid, pyruvic acid, diphenyl acetic acid, cinnamic acid, glycolic acid, D-lactic acid, L-lactic acid, D-mandelic acid, L-mandelic acid, D-glucuronic acid, D-gluconic acid, lactobionic acid, oxalic acid, malonic acid, succinic acid, glutaric acid, adipic acid, fumaric acid, maleic acid, (+)-camphoric acid, 2-ketoglutaric acid, glutamic acid, asparaginic acid, pyroglutamic acid, D-tartaric acid, L-tartaric acid, D-malic acid, L-malic acid, citric acid, benzoic acid, 4-hydroxybenzoic acid, salicylic acid, phthalic acid, isophthalic acid, terephthalic acid, methane sulfonic acid, trifluoromethane sulfonic acid, ethane sulfonic acid, benzene sulfonic acid, p-toluene sulfonic acid, (+)-10-camphor sulfonic acid, (−)-10-camphor sulfonic acid, and isethionic acid.

The reaction temperature may be usually from −80° C. to the boiling point of the solvent used, is preferably in the range of 0 to 50° C., and is more preferably in the range of 0 to 30° C.

The amount of acid that can be used may be in the range of 0.33 to 50 molar equivalents relative to a compound represented by the formula (VI), a compound represented by the formula (VIII), or a mixture containing them, preferably in the range of 1 to 10 molar equivalents, and more preferably in the range of 1 to 5 molar equivalents.

With regard to the amount of solvent, it may be used at 1 to 100 times by mass relative to a compound represented by the formula (VI), a compound represented by the formula (VIII), or a mixture containing them, preferably in the range of 1 to 30 times by mass, and more preferably in the range of 1 to 20 times by mass.

The compound represented by the formula (VI) of the present invention or a salt thereof and compound represented by the formula (VIII) of the present invention or a salt thereof can be obtained as a purified product of each of them or a mixture containing purified products at an arbitrary ratio, or unpurified product of each of them or a mixture containing unpurified products at an arbitrary ratio according to the process like chromatography, re-crystallization, re-slurry, isoelectric precipitation, isoelectric crystallization, neutralization crystal precipitation, and distillation.

(Step 5): A compound represented by the formula (VII) of the present invention or a salt thereof (provided that $R^{10}$ and $R^{11}$ are not simultaneously a hydroxyl group) can be obtained by reacting the compound represented by the formula (VI) or a salt thereof under an acidic condition or a basic condition. In particular, a compound represented by the formula (VII) of the present invention wherein $R^{10}$ is an amino group or a salt thereof can be also obtained by reacting the compound represented by the formula (VI) or a salt thereof under an oxidizing condition (reference literature: R. C. Larock, "Comprehensive Organic Transformations").

Examples of the acidic condition include performing the reaction at the temperature of 0 to 100° C. by using acid like hydrochloric acid, hydrogen bromide, sulfuric acid, phosphoric acid, polyphosphoric acid, methane sulfonic acid, p-toluene sulfonic acid, trifluoromethane sulfonic acid, formic acid, acetic acid, trifluoroacetic acid, and boron trifluoride.diethyl ether complex and a solvent like water, methanol, ethanol, 2-propanol, formic acid, acetic acid, acetone, ethyl acetate, tetrahydrofuran, and 1,4-dioxane, or a mixture solvent thereof.

Examples of the basic condition include performing the reaction at the temperature of 0 to 100° C. by using base like lithium hydroxide, sodium hydroxide, potassium hydroxide, and barium hydroxide and a solvent like water, methanol, ethanol, 2-propanol, tert-butyl alcohol, ethylene glycol, diethylene glycol, ethylene glycol monomethyl ether, ethylene glycol monoethyl ether, tetrahydrofuran, or a mixture solvent thereof.

Examples of the oxidizing condition include performing the reaction at the temperature of 0 to 50° C. by using hydrogen peroxide, a base like lithium hydroxide, sodium hydroxide, potassium hydroxide, potassium carbonate, sodium carbonate, ammonium hydroxide and sodium phosphate, or an aqueous solution thereof, and a solvent like dimethyl sulfoxide (reference literature: Synthesis, 949-950 (1989) and Bull. Chem. Soc. Jpn., 54, 793-799 (1981)).

The amount of hydrogen peroxide used for oxidizing condition may be in the range of 1 to 5 molar equivalents relative to the compound represented by the formula (VI) or a salt thereof, and preferably in the range of 1 to 2 molar equivalents.

The amount of base that can be used for oxidizing condition may be in the range of 0.1 to 5 molar equivalents relative to the compound represented by the formula (VI), and preferably in the range of 0.1 to 1 molar equivalents. Regarding an acid salt of the compound represented by the formula (VI), an amount of base required for converting the salt into free base form is preferably added to the use amount of base described above. When an aqueous solution of base is used, it may be used in the range of 0.1 to 10 molar (M) concentration, and preferably in the range of 1 to 10 molar concentrations.

With regard to the amount of solvent used like dimethyl sulfoxide under an oxidizing condition, it may be used at 1 to 100 times by mass relative to the compound represented by the formula (VI) or a salt thereof, preferably in the range of 1 to 10 times by mass, and more preferably in the range of 1 to 5 times by mass.

The compound represented by the formula (VII) of the present invention or a salt thereof may be obtained as a single compound or a mixture thereof.

The compound represented by the formula (VII) of the present invention or a salt thereof can be obtained as a purified product or a unpurified product according to the process like chromatography, re-crystallization, re-slurry, isoelectric precipitation, isoelectric crystallization, neutralization crystal precipitation, and distillation.

The compound represented by the formula (VII) of the present invention or a salt thereof can be used as a reaction mixture for the next Step 6 without being isolated or purified.

(Step 6): A compound represented by the formula (I) of the present invention or a salt thereof can be obtained by hydrolyzing the compound represented by the formula (VII) or a salt thereof under an acid condition or a basic condition (reference literature: R. C. Larock, "Comprehensive Organic Transformations").

Examples of the acidic condition include performing the reaction at the temperature of 0 to 100° C. by using acid like hydrochloric acid, hydrogen bromide, sulfuric acid, phosphoric acid, polyphosphoric acid, methane sulfonic acid, p-toluene sulfonic acid, trifluoromethane sulfonic acid, formic acid, acetic acid, trifluoroacetic acid, and boron trifluoride diethyl ether complex and a solvent like water, methanol, ethanol, 2-propanol, formic acid, acetic acid, acetone, ethyl acetate, tetrahydrofuran, and 1,4-dioxane, or a mixture solvent thereof.

Examples of the basic condition include performing the reaction at the temperature of 0 to 100° C. by using base like lithium hydroxide, sodium hydroxide, potassium hydroxide, and barium hydroxide and a solvent like water, methanol, ethanol, 2-propanol, tert-butyl alcohol, ethylene glycol, diethylene glycol, ethylene glycol monomethyl ether, ethylene glycol monoethyl ether, tetrahydrofuran, or a mixture solvent thereof.

The compound represented by the formula (I) of the present invention or a salt thereof can be obtained as a purified product or a unpurified product according to the process like isoelectric precipitation, isoelectric crystallization, chromatography, re-crystallization, re-slurry, neutralization crystal precipitation, distillation and sublimation.

(Step 7): A compound represented by the formula (I) of the present invention or a salt thereof can be obtained by reacting the compound represented by the formula (VI) or a salt thereof under an acidic condition, a basic condition, a basic condition which follows an oxidizing condition, or an oxidizing basic condition.

Examples of the acidic condition include performing the reaction at the temperature of 0 to 100° C. by using acid like hydrochloric acid, hydrogen bromide, sulfuric acid, phosphoric acid, polyphosphoric acid, methane sulfonic acid, p-toluene sulfonic acid, trifluoromethane sulfonic acid, formic acid, acetic acid, and trifluoroacetic acid and a solvent like water, methanol, ethanol, 2-propanol, formic acid, acetic acid, acetone, ethyl acetate, tetrahydrofuran, and 1,4-dioxane, or a mixture solvent thereof.

Examples of the basic condition include performing the reaction at the temperature of 0 to 100° C. by using base like lithium hydroxide, sodium hydroxide, potassium hydroxide, and barium hydroxide and a solvent like water, methanol, ethanol, 2-propanol, tert-butyl alcohol, ethylene glycol, diethylene glycol, ethylene glycol monomethyl ether, ethylene glycol monoethyl ether, tetrahydrofuran, or a mixture solvent thereof.

Examples of the basic condition which follows the oxidizing condition include performing the reaction under oxidizing condition at the temperature of 0 to 50° C. by using hydrogen peroxide, a base like lithium hydroxide, sodium hydroxide, potassium hydroxide, potassium carbonate, sodium carbonate, ammonium hydroxide, and sodium phosphate, or an aqueous solution thereof, and a solvent like dimethyl sulfoxide (reference literature: Synthesis, 949-950 (1989) and Bull. Chem. Soc. Jpn., 54, 793-799 (1981)) followed by reaction under basic condition by performing the reaction at the temperature of 0 to 100° C. by adding, to the reaction liquid, base like lithium hydroxide, sodium hydroxide, potassium hydroxide, and barium hydroxide, or an aqueous solution thereof, and a solvent like water, methanol, ethanol, 2-propanol, tert-butyl alcohol, ethylene glycol, diethylene glycol, ethylene glycol monomethyl ether, ethylene glycol monoethyl ether, tetrahydrofuran, or a mixture solvent thereof.

The amount of hydrogen peroxide used for oxidizing condition may be in the range of 1 to 5 molar equivalents relative to the compound represented by the formula (VI) or a salt thereof, and preferably in the range of 1 to 2 molar equivalents.

The amount of base that can be used for oxidizing condition may be in the range of 0.1 to 5 molar equivalents relative to the compound represented by the formula (VI), and preferably in the range of 0.1 to 1 molar equivalents. Regarding an acid salt of the compound represented by the formula (VI), an amount of base required for converting the salt into free base form is preferably added to the use amount of base described above. When an aqueous solution of base is used, it may be used in the range of 0.1 to 10 molar (M) concentration, and preferably in the range of 1 to 10 molar concentrations.

With regard to the amount of solvent used like dimethyl sulfoxide under an oxidizing condition, it may be used at 1 to 100 times by mass relative to the compound represented by the formula (VI) or a salt thereof, preferably in the range of 1 to 10 times by mass, and more preferably in the range of 1 to 5 times by mass.

The reaction time for the oxidizing condition is the time until the loss of the compound represented by the formula (VI) as a raw material is identified by high performance liquid chromatography (HPLC) or thin layer chromatography (TLC), and it is generally in the range of 0.1 to 24 hours.

The amount of base that can be used for basic condition following the oxidizing condition may be in the range of 3 to 30 molar equivalents relative to the compound represented by the formula (VI), and preferably in the range of 3 to 10 molar equivalents. When an aqueous solution of base is used, it may be used in the range of 0.1 to 10 molar (M) concentration, and preferably in the range of 1 to 10 molar concentrations.

The amount of solvent for basic condition following the oxidizing condition may be used at 1 to 100 times by mass relative to the compound represented by the formula (VI) or a salt thereof, preferably in the range of 1 to 10 times by mass, and more preferably in the range of 1 to 5 times by mass. However, the solvent may not be used.

Examples of the oxidizing basic condition include performing the reaction at the temperature of 0 to 40° C. by using hydrogen peroxide, a base like lithium hydroxide, sodium hydroxide, potassium hydroxide, potassium carbonate, sodium carbonate, ammonium hydroxide, and sodium phosphate, or an aqueous solution thereof, and a solvent like dimethyl sulfoxide followed by reaction at the temperature of 50 to 100° C.

The amount of hydrogen peroxide used for oxidizing basic condition may be in the range of 1 to 5 molar equivalents relative to the compound represented by the formula (VI) or a salt thereof, and preferably in the range of 1 to 2 molar equivalents.

The amount of base that can be used for oxidizing basic condition may be in the range of 3 to 30 molar equivalents relative to the compound represented by the formula (VI), and preferably in the range of 5 to 15 molar equivalents. Regarding an acid salt of the compound represented by the formula (VI), an amount of base required for converting the salt into free base form is preferably added to the use amount of base described above. When an aqueous solution of base is used, it may be used in the range of 0.1 to 10 molar (M) concentration, and preferably in the range of 1 to 10 molar concentrations.

The amount of solvent like dimethyl sulfoxide used for oxidizing basic condition may be used at 1 to 100 times by mass relative to the compound represented by the formula (VI) or a salt thereof, preferably in the range of 1 to 10 times by mass, and more preferably in the range of 1 to 5 times by mass.

The reaction time for the oxidizing basic condition at the temperature of 0 to 40° C. is the time until the loss of the compound represented by the formula (VI) as a raw material is identified by high performance liquid chromatography (HPLC) or thin layer chromatography (TLC), and it is generally in the range of 0.1 to 24 hours.

The compound represented by the formula (I) of the present invention or a salt thereof can be obtained as a purified product or a unpurified product according to the process like isoelectric precipitation, isoelectric crystallization, chromatography, re-crystallization, re-slurry, distillation, and sublimation.

<Scheme 2>

[Chemical Formula 26]

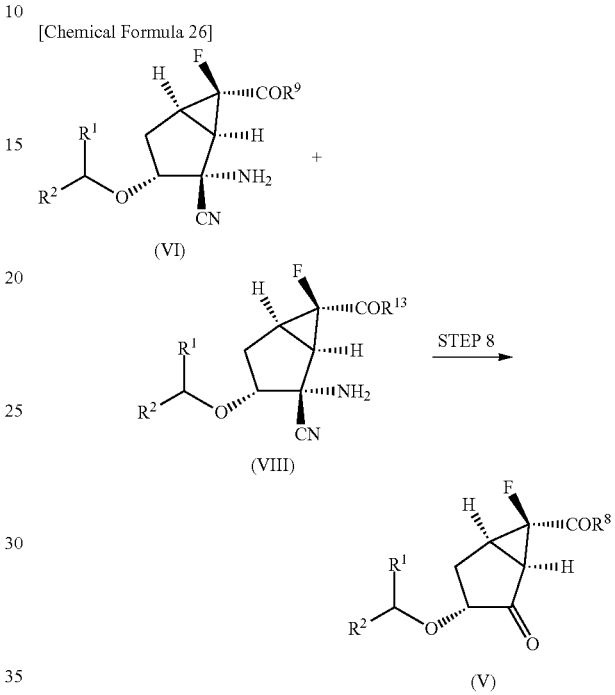

In the formulae of the above Scheme 2, $R^1$, $R^2$, $R^8$, $R^9$, and $R^{13}$ are as defined in the above.

(Step 8): A compound represented by the formula (V) of the present invention or a salt thereof can be obtained by reacting the compound represented by the formula (VI) of the present invention or a salt thereof, the compound represented by the formula (VIII) of the present invention or a salt thereof, or a mixture containing them at an arbitrary ratio under an acidic condition.

Examples of the acidic condition include performing the reaction at the temperature of 0 to 150° C. by using acid like hydrochloric acid, hydrogen bromide, sulfuric acid, phosphoric acid, polyphosphoric acid, methane sulfonic acid, p-toluene sulfonic acid, trifluoromethane sulfonic acid, formic acid, acetic acid, trifluoroacetic acid, and boron trifluoride.diethyl ether complex and a solvent like water, methanol, ethanol, 2-propanol, formic acid, acetic acid, acetone, ethyl acetate, tetrahydrofuran, and 1,4-dioxane, or a mixture solvent thereof.

The compound represented by the formula (VI) of the present invention or a salt thereof, the compound represented by the formula (VIII) of the present invention or a salt thereof, or a mixture containing them at an arbitrary ratio can be used as a purified product of each of them or a mixture containing purified products at an arbitrary ratio, or unpurified product of each of them or a mixture containing unpurified products at an arbitrary ratio.

For example, a mixture fraction generated during isolation or purification of the compound during the Step 4, mother liquor of recrystallization or concentrated residue thereof, or filtrate obtained by filtering solids that is generated during isolation or purification of an acid salt of the compound or concentrated residues thereof can be also used. Specifically, by performing the present reaction step, the compound represented by the formula (VIII) of the present invention or a salt thereof, which is a byproduct not having stereochemistry desired for synthesis of the compound represented by the formula (I) or a salt thereof, is converted into the compound represented by the formula (V) of the present invention or a salt thereof as a synthetic intermediate of the compound represented by the formula (I) or a salt thereof, and therefore can be effectively used without being discarded.

The compound represented by the formula (V) of the present invention or a salt thereof can be obtained as a purified product or a unpurified product according to the process like chromatography, re-crystallization, re-slurry, neutralization crystal precipitation, and distillation.

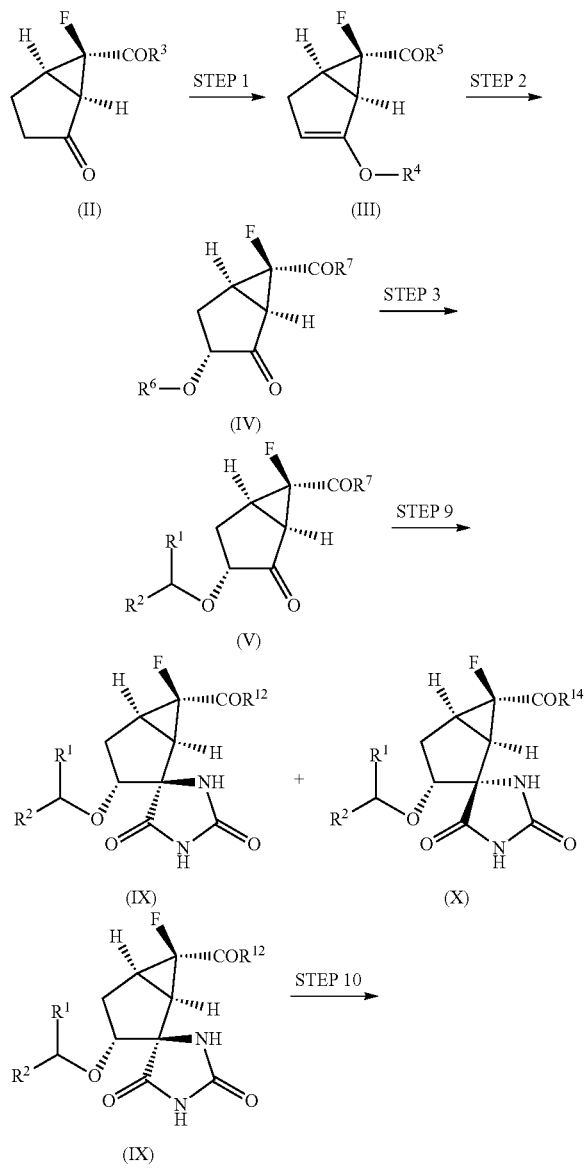

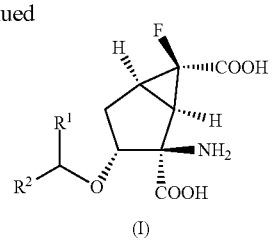

In the formulae of the above Scheme 3, $R^1$, $R^2$, $R^3$, $R^4$, $R^5$, $R^6$, $R^7$, $R^8$, $R^{12}$, and $R^{14}$ are as defined in the above.

Further, the Step 1, Step 2, and Step 3 are as defined in the above Scheme 1.

(Step 9): A compound represented by the formula (IX) of the present invention or a salt thereof, a compound represented by the formula (X) of the present invention or a salt thereof, or a mixture containing compound represented by the formula (IX) of the present invention or a salt thereof and the compound represented by the formula (X) of the present invention or a salt thereof can be obtained by reacting the compound represented by the formula (V) or a salt thereof with ammonium carbonate, and potassium cyanide or sodium cyanide in an inert solvent (reference literature: Tetrahedron: Asymmetry, 8, 511-514 (1997), J. Med. Chem., 43, 4893-4909 (2000), J. Org. Chem., 69, 4516-4519 (2004), Tetrahedron 60, 6711-6745 (2004), Tetrahedron: Asymmetry, 20, 1-63 (2009), and Org. Proc. Res. Dev., 10, 28-32 (2006)).

Examples of the inert solvent that can be used include alcohol type solvents such as methanol, ethanol, propanol, 2-propanol, or ethylene glycol, and;

N,N-dimethyl formamide, dimethyl sulfoxide, water, or a mixture of these solvents. Preferably, a mixture of water and an alcohol type solvent is used.

The reaction temperature may be usually from 0° C. to the boiling point of the solvent used, is preferably in the range of 20 to 80° C., and is more preferably in the range of 40 to 70° C.

The amount of ammonium carbonate used may be in the range of 2 to 20 molar equivalents relative to the compound represented by the formula (V), preferably in the range of 3 to 10 molar equivalents, and more preferably in the range of 3 to 5 molar equivalents.

The amount of potassium cyanide or sodium cyanide used may be in the range of 1 to 10 molar equivalents relative to the compound represented by the formula (V), preferably in the range of 1 to 5 molar equivalents, and more preferably in the range of 1 to 3 molar equivalents.

With regard to the amount of solvent, it may be used at 1 to 100 times by mass relative to the compound represented by the formula (V), preferably in the range of 1 to 30 times by mass, and more preferably in the range of 1 to 10 times by mass.

A compound represented by the formula (IX) of the present invention wherein $R^{12}$ is a hydroxyl group or a salt thereof, a compound represented by the formula (X) of the present invention wherein $R^{14}$ is a hydroxyl group or a salt thereof, or a mixture containing compound represented by the formula (IX) of the present invention wherein $R^{12}$ is a hydroxyl group or a salt thereof and a compound represented by the formula (X) of the present invention wherein $R^{14}$ is a hydroxyl group or a salt thereof can be obtained by reacting a compound represented by the formula (V) wherein $R^8$ is a $C_{1-6}$ alkoxy group with a base like an aqueous solution of sodium hydroxide or potassium hydroxide in a solvent such as methanol or ethanol for conversion into a compound represented by the formula (V) wherein $R^8$ is a hydroxyl group or a salt thereof and adding ammonium carbonate and potassium cyanide or sodium cyanide to the reaction mixture.

A compound represented by the formula (IX) of the present invention wherein $R^{12}$ is a methoxy group or an ethoxy group or a salt thereof, a compound represented by the formula (X) of the present invention wherein $R^{14}$ is a methoxy group or an ethoxy group or a salt thereof, or a mixture containing the compound represented by the formula (IX) of the present invention wherein $R^{12}$ is a methoxy group or an ethoxy group or a salt thereof and the compound represented by the formula (X) of the present invention wherein $R^{14}$ is a methoxy group or an ethoxy group or a salt thereof can be obtained by reacting a compound represented by the formula (IX) of the present invention wherein $R^{12}$ is a hydroxyl group or a salt thereof, a compound represented by the formula (X) of the present invention wherein $R^{14}$ is a hydroxyl group or a salt thereof, or a mixture containing the compound represented by the formula (IX) of the present invention wherein $R^{12}$ is a hydroxyl group or a salt thereof and the compound represented by the formula (X) of the present invention wherein $R^{14}$ is a hydroxyl group or a salt thereof with methanol or ethanol, a base like 4-dimethylaminopyridine, and a condensing agent like 1-ethyl-3-(3-dimethylaminopropyl)carbodiimide in a solvent like N,N-dimethyl formamide.

A compound represented by the formula (IX) of the present invention wherein $R^{12}$ is a hydroxyl group or a salt thereof, a compound represented by the formula (X) of the present invention wherein $R^{14}$ is a hydroxyl group or a salt thereof, or a mixture containing the compound represented by the formula (IX) of the present invention wherein $R^{12}$ is a hydroxyl group or a salt thereof and the compound represented by the formula (X) of the present invention wherein $R^{14}$ is a hydroxyl group or a salt thereof can be obtained by hydrolyzing a compound represented by the formula (IX) of the present invention wherein $R^{12}$ is a $C_{1-6}$ alkoxy group or a salt thereof, a compound represented by the formula (X) of the present invention wherein $R^{14}$ is a $C_{1-6}$ alkoxy group or a salt thereof, or a mixture of the compound represented by the formula (IX) of the present invention wherein $R^{12}$ is a $C_{1-6}$ alkoxy group or a salt thereof and the compound represented by the formula (X) of the present invention wherein $R^{14}$ is a $C_{1-6}$ alkoxy group or a salt thereof in an aqueous solution of sodium hydroxide or an aqueous solution of potassium hydroxide.

A compound represented by the formula (IX) of the present invention or a salt thereof, the compound represented by the formula (X) of the present invention or a salt thereof, or a mixture of the compound represented by the formula (IX) of the present invention or a salt thereof and the compound represented by the formula (X) of the present invention or a salt thereof can be obtained as a purified product or a unpurified product according to the process like chromatography, re-crystallization, re-slurry, neutralization crystal precipitation, and distillation.

(Step 10): A compound represented by the formula (I) of the present invention or a salt thereof can be obtained by reacting a compound represented by the formula (IX) of the present invention or a salt thereof or a mixture of the compound represented by the formula (IX) of the present invention or a salt thereof and a compound represented by the formula (X) of the present invention or a salt thereof under an acidic condition or a basic condition.

Examples of the basic condition include performing the reaction at the temperature of 0° C. to reflux temperature by using base like lithium hydroxide, sodium hydroxide, potassium hydroxide, and barium hydroxide and a solvent like water, methanol, ethanol, 2-propanol, tert-butyl alcohol, ethylene glycol, diethylene glycol, ethylene glycol monomethyl ether, ethylene glycol monoethyl ether, tetrahydrofuran, or a mixture solvent thereof.

Examples of the acidic condition include performing the reaction at the temperature of 0° C. to reflux temperature by using acid like hydrochloric acid, hydrogen bromide, sulfuric acid, methane sulfonic acid, p-toluene sulfonic acid, trifluoromethane sulfonic acid, and trifluoroacetic acid, and a solvent like water, methanol, ethanol, 2-propanol, formic acid, acetic acid, tetrahydrofuran, and 1,4-dioxane, or a mixture solvent thereof.

The compound represented by the formula (I) of the present invention or a salt thereof can be obtained as a purified product or a unpurified product according to the process like isoelectric precipitation, isoelectric crystallization, chromatography, re-crystallization, re-slurry, distillation, and sublimation.

EXAMPLES

Hereinbelow, the present invention is specifically explained in greater detail with reference to the examples given below. However, the present invention is not construed to be limited to the descriptions of the examples. The yield described in the examples below is sometimes affected by reaction condition, thus higher yield can be obtained by selecting an optimized reaction condition.

Example 1

Synthesis of ethyl (1R,5R,6R)-6-fluoro-2-[(trimethylsilyl)oxy]bicyclo[3.1.0]hex-2-ene-6-carboxylate
(3a)

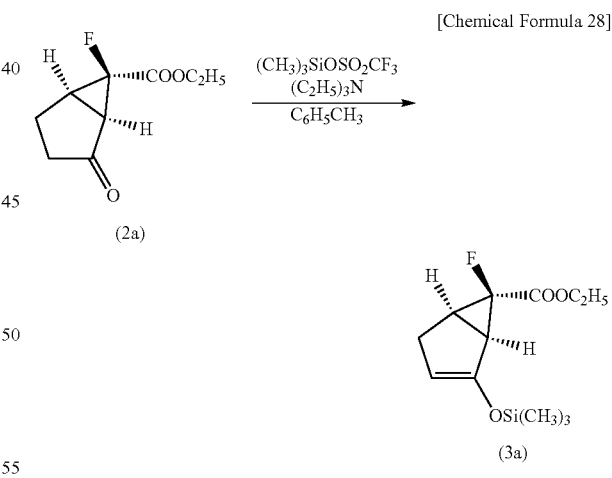

[Chemical Formula 28]

205 g of triethyl amine was added to a toluene (1251 g) solution containing 250 g of ethyl (1R,5R,6R)-6-fluoro-2-oxo bicyclo[3.1.0]hexane-6-carboxylate (2a). The solution obtained was cooled to the temperature of 5° C. or less, and 359 g of trimethylsilyl trifluoromethane sulfonic acid was added dropwise to the solution while keeping the internal temperature at 5° C. or less. When the dropwise addition is completed, 1253 g of water was added for liquid separation. The organic layer was washed with 1252 g of 5 wt % aqueous solution of sodium hydrogen carbonate and 1251 g of water in order. The organic layer was concentrated under reduced pressure, and the resulting residues were added with 631 g of toluene and concentrated again under reduced pressure to give concentrated residues of ethyl (1R,5R,6R)-6-fluoro-2-[(trimethylsilyl)oxy]bicyclo[3.1.0]hexa-2-ene-6-carboxylate (3a).

$^1$H NMR (600 MHz, CDCl$_3$) δ: 0.22 (s, 9H), 1.32 (t, J=7.2 Hz, 3H), 2.28-2.32 (m, 1H), 2.42-2.48 (m, 1H), 2.54-2.57 (m, 1H), 2.65-2.71 (m, 1H), 4.27 (q, J=7.2 Hz, 2H), 4.62-4.64 (m, 1H). MS (EI) m/z: 258 (M$^+$), 223 (base).

Example 2

Synthesis of ethyl (1R,3R,5R,6R)-6-fluoro-3-hydroxy-2-oxo bicyclo[3.1.0]hexane-6-carboxylate (4a)

[Chemical Formula 29]

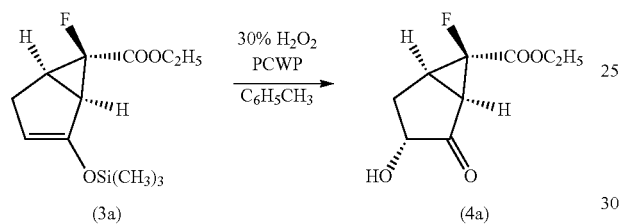

(3a)    (4a)

To the concentrated residues of ethyl (1R,5R,6R)-6-fluoro-2-[(trimethylsilyl)oxy]bicyclo[3.1.0]hexa-2-ene-6-carboxylate (3a) obtained from the Example 1, 2577 g of toluene and 111 g of tris(cetyl pyridinium)peroxo tungstophosphate (PCWP) (reference literature: J. Org. Chem., 53, 3587-3593 (1988) and J. Org. Chem., 62, 7174-7177 (1997)) were added and heated to 30° C. 183 g of 30 wt % hydrogen peroxide was added dropwise to the solution over 1 hr and 10 min while keeping the internal temperature at 45° C. or less and stirred for 10 min. The reaction solution was cooled in an ice batch and added with 347 g of 5 wt % aqueous solution of sodium hydrogen carbonate and 1420 g of 30 wt % aqueous solution of sodium thiosulfate in order. After removing the solvent by distillation under reduced pressure, 114 g of cellulose powder (KC-flock) and 1745 g of ethyl acetate were added to the residues and stirred overnight. After filtering the suspension, the solid was washed with 1737 g of ethyl acetate. The filtrate and washing solution were combined and subjected to liquid separation. The aqueous layer was extracted with 1728 g of ethyl acetate. The organic layer was combined and concentrated under reduced pressure. The resulting residues were purified by silica gel column chromatography (eluent solution; hexane:ethyl acetate=5:1, followed by 1:1), 201 g of ethyl (1R,3R,5R,6R)-6-fluoro-3-hydroxy-2-oxo bicyclo[3.1.0]hexane-6-carboxylate (4a) was obtained as a light brown oily material.

$^1$H NMR (600 MHz, CDCl$_3$) δ: 1.34 (t, J=7.2 Hz, 3H), 2.31-2.37 (m, 1H), 2.58 (br s, 1H, exchangeable with D$_2$O), 2.61-2.64 (m, 1H), 2.72-2.77 (m, 2H), 4.05-4.10 (m, 1H), 4.31 (q, J=7.2 Hz, 2H). MS (EI) m/z: 202 (M$^+$), 125 (base).

Example 3

Synthesis of ethyl (1RS,3RS,5RS,6RS)-6-fluoro-3-hydroxy-2-oxo bicyclo[3.1.0]hexane-6-carboxylate (4a') and ethyl (1RS,3RS,5RS,6RS)-3-[(3-chlorobenzoyl)oxy]-6-fluoro-2-oxo bicyclo[3.1.0]hexane-6-carboxylate (4b')

[Chemical Formula 30]

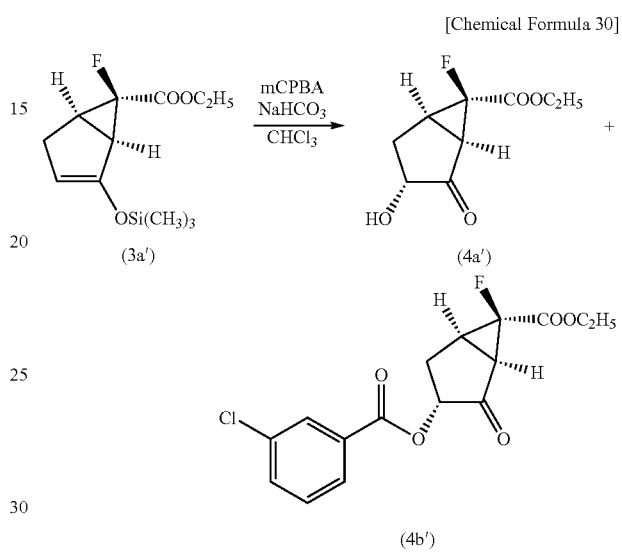

A chloroform (302.1 g) solution containing 41.35 g (content: 84.2 wt %) of ethyl (1RS,5RS,6RS)-6-fluoro-2-[(trimethylsilyl)oxy]bicyclo[3.1.0]hexa-2-ene-6-carboxylate (3a') was cooled to 6° C., added with 22.94 g of sodium hydrogen carbonate, and further added with 39.50 g (content: 65 wt %) of 3-chloro perbenzoic acid (mCPBA) at the temperature of 11° C. or less over 44 min. The mixture was warmed to 25° C. over 4.5 hrs under stirring. The reaction solution was added with an aqueous solution of sodium thiosulfate (anhydrous sodium thiosulfate 7.48 g and water 75.61 g) and stirred for 25 min. After keeping it for 10 min, it was separated into an organic layer and an aqueous layer. The aqueous layer was extracted again with 151.6 g and 151.1 g of chloroform. The organic layer was combined, washed with 96 g of water, and added with 30.26 g of anhydrous magnesium sulfate. After stirring for 5 min, insoluble materials were removed by filtration. The filtrate was concentrated under reduced pressure and the residues were purified by silica gel column chromatography (eluent solution; hexane:ethyl acetate=4:1 to 3:1) to obtain 7.436 g of ethyl (1RS,3RS,5RS,6RS)-6-fluoro-3-hydroxy-2-oxo bicyclo[3.1.0]hexane-6-carboxylate (4a') as a colorless oily material and 19.33 g of ethyl (1RS,3RS,5RS,6RS)-3-[(3-chlorobenzoyl)oxy]-6-fluoro-2-oxo bicyclo[3.1.0]hexane-6-carboxylate (4b') as a colorless solid. 19.33 g of the compound (4b') was recrystallized with ethyl acetate-hexane to obtain 10.74 g of the compound (4b') as a colorless solid.

(4b'): $^1$H NMR (300 MHz, CDCl$_3$) δ: 1.35 (t, J=7.2 Hz, 3H), 2.52-2.63 (m, 1H), 2.72-2.77 (m, 1H), 2.82-2.94 (m, 2H), 4.33 (q, J=7.2 Hz, 2H), 5.17-5.26 (m, 1H), 7.40 (t, J=7.9 Hz, 1H), 7.54-7.59 (m, 1H), 7.92-7.96 (m, 1H), 8.01-8.04 (m, 1H). MS (ESI/APCI Dual) m/z: 341 [(M+H)$^+$], 343 {[(M+

2)+H]$^+$}, 363 [(M+Na)$^+$], 365 {[(M+2)+Na]$^+$}. IR (KBr) cm$^{-1}$: 3072, 2968, 1756, 1722, 1324, 1290, 1255, 1218, 1128, 1105, 1086, 1012, 748. Anal. Calcd. for $C_{16}H_{14}ClFO_5$: C, 56.40; H, 4.14; Cl, 10.41; F, 5.58. Found: C, 56.41; H, 4.18; Cl, 10.36; F, 5.58.

Example 4

Synthesis of methyl (1RS,3RS,5RS,6RS)-6-fluoro-3-hydroxy-2-oxo bicyclo[3.1.0]hexane-6-carboxylate (4c') and methyl (1RS,3RS,5RS,6RS)-3-[(3-chlorobenzoyl)oxy]-6-fluoro-2-oxo bicyclo[3.1.0]hexane-6-carboxylate (4d')

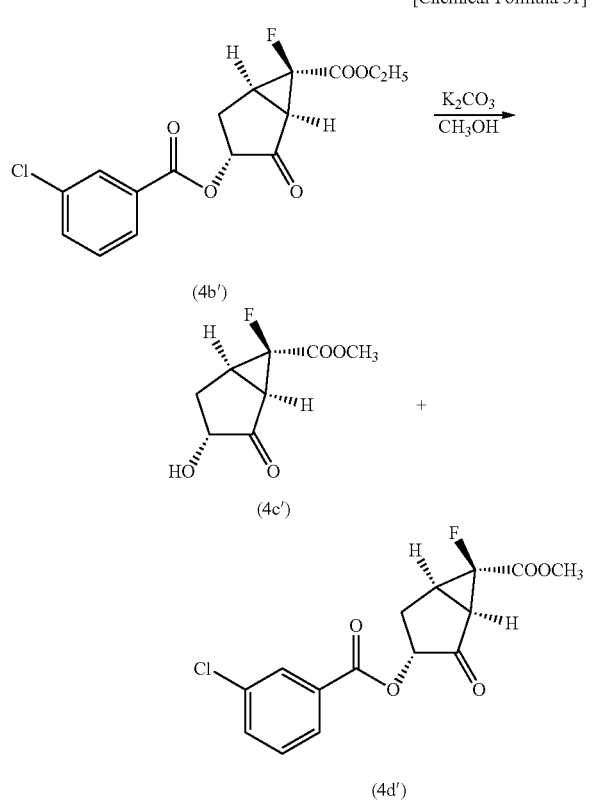

[Chemical Formula 31]

chlorobenzoyl)oxy]-6-fluoro-2-oxo bicyclo[3.1.0]hexane-6-carboxylate (4d') as a colorless foamy solid.

(4c'): $^1$H NMR (300 MHz, CDCl$_3$) δ: 2.30-2.41 (m, 1H), 2.61-2.66 (m, 1H), 2.68 (br s, 1H, exchangeable with D$_2$O), 2.70-2.81 (m, 2H), 3.87 (s, 3H), 4.03-4.13 (m, 1H).

(4d'): $^1$H NMR (300 MHz, CDCl$_3$) δ: 2.53-2.64 (m, 1H), 2.73-2.78 (m, 1H), 2.82-2.94 (m, 2H), 3.88 (s, 3H), 5.17-5.27 (m, 1H), 7.40 (t, J=7.9 Hz, 1H), 7.53-7.60 (m, 1H), 7.91-7.97 (m, 1H), 8.01-8.04 (m, 1H).

Example 5

Synthesis of ethyl (1RS,3RS,5RS,6RS)-6-fluoro-3-hydroxy-2-oxo bicyclo[3.1.0]hexane-6-carboxylate (4a'), ethyl (1RS,3RS,5RS,6RS)-6-fluoro-2-oxo-3-[(trimethylsilyl)oxy]bicyclo[3.1.0]hexane-6-carboxylate (4e'), and ethyl (1RS,5RS,6RS)-6-fluoro-2-oxo bicyclo[3.1.0]hexane-6-carboxylate (2a')

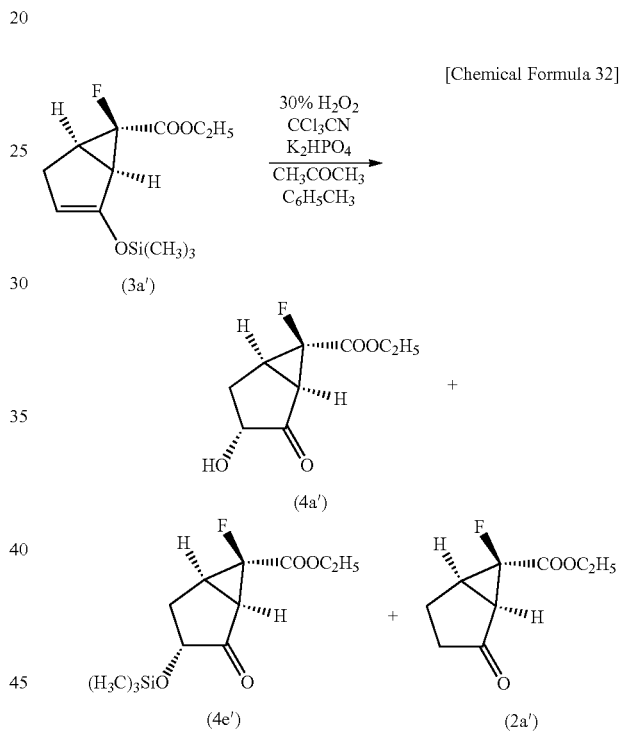

[Chemical Formula 32]

To a methanol (10.75 g) solution containing 1.072 g of ethyl (1RS,3RS,5RS,6RS)-3-[(3-chlorobenzoyl)oxy]-6-fluoro-2-oxo bicyclo[3.1.0]hexane-6-carboxylate (4b'), 0.031 g of potassium carbonate was added. The mixture was then stirred for four hrs and further added with 0.012 g of potassium carbonate. After stirring for 1 hr, the liquid was adjusted to pH 6 by adding 0.322 g of 1 M hydrochloric acid and stirred for 15 hrs. The reaction solution was concentrated under reduced pressure and added with chloroform and water to dissolve the residues. 1 M Hydrochloric acid was added to the mixture solution obtained so that the aqueous layer has pH 1 followed by extraction with chloroform. The organic layer was concentrated under reduced pressure and the residues were purified by silica gel column chromatography (eluent solution; hexane:ethyl acetate=4:1) to obtain 0.476 g of methyl (1RS,3RS,5RS,6RS)-6-fluoro-3-hydroxy-2-oxo bicyclo[3.1.0]hexane-6-carboxylate (4c') as a colorless oily material and 0.008 g of methyl (1RS,3RS,5RS,6RS)-3-[(3-

0.310 mL of Trichloro acetonitrile, 0.445 mL of acetone, and 0.105 g of dipotassium hydrogen phosphate were added to a toluene (3 mL) solution containing 0.44 g (content: 89.0 wt %) of ethyl (1RS,5RS,6RS)-6-fluoro-2-[(trimethylsilyl) oxy]bicyclo[3.1.0]hexa-2-ene-6-carboxylate (3a') and cooled in an ice bath. To the mixture, 0.347 g of 30 wt % hydrogen peroxide was added dropwise and stirred at 0 to 3° C. for 1 hr and subsequently at 19 to 22° C. for 3 hrs and 20 min. The reaction solution was cooled in an ice bath and added with 8 mL of 5 wt % aqueous solution of sodium sulfite followed by extraction with toluene. The organic layer was washed with saturated aqueous solution of sodium chloride and dried over anhydrous magnesium sulfate. The residues (0.480 g) that are obtained by removing the solvent by distillation under reduced pressure were purified by silica gel column chromatography (eluent solution; hexane:ethyl acetate=8:1, 5:1, 3:1) to obtain, in elution order, 0.014 g of ethyl (1RS,3RS,5RS,6RS)-6-fluoro-2-oxo-3-[(trimethylsilyl)oxy]bicyclo[3.1.0]hexane-6-carboxylate (4e') as a colorless oily material, 0.124 g of ethyl (1RS,5RS,6RS)-6-fluoro-2-oxo bicyclo[3.1.0]hexane-6-carboxylate (2a') as a colorless oily material, and 0.034 g of ethyl (1RS,3RS,5RS,6RS)-6-fluoro-3-hydroxy-2-oxo bicyclo[3.1.0]hexane-6-carboxylate (4a') as a colorless oily material.

(4e'): $^1$H NMR (600 MHz, CDCl$_3$) δ: 0.16 (s, 9H), 1.33 (t, J=7.2 Hz, 3H), 2.30-2.36 (m, 1H), 2.52-2.55 (m, 1H), 2.61-2.69 (m, 2H), 4.03-4.08 (m, 1H), 4.29 (q, J=7.2 Hz, 2H). MS (ESI/APCI Dual) m/z: 297 [(M+Na)$^+$].

Example 6

Synthesis of ethyl (1R,3R,5R,6R)-3-[(3,4-dichloro benzyl)oxy]-6-fluoro-2-oxo bicyclo[3.1.0]hexane-6-carboxylate (5a)

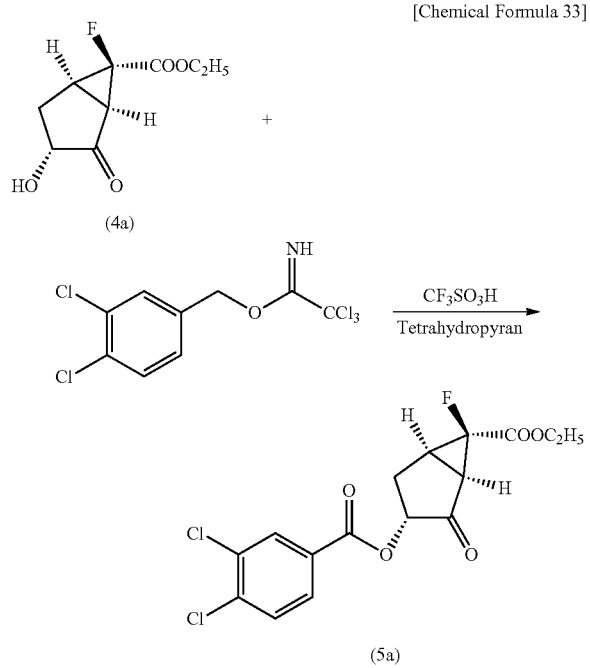

[Chemical Formula 33]

33.7 g (content: 85 wt %) of 3,4-dichloro benzyl 2,2,2-trichloroacetimidate was added to tetrahydropyran (120 g) solution containing 11.98 g of ethyl (1R,3R,5R,6R)-6-fluoro-3-hydroxy-2-oxo bicyclo[3.1.0]hexane-6-carboxylate (4a). The solution obtained was added with tetrahydropyran (12 g) solution containing 4.44 g of trifluoromethane sulfonic acid over 15 min at 24 to 31° C. After stirring for 1.5 hr at 24 to 30° C., the reaction solution was poured over 120 g of saturated aqueous solution of sodium hydrogen carbonate and the organic layer was washed with 134 g of 10% aqueous solution of sodium chloride. The organic layer was concentrated under reduced pressure and the residues were purified by silica gel column chromatography (eluent solution; hexane:ethyl acetate=4:1) to obtain 16.51 g of ethyl (1R,3R,5R,6R)-3-[(3,4-dichloro benzyl)oxy]-6-fluoro-2-oxo bicyclo[3.1.0]hexane-6-carboxylate (5a) as a yellow oily material.

$^1$H NMR (300 MHz, CDCl$_3$) δ: 1.33 (t, J=7.2 Hz, 3H), 2.34-2.45 (m, 1H), 2.57-2.75 (m, 3H), 3.84-3.93 (m, 1H), 4.30 (q, J=7.2 Hz, 2H), 4.56 (d, J=11.9 Hz, 1H), 4.95 (d, J=11.9 Hz, 1H), 7.18 (dd, J=8.2 and 2.1 Hz, 1H), 7.41 (d, J=8.2 Hz, 1H), 7.46 (d, J=2.1 Hz, 1H). MS (ESI/APCI Dual) m/z: 378 [(M+NH$_4$)$^+$].

Example 7

Synthesis of (1R,3R,5R,6R)-3-[(3,4-dichloro benzyl)oxy]-6-fluoro-2-oxo bicyclo[3.1.0]hexane-6-carboxamide (5b)

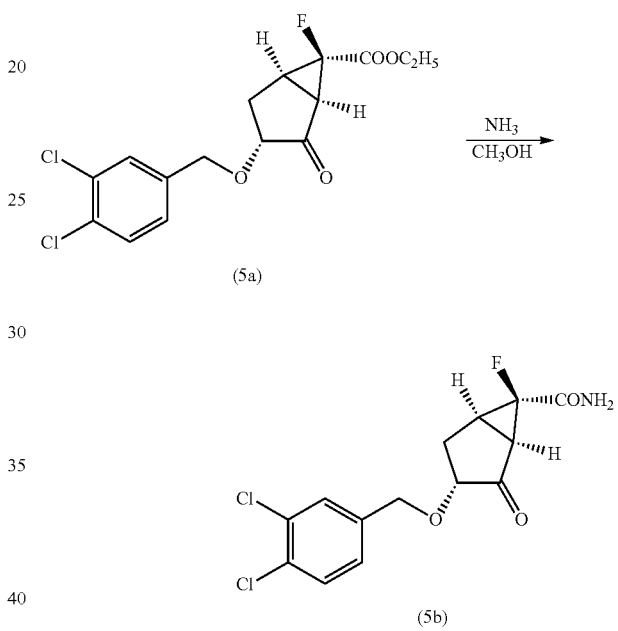

[Chemical Formula 34]

2.14 g of ethyl (1R,3R,5R,6R)-3-[(3,4-dichloro benzyl)oxy]-6-fluoro-2-oxo bicyclo[3.1.0]hexane-6-carboxylate (5a) was dissolved in 8 mL of 7 M ammonia-methanol solution and stirred at room temperature for 1 hr. The reaction solution was concentrated under reduced pressure to obtain 1.956 g of residues. 1.8 g of the residues were purified by silica gel column chromatography (eluent solution; chloroform:methanol=20:1) to obtain 1.02 g of solid. The solid was suspended in 3 mL of ethyl acetate, filtered, collected, and dried to obtain 0.4709 g of (1R,3R,5R,6R)-3-[(3,4-dichloro benzyl)oxy]-6-fluoro-2-oxo bicyclo[3.1.0]hexane-6-carboxamide (5b) as a colorless solid.

mp 157-160° C. $^1$H NMR (300 MHz, DMSO-d$_6$) δ: 2.29-2.39 (m, 1H), 2.40-2.45 (m, 1H), 2.55-2.64 (m, 1H), 2.67-2.74 (m, 1H), 3.85-3.94 (m, 1H), 4.61 (d, J=12.3 Hz, 1H), 4.79 (d, J=12.3 Hz, 1H), 7.34 (dd, J=8.2 and 2.2 Hz, 1H), 7.61 (d, J=2.2 Hz, 1H), 7.62 (d, J=8.2 Hz, 1H), 7.86 (br s, 1H, exchangeable with D$_2$O), 8.07 (br s, 1H, exchangeable with D$_2$O). MS (ESI/APCI Dual) m/z: 354 [(M+Na)$^+$]. IR (KBr) cm$^{-1}$: 3374, 3176, 1747, 1694, 1472, 1436, 1272, 1235, 1099, 986. Anal. Calcd for C$_{14}$H$_{12}$Cl$_2$FNO$_3$: C, 50.62; H, 3.64; N, 4.22; Cl, 21.35; F, 5.72. Found: C, 50.51; H, 3.67; N, 4.14; Cl, 21.24; F, 5.57.

Example 8

Synthesis of (1R,2S,3R,5R,6R)-2-amino-2-cyano-3-[(3,4-dichloro benzyl)oxy]-6-fluoro bicyclo[3.1.0]hexane-6-carboxamide (6a) and (1R,2R,3R,5R,6R)-2-amino-2-cyano-3-[(3,4-dichloro benzyl)oxy]-6-fluoro bicyclo[3.1.0]hexane-6-carboxamide (8a)

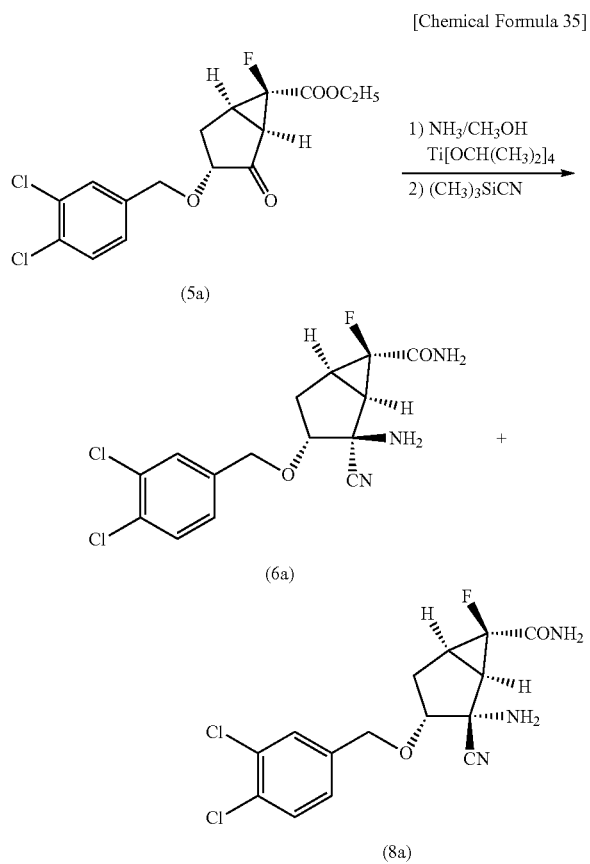

4.03 g of ethyl (1R,3R,5R,6R)-3-[(3,4-dichloro benzyl)oxy]-6-fluoro-2-oxo bicyclo[3.1.0]hexane-6-carboxylate (5a) was added to 13.9 mL of 8 M ammonia-methanol and 4.0 mL of titanium (IV) isopropoxide was added to the mixture solution under nitrogen atmosphere followed by stirring for 7 hrs at 25° C. The reaction solution was cooled in an ice bath, added with 1.66 mL of trimethylsilyl cyanide, and stirred at 0° C. for 6 hrs and subsequently at 0 to 19° C. for 12 hrs. To a crude product obtained by concentrating the reaction solution under reduced pressure, 50 mL of ethyl acetate was added to give a suspension. After filtration, the resulting solid was washed with 50 mL of ethyl acetate. The filtrate and washing solution were concentrated under reduced pressure to give residues, which were then purified by performing twice the silica gel column chromatography (first eluent solution; ethyl acetate:chloroform=4:1, second eluent solution; chloroform:ethyl acetate=1:2 to 1:4, followed by ethyl acetate) to give a fraction (1.06 g) which represents a spot in a less polar region in thin layer chromatography (silica gel $60F_{254}$ plate, developed with chloroform:methanol=10:1), a fraction (1.75 g) which represents a spot in more polar region, and a mixture of the fractions (0.36 g).

1.75 g of the fraction representing a spot in a more polar region was recrystallized with ethyl acetate and hexane to obtain 1.67 g of (1R,2S,3R,5R,6R)-2-amino-2-cyano-3-[(3,4-dichloro benzyl)oxy]-6-fluoro bicyclo[3.1.0]hexane-6-carboxamide (6a) as a colorless solid. Further, 1.06 g of the fraction representing a spot in a less polar region was suspended with ethyl acetate and hexane, and filtered to obtain 1.01 g of (1R,2R,3R,5R,6R)-2-amino-2-cyano-3-[(3,4-dichloro benzyl)oxy]-6-fluoro bicyclo[3.1.0]hexane-6-carboxamide (8a) as a colorless solid. 0.48 g of the concentrated residues obtained by combining each filtrate and the mixture fraction described above was suspended with ethyl acetate-hexane and filtered to obtain 0.371 g of a mixture of the compounds (6a) and (8a) as a colorless solid.

(6a): mp 121-125° C. $^1$H NMR (600 MHz, DMSO-$d_6$) δ: 1.98-2.02 (m, 1H), 2.12-2.18 (m, 1H), 2.26-2.29 (m, 1H), 2.34-2.39 (m, 1H), 3.68-3.73 (m, 1H), 4.62 (d, J=12.6 Hz, 1H), 4.73 (d, J=12.6 Hz, 1H), 7.38 (dd, J=8.4 and 2.0 Hz, 1H), 7.63 (d, =8.4 Hz, 1H), 7.65 (d, J=2.0 Hz, 1H), 7.65 (br s, 1H, exchangeable with $D_2O$), 7.84 (br s, 1H, exchangeable with $D_2O$). MS (ESI/APCI Dual) m/z: 380 [(M+Na)$^+$], 382 {[(M+2)+Na]$^+$}. IR (KBr) cm$^{-1}$: 3420, 3364, 3304, 3193, 2233, 1672, 1604, 1474, 1377, 1129, 1031. Anal. Calcd for $C_{15}H_{14}Cl_2FN_3O_2$: C, 50.30; H, 3.94; N, 11.73; Cl, 19.80; F, 5.30. Found: C, 50.25; H, 3.99; N, 11.52; Cl, 19.68; F, 5.08.

(8a): mp 183-186° C. $^1$H NMR (600 MHz, DMSO-$d_6$) δ: 1.94-1.98 (m, 1H), 2.15-2.21 (m, 1H), 2.24-2.31 (m, 2H), 3.97-4.02 (m, 1H), 4.59 (d, J=12.2 Hz, 1H), 4.72 (d, J=12.2 Hz, 1H), 7.38 (dd, J=8.3 and 1.8 Hz, 1H), 7.63 (d, J=8.3 Hz, 1H), 7.67 (d, J=1.8 Hz, 1H), 7.68 (br s, 1H, exchangeable with $D_2O$), 7.92 (br s, 1H, exchangeable with $D_2O$). MS (ESI/APCI Dual) m/z: 380 [(M+Na)$^+$], 382 {[(M+2)+Na]$^+$}. IR (KBr) cm$^{-1}$: 3405, 3211, 2228, 1643, 1238, 1122, 1104. Anal. Calcd for $C_{15}H_{14}Cl_2FN_3O_2$: C, 50.30; H, 3.94; N, 11.73; Cl, 19.80; F, 5.30. Found: C, 50.32; H, 3.96; N, 11.63; Cl, 19.77; F, 5.15.

Example 9

Synthesis of (1R,2S,3R,5R,6R)-2-amino-2-cyano-3-[(3,4-dichloro benzyl)oxy]-6-fluoro bicyclo[3.1.0]hexane-6-carboxmide citrate (6b)

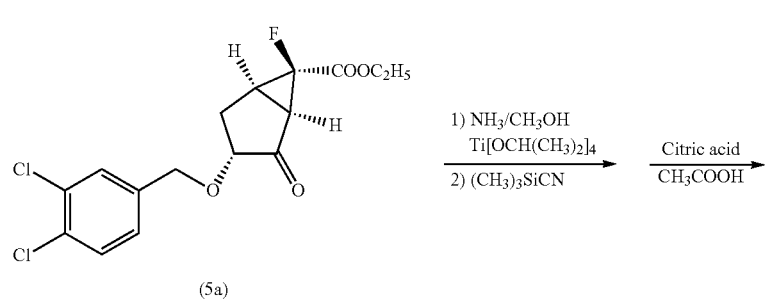

-continued

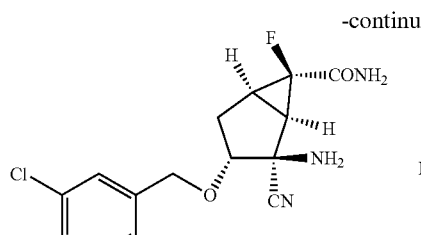
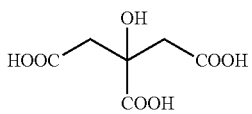

(6b)

51.0 mL suspension of 8 M ammonia-methanol containing 15.0 g (content: 97.1 wt %) of ethyl(1R,3R,5R,6R)-3-[(3,4-dichlorobenzyl)oxy]-6-fluoro-2-oxo bicycle[3.1.0]hexane-6-carboxylate (5a) was stirred for 69 min at 17 to 25° C. under argon atmosphere. The reaction solution was cooled in an ice bath and added dropwise with 14.5 g (content: 95.0 wt %) of titanium (IV) isopropoxide at 0 to 6° C. over 8 min. The ice bath was removed and the mixture was stirred at room temperature for 4.5 hrs (temperature was increased to 25° C.), and then cooled to −6° C. in a cooling incubator. 4.58 g (content: 96.0 wt %) of trimethylsilyl cyanide was added dropwise to the mixture at −6 to −4° C. for 10 min, and stirred for 17 hrs and 50 min at −5° C. and for 2 hrs and 35 min at 0° C.

To a suspension in which 73 mL of ethyl acetate is added to 14.7 g of Silica gel 60N (spherical and neutral), the reaction solution described above was added under stirring. While washing the vessel containing the reaction solution with 292 mL of ethyl acetate, the washing solution was added to the suspension of silica gel. The resulting suspension was stirred for 30 min at 14 to 20° C., filtered by suction, and washed with 365 mL of ethyl acetate. The filtrate and washing solution were combined and concentrated under reduced pressure, and the resulting residues were dried under reduced pressure to obtain 15.0 g of a crude product.

The crude product obtained was dissolved in 165 mL of acetic acid, and 7.76 g (content: 98.0 wt %) of citric acid (anhydrous) was added thereto followed by stirring for 15 hrs and 50 min at 26 to 27° C. The resulting slurry was filtered by suction and the solid was washed with 40 mL of acetic acid. The resulting solid was dried under reduced pressure at 50° C. to obtain 12.9 g of (1R,2S,3R,5R,6R)-2-amino-2-cyano-3-[(3,4-dichloro benzyl)oxy]-6-fluoro bicyclo[3.1.0]hexane-6-carboxamide citrate (6b) as a colorless solid.

mp 144° C. (hydrolysis). $^1$H NMR (600 MHz, DMSO-$d_6$) δ: 1.98-2.03 (m, 1H), 2.12-2.18 (m, 1H), 2.26-2.30 (m, 1H), 2.34-2.39 (m, 1H), 2.66 (d, J=15.1 Hz, 2H), 2.75 (d, J=15.1 Hz, 2H), 3.68-3.74 (m, 1H), 4.62 (d, J=12.4 Hz, 1H), 4.73 (d, J=12.4 Hz, 1H), 7.38 (dd, J=8.3 and 2.3 Hz, 1H), 7.63 (d, J=8.3 Hz, 1H), 7.65 (d, J=2.3 Hz, 1H), 7.66 (br s, 1H, exchangeable with D$_2$O), 7.85 (br s, 1H, exchangeable with D$_2$O). MS (ESI/APCI Dual) m/z: 380 [(M+Na)$^+$]. IR (KBr) cm$^{-1}$: 3498, 3426, 3190, 2541, 1716, 1571, 1433, 1244, 1190, 1125. Anal. Calcd for $C_{21}H_{22}Cl_2FN_3O_9$: C, 45.83; H, 4.03; N, 7.64; Cl, 12.88; F, 3.45. Found: C, 45.69; H, 4.09; N, 7.55; Cl, 12.72; F, 3.38.

Example 10

Synthesis of (1R,3R,5R,6R)-3-[(3,4-dichlorobenzyl)oxy]-6-fluoro-2-oxybicyclo[3,1,0]hexane-6-carboxamide (5b)

[Chemical Formula 37]

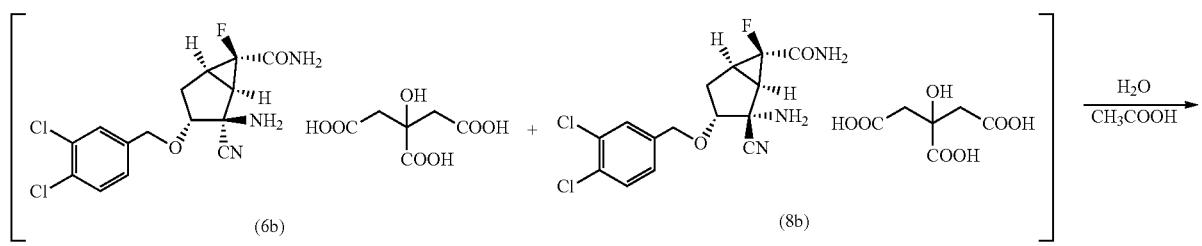
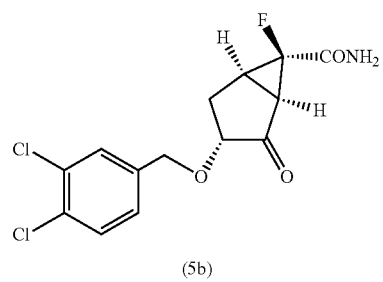

174.84 g [containing 0.351 g of (1R,2S,3R,5R,6R)-2-amino-2-cyano-3-[(3,4-dichloro benzyl)oxy]-6-fluoro bicyclo[3.1.0]hexane-6-carboxamide citrate (6b) and 3.853 g of (1R,2R,3R,5R,6R)-2-amino-2-cyano-3-[(3,4-dichloro benzyl)oxy]-6-fluorobicyclo[3.1.0]hexane-6-carboxamide citrate (8b)] of the 190.36 g of the filtrate and washing solution (acetic acid solution) obtained from the Example 9 was added with 174 mL of water and stirred for 4.5 hrs under heating at 90 to 93° C. The reaction solution was cooled to room temperature, added with ethyl acetate and water, and extracted. The organic layer was washed with water, a saturated aqueous solution of sodium hydrogen carbonate, and a saturated aqueous solution of sodium chloride in order, and dried over anhydrous magnesium sulfate. The solvent was removed by distillation under reduced pressure to give a crude product, which was then subjected to silica gel column chromatography (eluent solution: chloroform:methanol=20:1). The concentrated residues obtained were crystallized with chloroform-hexane to obtain 2.07 g of (1R,3R,5R,6R)-3-[(3,4-dichloro benzyl)oxy]-6-fluoro-2-oxo bicyclo[3.1.0]hexane-6-carboxamide (5b) as a colorless solid.

Example 11

Synthesis of (1R,2S,3R,5R,6R)-2-amino-2-cyano-3-[(3,4-dichloro benzyl)oxy]-6-fluoro bicyclo[3.1.0]hexane-6-carboxamide citrate (6b)

61.7 g (content: 49.5 wt %) of ethyl (1R,3R,5R,6R)-3-[(3,4-dichloro benzyl)oxy]-6-fluoro-2-oxo bicyclo[3.1.0]hexane-6-carboxylate (5a) was added with 106 mL of 8 M ammonia-methanol solution and stirred at room temperature. Under cooling, 30.4 g of titanium (IV) isopropoxide was added to the mixture and stirred for 1 hr while keeping the internal temperature at 20° C. or less. Subsequently, under cooling, 9.62 g of trimethyl silyl cyanide was added dropwise while keeping the internal temperature at 5° C. or less and stirred for 12 hrs. 271 g of ethyl acetate was added to the reaction solution. In a separate vessel, 31 g of Silica gel 60N (spherical and neutral) and 139 g of ethyl acetate were mixed under stirring, and then the above reaction solution diluted with ethyl acetate was added dropwise to the suspension. After stirring for 30 min at room temperature, solids were filtered and washed with 690 g of ethyl acetate. The filtrate and washing solution were combined and the residues obtained by concentrating them under reduced pressure were dissolved in 446 g of acetic acid and added with 19.4 g of citric acid (anhydrous). The mixture was stirred for 13 hrs at room temperature, and the precipitated solids were collected by filtration and washed with 163 g of acetic acid. The resulting solids were dried under reduced pressure at 50° C. to obtain 23.4 g of (1R,2S,3R,5R,6R)-2-amino-2-cyano-3-[(3,4-dichloro benzyl)oxy]-6-fluoro bicyclo[3.1.0]hexane-6-carboxamide citrate (6b) as a light brown solid.

[Chemical Formula 38]

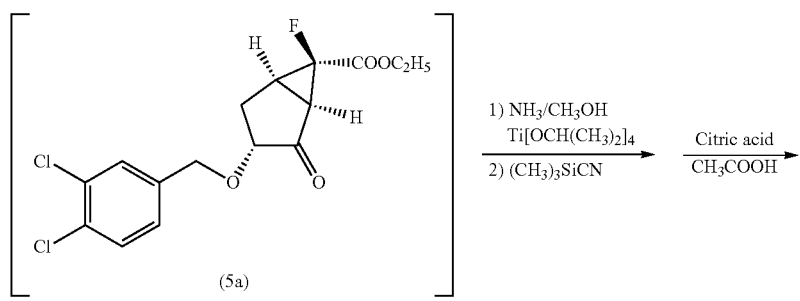

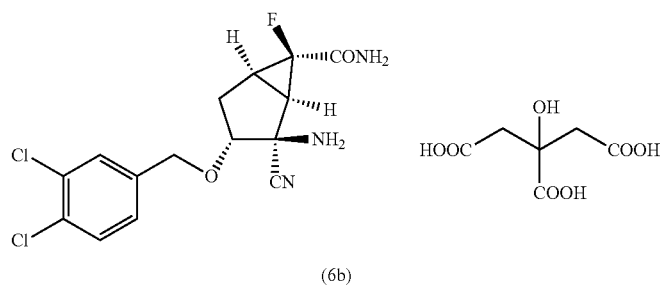

Example 12

Synthesis of (1R,2S,3R,5R,6R)-2-amino-2-cyano-3-[(3,4-dichloro benzyl)oxy]-6-fluoro bicyclo[3.1.0]hexane-6-carboxamide L-tartarate (6c)

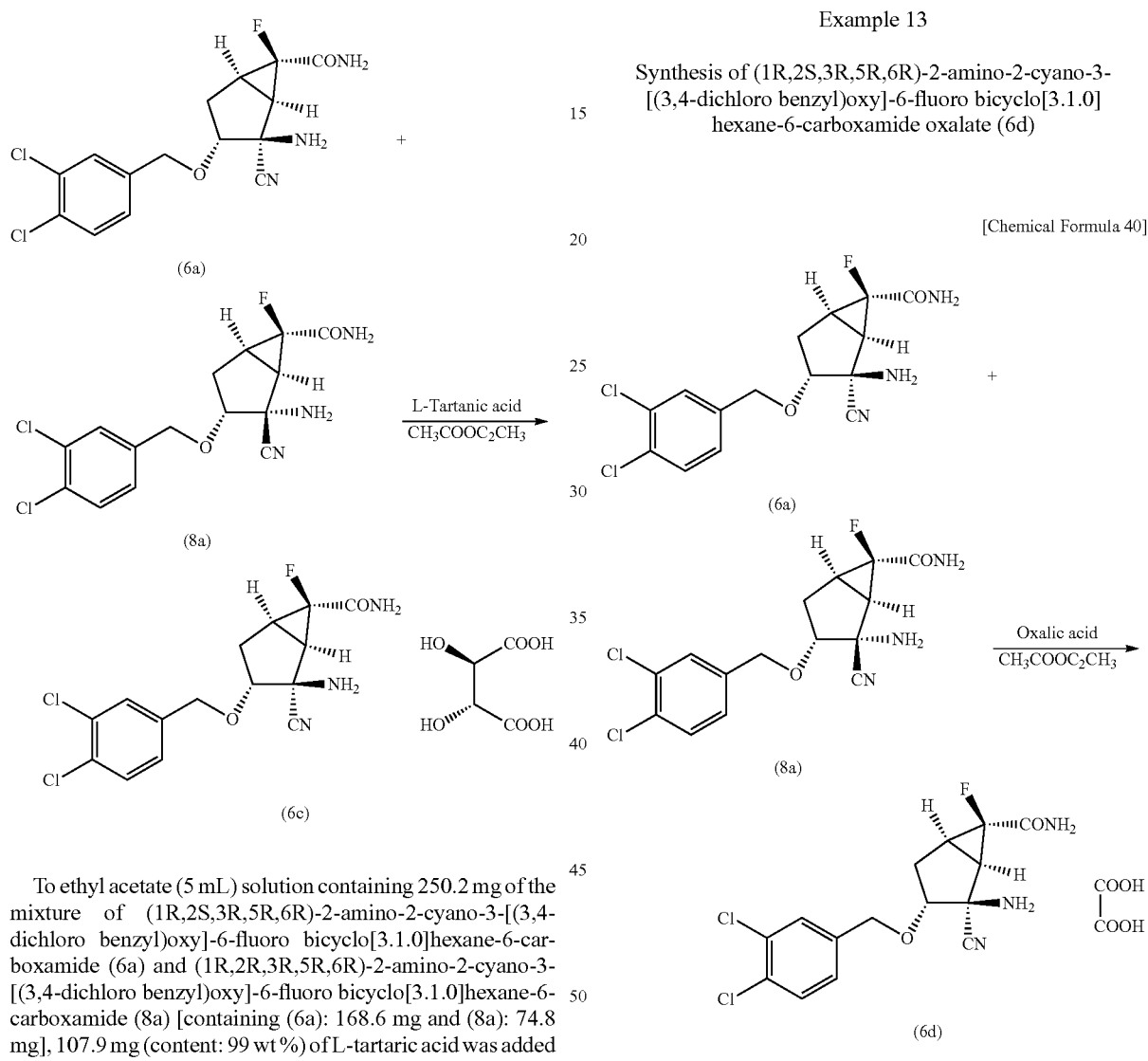

To ethyl acetate (5 mL) solution containing 250.2 mg of the mixture of (1R,2S,3R,5R,6R)-2-amino-2-cyano-3-[(3,4-dichloro benzyl)oxy]-6-fluoro bicyclo[3.1.0]hexane-6-carboxamide (6a) and (1R,2R,3R,5R,6R)-2-amino-2-cyano-3-[(3,4-dichloro benzyl)oxy]-6-fluoro bicyclo[3.1.0]hexane-6-carboxamide (8a) [containing (6a): 168.6 mg and (8a): 74.8 mg], 107.9 mg (content: 99 wt %) of L-tartaric acid was added and stirred for 19 hrs and 15 min at room temperature. The resulting slurry was filtered under suction, washed with 2 mL of ethyl acetate, and dried under reduced pressure at room temperature. 254.6 mg of the resulting colorless powder (265.9 mg obtained) was suspended in 2.5 mL of ethyl acetate, and stirred at room temperature for 15.5 hrs. The resulting slurry was filtered under suction, washed with 2 mL of ethyl acetate, and dried under reduced pressure at room temperature to obtain 206.9 mg of (1R,2S,3R,5R,6R)-2-amino-2-cyano-3-[(3,4-dichloro benzyl)oxy]-6-fluoro bicyclo[3.1.0]hexane-6-carboxamide L-tartarate (6c) as a colorless solid.

mp 154-157° C. (hydrolysis). $^1$H NMR (600 MHz, DMSO-d$_6$) δ: 1.98-2.03 (m, 1H), 2.11-2.18 (m, 1H), 2.26-2.30 (m, 1H), 2.34-2.39 (m, 1H), 3.68-3.73 (m, 1H), 4.31 (s, 2H), 4.62 (d, J=12.4 Hz, 1H), 4.73 (d, J=12.4 Hz, 1H), 7.38 (dd, J=8.3 and 2.1 Hz, 1H), 7.64 (d, J=8.3 Hz, 1H), 7.65 (d, J=2.1 Hz, 1H), 7.66 (br s, 1H, exchangeable with D$_2$O), 7.85 (br s, 1H, exchangeable with D$_2$O). MS (ESI/APCI Dual) m/z: 380 [(M+Na)$^+$]. IR (KBr) cm$^{-1}$: 3325, 1679, 1601, 1426, 1380, 1131, 1068, 683. Anal. Calcd for C$_{19}$H$_{20}$Cl$_2$FN$_3$O$_8$ (adhesion of 0.5 H$_2$O): C, 44.12; H, 4.09; N, 8.12; Cl, 13.71; F, 3.67. Found: C, 44.22; H, 3.97; N, 7.98; Cl, 13.57; F, 3.71.

Example 13

Synthesis of (1R,2S,3R,5R,6R)-2-amino-2-cyano-3-[(3,4-dichloro benzyl)oxy]-6-fluoro bicyclo[3.1.0]hexane-6-carboxamide oxalate (6d)

To ethyl acetate (5 mL) solution containing 251.0 mg of the mixture of (1R,2S,3R,5R,6R)-2-amino-2-cyano-3-[(3,4-dichloro benzyl)oxy]-6-fluoro bicyclo[3.1.0]hexane-6-carboxamide (6a) and (1R,2R,3R,5R,6R)-2-amino-2-cyano-3-[(3,4-dichloro benzyl)oxy]-6-fluoro bicyclo[3.1.0]hexane-6-carboxamide (8a) [containing (6a): 171.5 mg and (8a): 75.1 mg], 67.7 mg (content: 98 wt %) of oxalic acid was added and stirred for 17 hrs and 50 min at room temperature. The resulting slurry was filtered under suction, washed with 2 mL of ethyl acetate, and dried under reduced pressure at room temperature. 217.0 mg of the resulting colorless powder (229.1 mg obtained) was suspended in 2.5 mL of ethyl acetate, and stirred at room temperature for 15.5 hrs. The resulting slurry was filtered under suction, washed with 2 mL of ethyl acetate, and dried under reduced pressure at room temperature to obtain 193.5 mg of (1R,2S,3R,5R,6R)-2-amino-2-cyano-3-[(3,4-dichloro benzyl)oxy]-6-fluorobicyclo[3.1.0]hexane-6-carboxamide oxalate (6d) as a colorless solid.

mp 156-159° C. (hydrolysis). $^1$H NMR (600 MHz, DMSO-$d_6$) δ: 1.99-2.04 (m, 1H), 2.12-2.19 (m, 1H), 2.27-2.31 (m, 1H), 2.35-2.40 (m, 1H), 3.69-3.75 (m, 1H), 4.62 (d, J=12.4 Hz, 1H), 4.73 (d, J=12.4 Hz, 1H), 7.38 (dd, J=8.3 and 1.8 Hz, 1H), 7.64 (d, J=8.3 Hz, 1H), 7.65 (d, J=1.8 Hz, 1H), 7.67 (br s, 1H, exchangeable with $D_2O$), 7.85 (br s, 1H, exchangeable with $D_2O$). MS (ESI/APCI Dual) m/z: 380 [(M+Na)$^+$]. IR (KBr) cm$^{-1}$: 3431, 1765, 1710, 1694, 1599, 1244, 1139, 722. Anal. Calcd for $C_{17}H_{16}Cl_2FN_3O_6$: C, 45.55; H, 3.60; N, 9.37; Cl, 15.82; F, 4.24. Found: C, 45.43; H, 3.65; N, 9.21; Cl, 15.62; F, 4.16.

Example 14

Synthesis of (1R,2S,3R,5R,6R)-2-amino-2-cyano-3-[(3,4-dichloro benzyl)oxy]-6-fluoro bicyclo[3.1.0]hexane-6-carboxamide p-toluene sulfonate (6e)

[Chemical Formula 41]

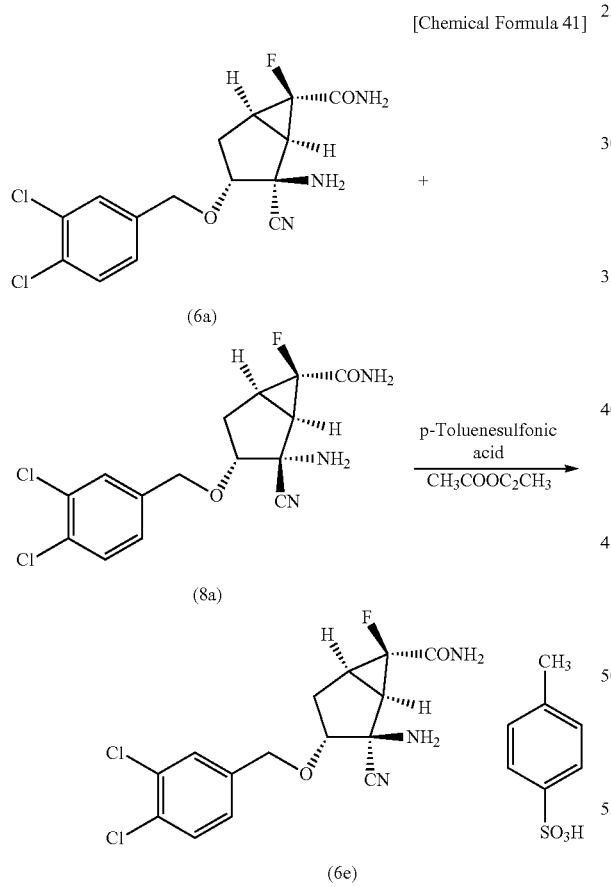

To ethyl acetate (5 mL) solution containing 251.7 mg of the mixture of ((1R,2S,3R,5R,6R)-2-amino-2-cyano-3-[(3,4-dichloro benzyl)oxy]-6-fluoro bicyclo[3.1.0]hexane-6-carboxamide (6a) and (1R,2R,3R,5R,6R)-2-amino-2-cyano-3-[(3,4-dichloro benzyl)oxy]-6-fluoro bicyclo[3.1.0]hexane-6-carboxamide (8a) [containing (6a): 172.0 mg and (8a): 75.3 mg], 139.4 mg (content: 98 wt %) of p-toluene sulfonic acid was added and stirred for 18 hrs and 20 min at room temperature. The resulting slurry was filtered under suction, washed with 2 mL of ethyl acetate, and dried under reduced pressure at room temperature. 233.2 mg of the resulting colorless powder (248.0 mg obtained) was suspended in 2.5 mL of ethyl acetate, and stirred at room temperature for 15.5 hrs. The resulting slurry was filtered under suction, washed with 2 mL of ethyl acetate, and dried under reduced pressure at room temperature to obtain 220.6 mg of (1R,2S,3R,5R,6R)-2-amino-2-cyano-3-[(3,4-dichloro benzyl)oxy]-6-fluoro bicyclo[3.1.0]hexane-6-carboxamide p-toluene sulfonate (6e) as a colorless solid.

mp 198-202° C. (hydrolysis). $^1$H NMR (600 MHz, DMSO-$d_6$) δ: 2.25-2.31 (m, 2H), 2.29 (s, 3H), 2.51-2.57 (m, 2H), 4.08-4.15 (m, 1H), 4.65 (s, 2H), 7.11 (d, J=8.0 Hz, 2H), 7.39 (dd, J=8.3 and 1.8 Hz, 1H), 7.48 (d, J=8.0 Hz, 2H), 7.66 (d, J=8.3 Hz, 1H), 7.68 (d, J=1.8 Hz, 1H), 7.86 (br s, 1H, exchangeable with $D_2O$), 7.96 (br s, 1H, exchangeable with $D_2O$). MS (ESI/APCI Dual) m/z: 380 [(M+Na)$^+$]. IR (KBr) cm$^{-1}$: 3391, 3165, 1688, 1544, 1207, 1168, 1158, 1132, 1011, 687, 564. Anal. Calcd for $C_{22}H_{22}Cl_2FN_3O_5S$: C, 49.82; H, 4.18; N, 7.92; Cl, 13.37; F, 3.58; S, 6.05. Found: C, 49.68; H, 4.16; N, 7.82; Cl, 13.27; F, 3.81; S, 5.98.

Example 15

Synthesis of (1R,2S,3R,5R,6R)-2-amino-2-cyano-3-[(3,4-dichloro benzyl)oxy]-6-fluoro bicyclo[3.1.0]hexane-6-carboxylic acid (6f)

[Chemical Formula 42]

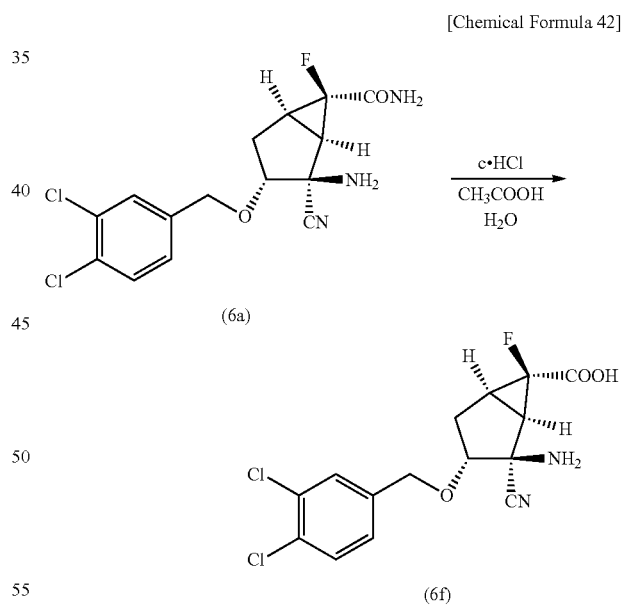

A mixture containing 22.5 mg of (1R,2S,3R,5R,6R)-2-amino-2-cyano-3-[(3,4-dichloro benzyl)oxy]-6-fluoro bicyclo[3.1.0]hexane-6-carboxamide (6a), 0.1 mL of acetic acid, 0.1 mL of water, and 0.2 mL of concentrated hydrochloric acid was stirred for 6 hrs approximately under heating at 75° C. (external temperature). The reaction mixture was concentrated under reduced pressure to obtain 24.6 mg of (1R,2S,3R,5R,6R)-2-amino-2-cyano-3-[(3,4-dichloro benzyl)oxy]-6-fluoro bicyclo[3.1.0]hexane-6-carboxylic acid (6f) as a light brown solid.

¹H NMR (300 MHz, DMSO-$d_6$) δ: 2.21-2.32 (m, 1H), 2.33-2.42 (m, 1H), 2.52-2.59 (m, 1H), 2.59-2.65 (m, 1H), 4.00-4.13 (m, 1H), 4.63 (d, J=12.1 Hz, 1H), 4.72 (d, J=12.1 Hz, 1H), 7.03 (br s, 0.62H, exchangeable with $D_2O$), 7.06 (br s, 0.38H, exchangeable with $D_2O$), 7.20 (br s, 0.62H, exchangeable with $D_2O$), 7.23 (br s, 0.38H, exchangeable with $D_2O$), 7.37 (br s, 0.62H, exchangeable with $D_2O$), 7.39 (dd, J=8.4 and 2.1 Hz, 1H), 7.40 (br s, 0.38H, exchangeable with $D_2O$), 7.66 (d, J=8.4 Hz, 1H), 7.69 (d, J=2.1 Hz, 1H). MS (ESI/APCI Dual) m/z: 357 [(M−H)⁻].

Example 16

Synthesis of (1R,2R,3R,5R,6R)-2-amino-3-[(3,4-dichloro benzyl)oxy]-6-fluoro bicyclo[3.1.0]hexane-2,6-dicarboxamide (7a)

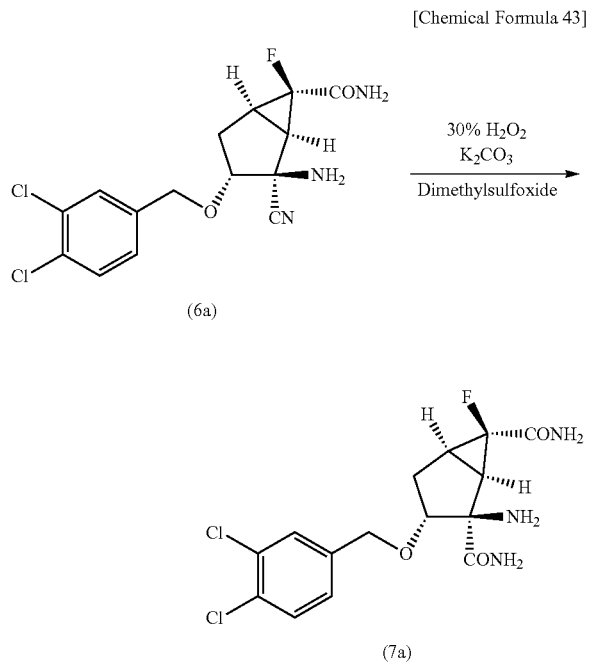

To a dimethyl sulfoxide (1.2 mL) solution containing 303.0 mg of (1R,2S,3R,5R,6R)-2-amino-2-cyano-3-[(3,4-dichloro benzyl)oxy]-6-fluoro bicyclo[3.1.0]hexane-6-carboxamide (6a), 35.5 mg of potassium carbonate was added under cooling in water bath (13° C. approximately). Subsequently, 0.2 mL of 30 wt % hydrogen peroxide was added thereto and stirred for 30 min. After stirring for 67.5 hrs at room temperature, 3 mL of water was added to the reaction solution and the precipitated solids were filtered and washed with 1.2 mL of water. The resulting solids were dried under reduced pressure at room temperature to obtain 313.2 mg of (1R, 2R,3R,5R, 6R)-2-amino-3-[(3,4-dichloro benzyl)oxy]-6-fluoro bicyclo [3.1.0]hexane-2,6-dicarboxamide (7a) as a colorless solid.

¹H NMR (600 MHz, DMSO-$d_6$) δ: 1.87-1.91 (m, 1H), 1.91-1.94 (m, 1H), 2.09-2.15 (m, 2H, exchangeable with $D_2O$), 2.19-2.24 (m, 2H), 3.60-3.66 (m, 1H), 4.49 (d, J=12.6 Hz, 1H), 4.68 (d, J=12.6 Hz, 1H), 7.21 (br s, 1H, exchangeable with $D_2O$), 7.25 (br s, 1H, exchangeable with $D_2O$), 7.20 (br s, 0.62H, exchangeable with $D_2O$), 7.23 (br s, 0.38H, exchangeable with $D_2O$), 7.29 (dd, J=8.3 and 2.3 Hz, 1H), 7.52 (br s, 1H, exchangeable with $D_2O$), 7.54 (d, J=2.3 Hz, 1H), 7.58 (d, J=8.3 Hz, 1H), 7.71 (br s, 1H, exchangeable with $D_2O$). MS (ESI/APCI Dual) m/z: 376 [(M+H)⁺].

HPLC retention time of the compound (7a) was about 8.1 min [HPLC retention time of the compound (6a) was about 19.3 min]. HPLC measurement was carried out under the condition described below.

Column: CAPCELL PAK C18 UG 120 5 μm 150×4.6 mm ID, column oven temperature: 40° C., Flow rate: 1 mL/min, Detection wavelength: 205 nm (UV), Mobile phase: liquid A: methanol, liquid B: 0.1% aqueous solution of phosphoric acid Gradient condition: liquid A/liquid B=30/70 is switched to liquid A/liquid B=80/20 over 25 min, and then liquid A/liquid B=80/20 is maintained for 5 min.

Example 17

Synthesis of (1R,2R,3R,5R,6R)-2-amino-2-carbamoyl-3-[(3,4-dichloro benzyl)oxy]-6-fluoro bicyclo [3.1.0]hexane-6-carboxylic acid (7b)

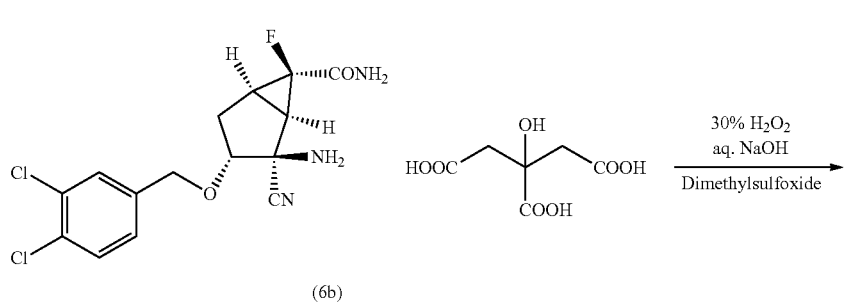

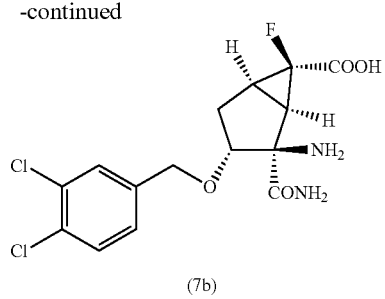

(7b)

To a dimethyl sulfoxide (1 mL) solution containing 500.1 mg of (1R,2S,3R,5R,6R)-2-amino-2-cyano-3-[(3,4-dichloro benzyl)oxy]-6-fluoro bicyclo[3.1.0]hexane-6-carboxamide citrate (6b), 0.15 mL of 30 wt % hydrogen peroxide was added at room temperature (20° C. approximately). Subsequently, 2.5 mL of 6.25 M aqueous solution of sodium hydroxide was added (temperature has risen to 51° C.) and stirred for 3 hrs and 45 min at 25° C. To the reaction solution, 4.3 mL of 3 M hydrochloric acid was added dropwise under ice cooling to adjust pH to pH 4. The slurry obtained was stirred at room temperature for 1 hr, filtered under suction, and washed with ethanol. The resulting solids were dried under reduced pressure to obtain 307.4 mg of (1R,2R,3R,5R,6R)-2-amino-2-carbamoyl-3-[(3,4-dichloro benzyl)oxy]-6-fluoro bicyclo[3.1.0]hexane-6-carboxylic acid (7b) as a colorless solid.

$^1$H NMR (600 MHz, DMSO-$d_6$) δ: 2.00-2.04 (m, 1H), 2.07-2.11 (m, 1H), 2.21-2.32 (m, 2H), 3.84-3.90 (m, 1H), 4.46 (d, J=12.2 Hz, 1H), 4.60 (d, J=12.2 Hz, 1H), 7.28 (dd, J=8.3 and 2.1 Hz, 1H), 7.31 (br s, 1H, exchangeable with $D_2O$), 7.54 (d, J=2.1 Hz, 1H), 7.56 (br s, 1H, exchangeable with $D_2O$), 7.59 (d, J=8.3 Hz, 1H). MS (ESI/APCI Dual) m/z: 377 [(M+H)$^+$].

HPLC retention time of the compound (7b) was about 12.9 min [HPLC retention time of the compound (6b) was about 19.3 min]. HPLC measurement condition was the same as the condition described in the Example 16.

Example 18

Synthesis of (1R,2R,3R,5R,6R)-2-amino-3-[(3,4-dichloro benzyl)oxy]-6-fluoro bicyclo[3.1.0]hexane-2,6-dicarboxylic acid (1a)

[Chemical Formula 45]

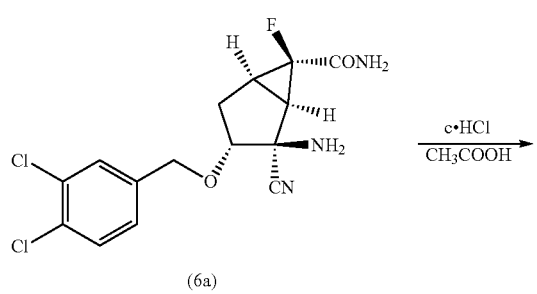

(6a)

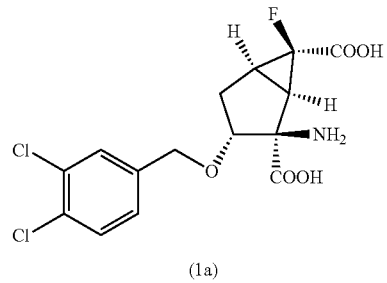

(1a)

A mixture of 0.195 g of (1R,2S,3R,5R,6R)-2-amino-2-cyano-3-[(3,4-dichloro benzyl)oxy]-6-fluoro bicyclo[3.1.0]hexane-6-carboxamide (6a), 1.9 mL of acetic acid, and 1.9 ml of concentrated hydrochloric acid was stirred for 31 hrs under heating in an oil bath at 75° C. The reaction solution was cooled to room temperature and the precipitated solids were collected by filtration. The solids were washed with 5.28 g of water and dried by air to obtain 0.094 g of (1R,2R,3R,5R,6R)-2-amino-3-[(3,4-dichloro benzyl)oxy]-6-fluoro bicyclo[3.1.0]hexane-2,6-dicarboxylic acid (1a) as a solid. The compound exhibited the proton nuclear resonance spectrum ($^1$H NMR) and the HPLC retention time that are the same as those of the compound (1a) synthesized according to conventional process (that is, Compound 34 described in the pamphlet of International Publication No. 03/061698).

$^1$H NMR (300 MHz, DMSO-$d_6$) δ: 2.07-2.14 (m, 2H), 2.25-2.41 (m, 2H), 3.87-3.99 (m, 1H), 4.43 (d, J=12.2 Hz, 1H), 4.54 (d, J=12.2 Hz, 1H), 7.30 (dd, J=8.2 and 1.9 Hz, 1H), 7.57 (d, J=1.9 Hz, 1H), 7.59 (d, J=8.2 Hz, 1H). MS (ESI/APCI Dual) m/z: 376 [(M−H)$^-$].

HPLC retention time of the compound (1a) was about 11.9 min [HPLC retention time of the compound (6a) was about 16.5 min]. HPLC measurement was carried out under the condition described below.

Column: CAPCELL PAK C18 UG 120 5 μm 150×4.6 mm ID, column oven temperature: 40° C., Flow rate: 1 mL/min, Detection wavelength: 205 nm (UV), Mobile phase: liquid A: acetonitrile, liquid B: 0.1% aqueous solution of phosphoric acid Gradient condition: liquid A/liquid B=10/90 is switched to liquid A/liquid B=80/20 over 25 min, and then liquid A/liquid B=80/20 is maintained for 5 min.

Example 19

Synthesis of (1R,2R,3R,5R,6R)-2-amino-3-[(3,4-dichloro benzyl)oxy]-6-fluoro bicyclo[3.1.0]hexane-2,6-dicarboxylic acid (1a)

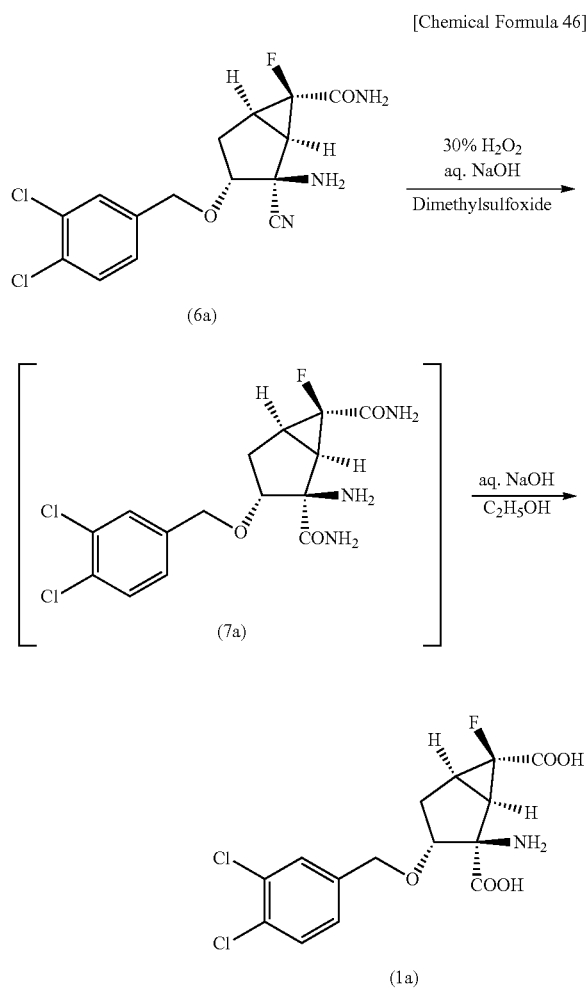

[Chemical Formula 46]

To a dimethyl sulfoxide (0.3 mL) containing 99.2 mg of (1R,2S,3R,5R,6R)-2-amino-2-cyano-3-[(3,4-dichloro benzyl)oxy]-6-fluoro bicyclo[3.1.0]hexane-6-carboxamide (6a), 13 μL of 25 wt % aqueous solution of sodium hydroxide was added under cooling in water bath. Subsequently, 1.0 mL of 30 wt % hydrogen peroxide was added. After stirring for 30 min at room temperature, part of the reaction solution was collected and subjected to HPLC measurement. As a result, it was found that the peak at about 19.3 min, which corresponds to the retention time of the reacting material (6a), has disappeared and only the peak at about 8.1 min, which corresponds to the retention time of (1R,2R,3R,5R,6R)-2-amino-3-[(3,4-dichloro benzyl)oxy]-6-fluoro bicyclo[3.1.0]hexane-2,6-dicarboxamide (7a), is appeared (condition for HPLC measurement is the same as the condition described in the Example 16).

Subsequently, after stirring for 45 min at room temperature, 0.6 mL of ethanol and 1 mL of 25 wt % aqueous solution of sodium hydroxide were added to the reaction solution and stirred for 4 hrs at 75° C. and for 18 hrs at room temperature. 3.0 mL of 3 M hydrochloric acid was added to the reaction solution under ice cooling and stirred for 4 hrs at room temperature. The resulting slurry was filtered under suction and dried under reduced pressure to obtain 80.3 mg of (1R,2R,3R,5R,6R)-2-amino-3-[(3,4-dichloro benzyl)oxy]-6-fluoro bicyclo[3.1.0]hexane-2,6-dicarboxylic acid (1a) as a light yellow solid.

Example 20

Synthesis of (1R,2R,3R,5R,6R)-2-amino-3-[(3,4-dichloro benzyl)oxy]-6-fluoro bicyclo[3.1.0]hexane-2,6-dicarboxylic acid (1a)

[Chemical Formula 47]

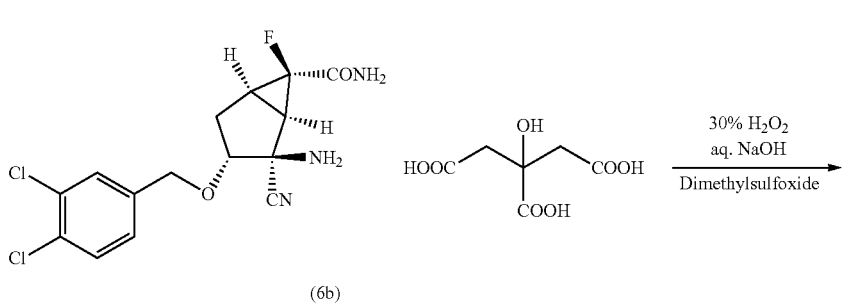

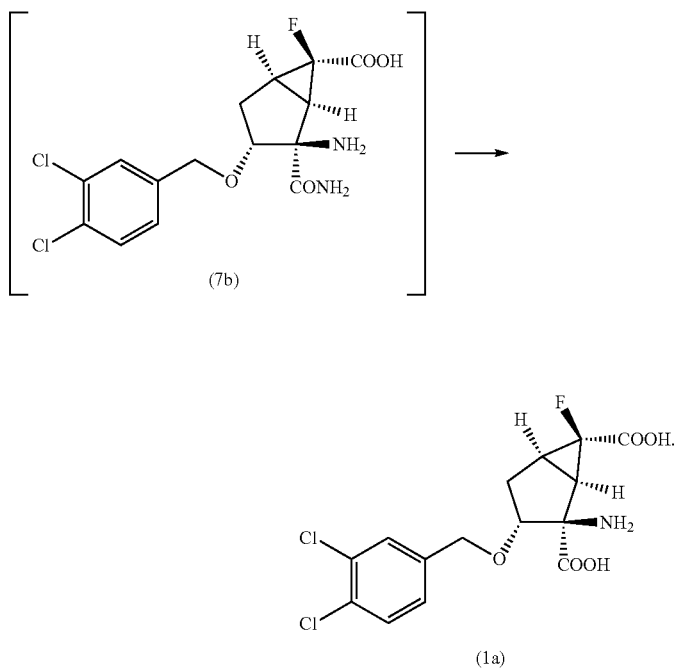

To a dimethyl sulfoxide (0.4 mL) containing 200.3 mg of (1R,2S,3R,5R,6R)-2-amino-2-cyano-3-[(3,4-dichloro benzyl)oxy]-6-fluoro bicyclo[3.1.0]hexane-6-carboxamide citrate (6b), 0.06 mL of 30 wt % hydrogen peroxide was added at room temperature. Subsequently, 1 mL of 6.25 M aqueous solution of sodium hydroxide was added. After stirring for 1 hr at room temperature, part of the reaction solution was collected and subjected to HPLC measurement. As a result, it was found that the peak at about 19.3 min, which corresponds to the retention time of the reacting material (6b), has disappeared and only the peak at about 12.7 min, which corresponds to the retention time of (1R, 2R,3R,5R,6R)-2-amino-2-carbamoyl-3-[(3,4-dichloro benzyl)oxy]-6-fluoro bicyclo [3.1.0]hexane-6-carboxylic acid (7b), is appeared (condition for HPLC measurement is the same as the condition described in the Example 16).

Subsequently, after stirring for 30 min at room temperature, the reaction solution was stirred for 2 hrs at 92 to 100° C., 16 hrs at room temperature, and 1 hr at 100° C. After cooling to room temperature, the reaction solution was added dropwise with 0.22 mL of 3 M hydrochloric acid (pH 1), stirred for 2 hrs and 25 min at room temperature, and cooled for 10 min on ice. The resulting slurry was filtered under suction and dried under reduced pressure to obtain 141.4 mg of (1R,2R, 3R,5R,6R)-2-amino-3-[(3,4-dichloro benzyl)oxy]-6-fluoro bicyclo[3.1.0]hexane-2,6-dicarboxylic acid (1a) as a light yellow solid.

Example 21

Synthesis of (1R,2R,3R,5R,6R)-2-amino-3-[(3,4-dichloro benzyl)oxy]-6-fluoro bicyclo[3.1.0]hexane-2,6-dicarboxylic acid (1a)

[Chemical Formula 48]

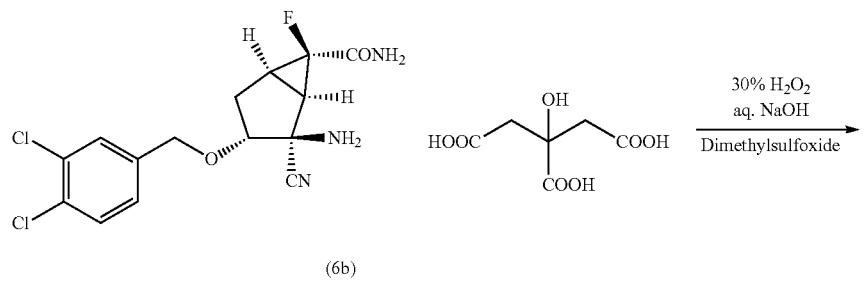

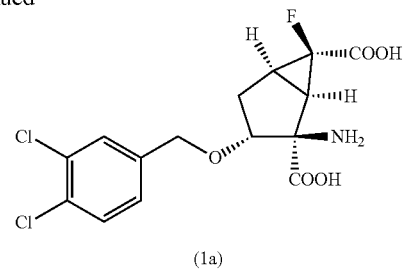

(1a)

To 32.5 g of (1R,2S,3R,5R,6R)-2-amino-2-cyano-3-[(3,4-dichloro benzyl)oxy]-6-fluoro bicyclo[3.1.0]hexane-6-carboxamide citrate (6b), 63.9 g of dimethyl sulfoxide and 9.88 g of 30 wt % hydrogen peroxide were added and stirred for 10 min. To the mixture, 202 g of 20 wt % aqueous solution of sodium hydroxide was added dropwise over 1 hr, and stirred for 10 min after completing the dropwise addition. The reaction mixture was heated and stirred for about 13 hrs at the internal temperature of 80° C. or more. The reaction solution was cooled in an ice bath until the internal temperature reaches 16° C., and pH was adjusted to approximately 1 to 2 with hydrochloric acid. The precipitated solids were filtered and collected to yield solids, which are then washed with 290 mL of a mixture solution of ethanol:water=1:1 (v/v) and 90 mL of ethanol in order. The resulting solids were dried under reduced pressure at 50° C. to obtain 21.1 g of (1R,2R,3R,5R,6R)-2-amino-3-[(3,4-dichloro benzyl)oxy]-6-fluoro bicyclo[3.1.0]hexane-2,6-dicarboxylic acid (1a) as a light yellow to light brown solid.

Example 22

Synthesis of (1R,2R,3R,5R,6R)-3-[(3,4-dichloro benzyl)oxy]-6-fluoro-2',5'-dioxospiro[bicyclo[3.1.0]hexane-2,4'-imidazolidine]-6-carboxylic acid (9a) and (1R,2S,3R,5R,6R)-3-[(3,4-dichloro benzyl)oxy]-6-fluoro-2',5'-dioxospiro[bicyclo[3.1.0]hexane-2,4'-imidazolidine]-6-carboxylic acid (10a)

[Chemical Formula 49]

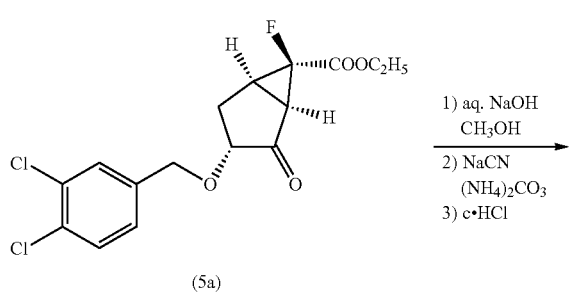

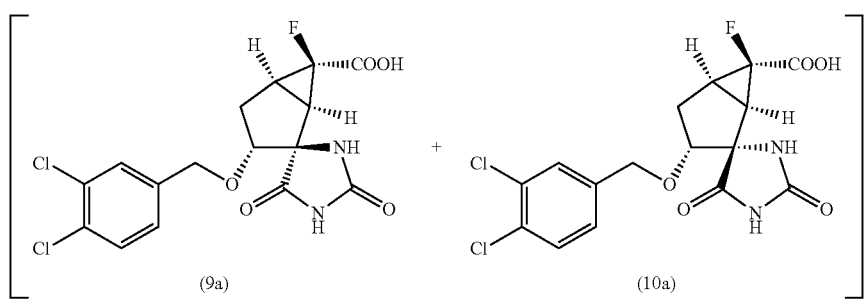

To a mixture containing 0.928 g of ethyl (1R,3R,5R,6R)-3-[(3,4-dichloro benzyl)oxy]-6-fluoro-2-oxo bicyclo[3.1.0]hexane-6-carboxylate (5a), 4.70 g of methanol, and 4.66 g of water, 0.1073 g (content: 96 wt %) of sodium hydroxide was added and stirred for 2 hrs and 40 min at room temperature. One hour and ten minutes after starting the reaction, part of the reaction solution was collected and subjected to HPLC measurement. As a result, it was found that the peak at about 27.5 min, which corresponds to the retention time of the reacting material (5a), has disappeared and the peak at about 25.7 min, which is believed to be the retention time of the carboxylate resulting from hydrolysis of the ester, is observed (condition for HPLC measurement is the same as the condition described in the Example 16, ditto for the followings). To the reaction solution, 2.042 g (content: 97 wt %) of ammonium carbonate and 0.55 g (content: 97 wt %) of sodium cyanide were added and stirred for 6 hrs under heating in an oil bath at 65° C. followed by stirring for about 14 hrs at room temperature. Part of the reaction solution was collected and subjected to HPLC measurement. As a result, it was found that the peak at retention time of about 25.7 min has disappeared, and the peak at about 19.6 min, which corresponds to (1R,2R,3R,5R,6R)-3-[(3,4-dichloro benzyl)oxy]-6-fluoro-2',5'-dioxospiro[bicyclo[3.1.0]hexane-2,4'-imidazolidine]-6-carboxylic acid (9a), is appeared and the peak at about 18.8 min, which corresponds to (1R,2S,3R, 5R,6R)-3-[(3,4-dichloro benzyl)oxy]-6-fluoro-2',5'-dioxospiro[bicyclo[3.1.0]hexane-2,4'-imidazolidine]-6-carboxylic acid (10a), is appeared, with the peak area ratio of (9a)/(10a)=2.2.

To the reaction solution, 3.49 g (content: 35 wt %) of concentrated hydrochloric acid was added. The resulting suspension was filtered to give a solid. The solid obtained was subjected to HPLC measurement, and as a result, it was confirmed that it is a mixture of the compounds of (9a) and (10a) with the peak area ratio of (9a)/(10a)=6.6.

INDUSTRIAL APPLICABILITY

With respect to the process of producing 3-alkoxy-2-amino-6-fluoro bicyclo[3.1.0]hexane-2,6-dicarboxylic acid derivative which is useful as an antagonist for a metabotropic glutamate receptor or a salt thereof, it becomes possible by the present invention to provide a production process which solves the problems relating to safety issue, can be easily scaled up, is effective in terms of cost, has good efficiency as having fewer reaction steps, and therefore is suitable for large scale production.

The invention claimed is:

1. A process for producing a 3-alkoxy-2-amino-6-fluoro bicyclo[3.1.0]hexane-2,6-dicarboxylic acid derivative represented by the formula (I) or a salt thereof,

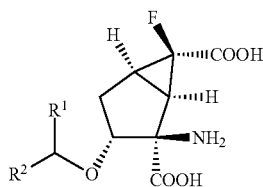

where in the formula (I), $R^1$ and $R^2$, which may be the same or different from each other, are selected from the group consisting of a hydrogen atom, a $C_{1-10}$ alkyl group, a $C_{2-10}$ alkenyl group, a phenyl group, a naphthyl group, a naphthyl group substituted with 1 to 7 halogen atoms, a heteroaromatic group, and a phenyl group substituted with 1 to 5 substituent groups selected from a group consisting of a halogen atom, a $C_{1-10}$ alkyl group, a $C_{1-10}$ alkoxy group, a trifluoro methyl group, a phenyl group, a hydroxy carbonyl group, an amino group, a nitro group, a cyano group, and a phenoxy group; $R^1$ and $R^2$ may bind to each other to form a cyclic structure, the process comprising:

(A) converting a compound represented by the formula (II) or a salt thereof to a compound represented by the formula (III) or 20 a salt thereof,

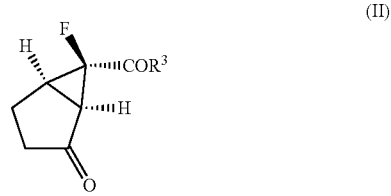

where in the formula (II), $R^3$ is selected from the group consisting of a $C_{1-6}$ alkoxy group, an amino group, and a hydroxyl group,

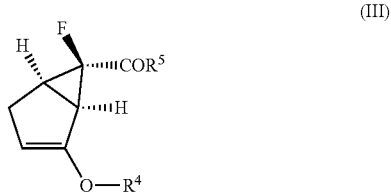

where in the formula (III), $R^4$ represents $-SiR^{41}R^{42}R^{43}$ wherein $R^{41}$, $R^{42}$, and $R^{43}$, which may be the same or different from each other, each represent a $C_{1-6}$ alkyl group; $R^5$ is selected from the group consisting of a $C_{1-6}$ alkoxy group, an amino group, and a hydroxyl group, (B) converting the compound represented by the formula (III) or a salt thereof to a compound represented by the formula (IV) or a salt thereof,

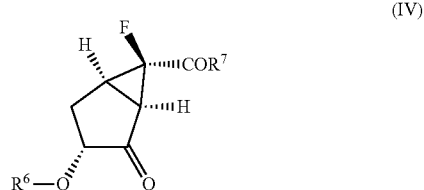

where in the formula (IV), $R^6$ is selected from the group consisting of a hydrogen atom, a benzoyl group, a benzoyl group substituted with a halogen atom, and $-SiR^{61}R^{62}R^{63}$ wherein $R^{61}$, $R^{62}$, and $R^{63}$, which may be the same or different from each other, each represent a $C_{1-6}$ alkyl group; $R^7$ is selected from the group consisting of a $C_{1-6}$ alkoxy group, an amino group, and a hydroxyl group, (C) converting the compound represented by the formula (IV) or a salt thereof to a compound represented by the formula (V) or a salt thereof,

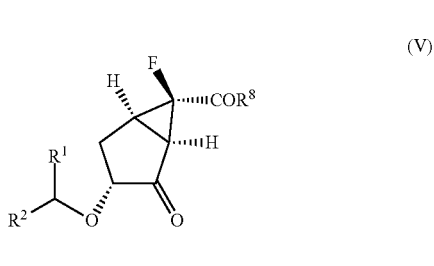

(V)

where in the formula (V), $R^1$ and $R^2$ are as defined above and $R^8$ is selected from the group consisting of a $C_{1-6}$ alkoxy group, an amino group, and a hydroxyl group, (D) converting the compound represented by the formula (V) or a salt thereof to a compound represented by the formula (VI) or a salt thereof,

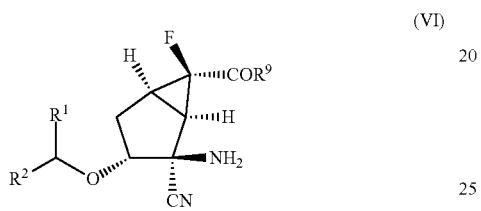

(VI)

where in the formula (VI), $R^1$ and $R^2$ are as defined above and $R^9$ is selected from the group consisting of a $C_{1-6}$ alkoxy group, an amino group, and a hydroxyl group, and (E) converting the compound represented by the formula (VI) or a salt thereof to the compound represented by the formula (I) or a salt thereof.

2. A process for producing a 3-alkoxy-2-amino-6-fluoro bicyclo[3.1.0]hexane-2,6-dicarboxylic acid derivative represented by the formula (I) or a salt thereof, the process comprising converting a compound represented by the formula (VI) or a salt thereof to the compound represented by the formula (I) or a salt thereof

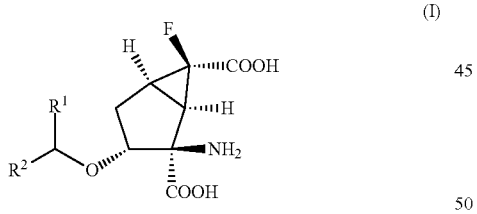

(I)

where in the formula (I), $R^1$ and $R^2$, which may be the same or different from each other, are selected from the group consisting of a hydrogen atom, a $C_{1-10}$ alkyl group, a $C_{2-10}$ alkenyl group, a phenyl group, a naphthyl group, a naphthyl group substituted with 1 to 7 halogen atoms, a heteroaromatic group, and a phenyl group substituted with 1 to 5 substituent groups selected from a group consisting of a halogen atom, a $C_{1-10}$ alkyl group, a $C_{1-10}$ alkoxy group, a trifluoro methyl group, a phenyl group, a hydroxy carbonyl group, an amino group, a nitro group, a cyano group, and a phenoxy group; $R^1$ and $R^2$ may bind to each other to form a cyclic structure,

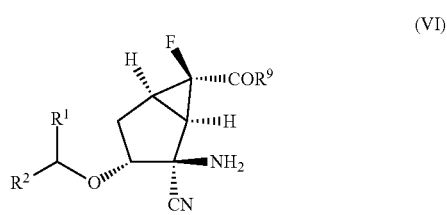

(VI)

where in the formula (VI), $R^1$ and $R^2$ are as defined above and $R^9$ is selected from the group consisting of a $C_{1-6}$ alkoxy group, an amino group, and a hydroxyl group.

3. The process according to claim 1 wherein the step (E) converting the compound represented by the formula (VI) or a salt thereof to the compound represented by the formula (I) or a salt thereof comprises the steps of:

(F) converting the compound represented by the formula (VI) or a salt thereof to a compound represented by the formula (VII) or a salt thereof,

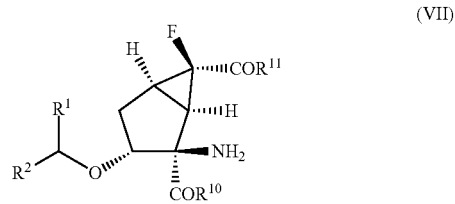

(VII)

where in the formula (VII), $R^1$ and $R^2$ are as defined above; $R^{10}$ is selected from the group consisting of a $C_{1-6}$ alkoxy group, an amino group and a hydroxyl group, and $R^{11}$ is selected from the group consisting of a $C_{1-6}$ alkoxy group, an amino group, and a hydroxyl group, with the proviso that $R^{10}$ and $R^{11}$ do not simultaneously represent a hydroxyl group, and (G) converting the compound represented by the formula (VII) or a salt thereof to the compound represented by the formula (I) or a salt thereof.

* * * * *